United States Patent
Abu Khabar et al.

(10) Patent No.: US 11,649,504 B2
(45) Date of Patent: May 16, 2023

(54) SET OF GENES FOR USE IN A METHOD OF PREDICTING THE LIKELIHOOD OF A BREAST CANCER PATIENT'S SURVIVAL

(71) Applicant: King Faisal Specialist Hospital and Research Centre, Riyadh (SA)

(72) Inventors: Khalid S. Abu Khabar, Riyadh (SA); Tala Bakheet, Riyadh (SA); Edward Hitti, Riyadh (SA); Nora Al-Souhibani, Riyadh (SA); Adher Alsayed, Riyadh (SA); Taher Twegieri, Riyadh (SA); Asma Tulbah, Riyadh (SA)

(73) Assignee: KING FAISAL SPECIALIST HOSPITAL & RESEARCH CENTRE, Riyadh (SA)

(*) Notice: Subject to any disclaimer, the term of this patent is extended or adjusted under 35 U.S.C. 154(b) by 141 days.

(21) Appl. No.: 15/424,797

(22) Filed: Feb. 4, 2017

(65) Prior Publication Data

US 2017/0226589 A1 Aug. 10, 2017

Related U.S. Application Data

(60) Provisional application No. 62/292,482, filed on Feb. 8, 2016.

(30) Foreign Application Priority Data

Feb. 8, 2016 (EP) .................................... 16154643

(51) Int. Cl.
  *C12Q 1/6886* (2018.01)
  *G16H 50/30* (2018.01)
  *G06N 7/00* (2006.01)

(52) U.S. Cl.
  CPC ........... *C12Q 1/6886* (2013.01); *G06N 7/005* (2013.01); *G16H 50/30* (2018.01); *C12Q 2600/118* (2013.01); *C12Q 2600/158* (2013.01)

(58) Field of Classification Search
  CPC ............ C12Q 1/6886; C12Q 2600/118; C12Q 2600/158
  See application file for complete search history.

(56) References Cited

U.S. PATENT DOCUMENTS

2009/0311700 A1* 12/2009 Gehrmann ........... C12Q 1/6886
                                                     435/6.16
2013/0281502 A1* 10/2013 Sgroi ...................... A61P 35/00
                                                     514/383

OTHER PUBLICATIONS

Kung (Mol. Cancer Therapeutics, 2014, 13(8): 2104-15).*
Shubbar (BMC Cancer, 2013, 13:1, pp. 1-10).*
Sparano (Breast Cancer Res Treat, 2012, 1134:751-757).*
Al-Souhibani, N., et al., "Posttranscriptional control of the chemokine receptor CXCR4 expression in cancer cells." Carcinogenesis, 2014, 35(9): 1983-1992.
Curtis, C. et al., "The genomic and transcriptomic architecture of 2,000 breast tumours reveals novel subgroups." Nature, 2012, 486(7403): 346-352.
Gyorffy, B., et al., "An online survival analysis tool to rapidly assess the effect of 22,277 genes on breast cancer prognosis using microarray data of 1,809 patients " Breast Cancer Res Treat, 2010, 123: 725-731.
Mihaly, Z., Kormos, M., "A meta-analysis of gene expression-based biomarkers predicting outcome after tamoxifen treatment in breast cancer." Breast Cancer Res Treat, 2013, 140: 219-232.

* cited by examiner

*Primary Examiner* — Sarae L Bausch
(74) *Attorney, Agent, or Firm* — Saliwanchik, Lloyd & Eisenschenk

(57) ABSTRACT

The present invention relates to a set of genes for use in a method of predicting the likelihood of a breast cancer patient's survival or of predicting the likelihood of a recurrence and/or aggressiveness of a breast cancer in a breast cancer patient. The present invention also relates to a method for predicting the likelihood of a breast cancer patient's survival or the likelihood of the recurrence or aggressiveness of a breast cancer in a breast cancer patient, as well as to a kit for use in such method.

10 Claims, 6 Drawing Sheets

Specification includes a Sequence Listing.

SET OF GENES FOR USE IN A METHOD OF PREDICTING THE LIKELIHOOD OF A BREAST CANCER PATIENT'S SURVIVAL

CROSS-REFERENCE TO A RELATED APPLICATION

This application claims the benefit of U.S. Provisional Application Ser. No. 62/292,482, filed Feb. 8, 2016. This application also claims priority to European Patent Application No. EP 16154643.7, filed Feb. 8, 2016; both of which are incorporated herein by reference in their entirety.

The Sequence Listing for this application is labeled "SeqList-03Feb17.txt", which was created on Feb. 3, 2017, and is 114 KB. The entire content is incorporated herein by reference in its entirety.

FIELD OF THE INVENTION

The present invention relates to a set of genes for use in a method of predicting the likelihood of a breast cancer patient's survival or of predicting the likelihood of a recurrence and/or aggressiveness of a breast cancer in a breast cancer patient. The present invention also relates to a method for predicting the likelihood of a breast cancer patient's survival or the likelihood of the recurrence or aggressiveness of a breast cancer in a breast cancer patient, as well as to a kit for use in such method.

BACKGROUND OF THE INVENTION

Uncontrolled cellular growth and the ability to invade surrounding tissues are two basic characteristics of cancer. A complex multitude of changes in gene expression patterns exist in all cancers, and a growing body of evidence has linked aberrantly elevated and prolonged expressions of various genes and their mRNAs, respectively, to cancer, including genes participating in angiogenesis, chemotaxis and invasion. Examples of such genes include epidermal growth factor (EGF), estrogen receptor, cyclooxygenase-2, vascular endothelial growths factor (VEGF), matrix metalloproteinase, such as MMP-1 and MMP-9m, urokinase-type plasminogen activator (uPA), uPA receptor (uPAR), chemokine receptor CXCR4 and several others.

Breast cancer is the most common invasive tumor disease in women on a global scale. According to estimates by the World Health Organization (WHO), there are more than 1 million new incidents of breast cancer worldwide per year. Various factors are believed to contribute to the occurrence of breast cancer, such as a genetic predisposition, hormonal factors, lifestyle habits, such as smoking, alcohol consumption, and lack of exercise. However, the exact etiology of breast cancer is not completely understood. Likewise it is also not possible to accurately predict the further course of the disease, once a patient has been diagnosed with breast cancer, nor is it possible to accurately predict what treatment should best be used for the individual patient.

BRIEF SUMMARY

The present invention provides for these and other similar needs. Accordingly, it was an object for the present invention to provide for markers that allow to predict the likelihood of a breast cancer patient's survival or the likelihood of a recurrence and/or metastasis of a breast cancer in a breast cancer patient. It was furthermore an object of the present invention to provide for a method for predicting the likelihood of a breast cancer patient's survival or the likelihood of the recurrence or metastasis of a breast cancer in a breast cancer patient.

BRIEF DESCRIPTION OF THE FIGURES

In the following, reference is made to the figures wherein.

BRIEF SUMMARY OF THE SEQUENCES

Figure 1:
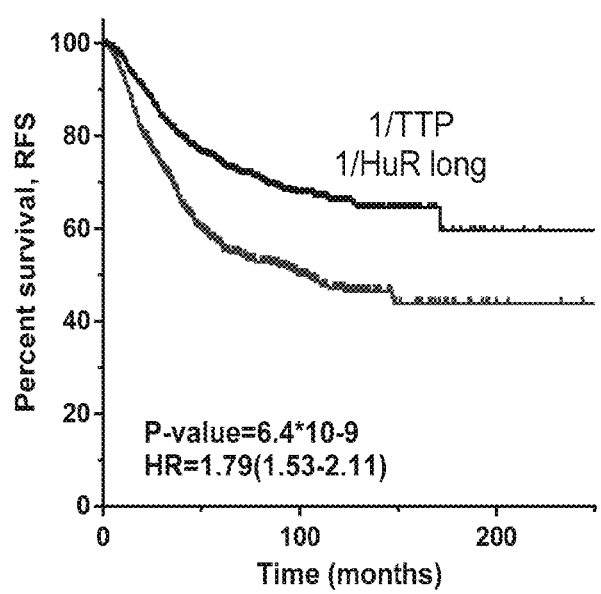
FIG. 1 shows the probability of survival of patients with an underexpression of ZFP36 and an underexpression of the 6 kb ELAVL1 variant. Because these species have a lower level of expression in cancer cells as opposed to normal cells, the plot uses inverted levels (1/x).
Figure 2:
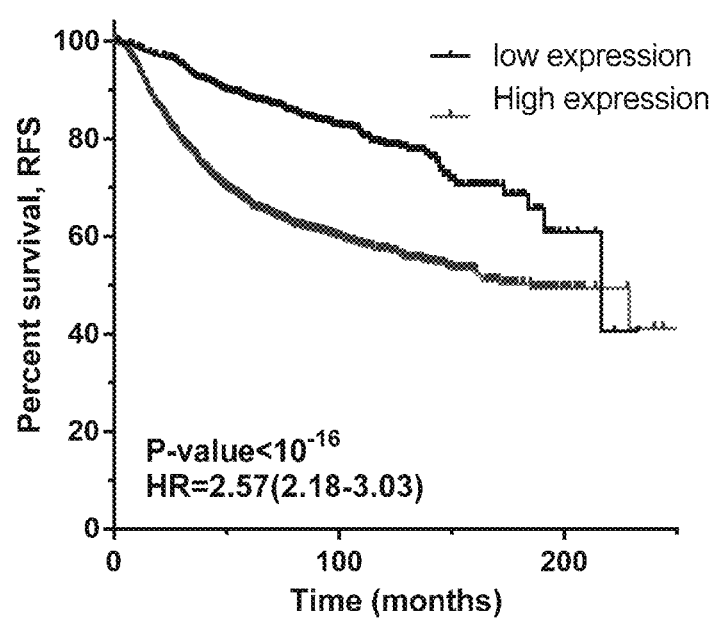
FIG. 2 shows the results of measurements of mRNA expression levels of BIRC5, NEK2, CCNB2, RRM2, TOP2A, and CENPE, as probability of survival over time.

SEQ ID NO: 1 is the sequence for the BIRC5 gene.
SEQ ID NO: 2 is the sequence for the CCNB2 gene.
SEQ ID NO: 3 is the sequence for the CDC6 gene.
SEQ ID NO: 4 is the sequence for the MMP13 gene.
SEQ ID NO: 5 is the sequence for the NEK2 gene.
SEQ ID NO: 6 is the sequence for the RRM2 gene.
SEQ ID NO: 7 is the sequence for the TOP2A gene.
SEQ ID NO: 8 is the sequence for the CENPE gene.
SEQ ID NO: 9 is the sequence for the MK167 gene.
SEQ ID NO: 10 is the sequence for the ZFP36 gene.
SEQ ID NO: 11 is the sequence for the ELAVL1 (6 kb variant) gene.
SEQ ID NO: 12 is the sequence for the ELAVL1 (1.5 kb variant) gene.
SEQ ID NO: 13 is the sequence for the ELAVL1 (2.7 kb variant) gene.
SEQ ID NO: 14 is the sequence for the ERBB2 gene.
SEQ ID NO: 15 is the sequence for the ESR1 gene.
SEQ ID NO: 16 is the sequence for the PGR gene.
SEQ ID NO: 17 is the sequence for the GAPDH gene.
SEQ ID NO: 18 is the sequence for the GUS gene.
SEQ ID NO: 19 is the sequence for the RPLPO gene.
SEQ ID NO: 20 is the sequence for the TUB gene.
SEQ ID NO: 21 is the sequence for the ACTB gene.
SEQ ID NO: 22 is the sequence for the 18SRNA gene.

DETAILED DESCRIPTION

All these objects are solved by a method for predicting the likelihood of a breast cancer patient's 5-year survival or the likelihood of recurrence of a breast cancer over a 5-year period in a breast cancer patient or the likelihood of a breast cancer patient's distant metastasis free survival (DMFS) over a 5-year period, said method comprising the steps:

measuring, in a tumor sample of said breast cancer patient, the mRNA expression levels of 5, 6, 7, 8 or all genes of a set of genes, said set of genes comprising, preferably consisting of BIRC5, CCNB2, CDC6, MMP13, NEK2, RRM2, TOP2A, CENPE, and, optionally, MKI67 comparing the measured mRNA expression levels from said tumor sample of said breast cancer patient with mRNA expression levels of the same genes in a non-tumor sample of a healthy individual or with mRNA expression levels of the same genes in a healthy, non-tumor sample of the same breast cancer patient, and either determining, based on such comparison, whether there is an overexpression of the respective genes in said tumor sample of said breast cancer patient, wherein an overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <70% and/or of a likelihood of recurrence of said breast cancer over 5-year period of >30% or of a likelihood of DMFS over a 5-year period of <70%, or determining, based on such comparison, whether there is a low overexpression, an intermediate overexpression or a high overexpression of the respective genes in said tumor sample of said breast cancer patient, wherein a low overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <95% and/or of a likelihood of recurrence of said breast cancer over 5-year period of >5% or of a likelihood of DMFS over a 5-year period of <95%, and wherein an intermediate overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <85% and/or of a likelihood of recurrence of said breast cancer over 5-year period of >15% or of a likelihood of DMFS over a 5-year period of <85%, and wherein a high overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <70% and/or of a likelihood of recurrence of said breast cancer over 5-year period of >30% or of a likelihood of DMFS over a 5-year period of <70%.

In one embodiment, said method additionally comprises measuring the mRNA expression levels of ZFP36 (TTP) and ELAVL1 (HuR) in said tumor sample of said patient, wherein, preferably, measuring ELAVL1 mRNA levels is a measuring of (i) all ELAVL1 variants or of (ii) a 1.5 kb and a 2.7 kb ELAVL1 variant or of (iii) a 6 kb ELAVL1 variant, and wherein a) an underexpression of ZFP36 or of the 6 kb ELAVL1 variant, or b) an overexpression of the 1.5 kb and 2.7 kb ELAVL1 variants, in comparison to the respective expression in a non-tumour sample of a healthy individual or in a healthy non-tumour sample of the same patient, or c) a ratio of ZFP36 mRNA expression: ELAVL1 1.5 and 2.7 kb variant mRNA expression <1 is indicative of a likelihood of 5-year survival of <70% and/or of a likelihood of recurrence over a 5-year period of >30% of said breast cancer.

In one embodiment, said method additionally comprises measuring the mRNA expression levels of ERBB2, ESR1 and PGR in said tumor sample of said breast cancer patient to classify the type of breast cancer of said breast cancer patient according to its expression or non-expression of ERBB2, ESR1 and/or PGR.

In one embodiment, said method additionally comprises measuring the mRNA expression levels of any suitable housekeeping gene(s) wherein, preferably said housekeeping gene(s) is (are) selected from GAPDH, GUS, RPLPO, TUB, ACTB and/or 18SRNA in said tumor sample of said breast cancer patient, wherein any measured mRNA expression levels of these housekeeping gene(s) serves for normalization purposes, and wherein the measured mRNA expression levels of said 5, 6, 7, 8 or all genes of said set of genes and optionally of any other gene, such as ZFP36, ELAVL1, ERBB2, ESR1 and/or PGR, are normalized against the measured mRNA expression level(s) of said housekeeping gene(s).

In one embodiment, said tumor sample of said breast cancer patient is a sample obtained from a breast cancer tumor of said breast cancer patient or is a body fluid sample of said breast cancer patient, preferably a body fluid containing exosomes, more preferably blood or urine In one embodiment, said method additionally comprises assigning a treatment by chemotherapy if said likelihood of 5-year survival has been determined as being <70% and/or if said likelihood of recurrence over a 5-year period has been determined as being >30%, and/or assigning a treatment by hormones, if said likelihood of 5-year survival has been determined as being >70% and/or if said likelihood of recurrence over a 5-year period has been determined as being <30%.

In one embodiment, measurement of mRNA expression levels occurs by any of hybridization, preferably on a microarray, next-generation sequencing, in-situ hybridization, RT-PCR, preferably quantitative RT-PCR, flow cytometry, immunohistochemistry and any combination of the foregoing.

In one embodiment, measuring mRNA expression levels of said genes of said set of genes is done using a corresponding set of probes which are complementary to said genes or to the respective mRNAs of said genes, wherein, preferably, said probes or primers consist of 10-100 adjacent nucleotides, wherein more preferably said probes or primers are cDNA, cRNA, PNA, or DNA oligonucleotides.

In one embodiment, expression of the mRNAs of each gene in said tumor sample is an overexpression, if said mRNA expression levels in said tumor sample are at least 1.5-fold, preferably at least two-fold the mRNA expression levels of the same genes in a non-tumor sample of a healthy individual or in a healthy, non-tumor sample of the same patient.

In one embodiment, the genes have sequences designated as the following SEQ ID NOs:

| | |
|---|---|
| BIRC5 | SEQ ID NO: 1 |
| CCNB2 | SEQ ID NO: 2 |

-continued

| | |
|---|---|
| CDC6 | SEQ ID NO: 3 |
| MMP13 | SEQ ID NO: 4 |
| NEK2 | SEQ ID NO: 5 |
| RRM2 | SEQ ID NO: 6 |
| TOP2A | SEQ ID NO: 7 |
| CENPE | SEQ ID NO: 8 |
| MKI67 | SEQ ID NO: 9 |
| ZFP36 | SEQ ID NO: 10 |
| ELAVL1 (6 kb variant) | SEQ ID NO: 11 |
| ELAVL1 (1.5 kb variant) | SEQ ID NO: 12 |
| ELAVL1 (2.7 kb variant) | SEQ ID NO: 13 |
| ERBB2 | SEQ ID NO: 14 |
| ESR1 | SEQ ID NO: 15 |
| PGR | SEQ ID NO: 16 |
| GAPDH | SEQ ID NO: 17 |
| GUS | SEQ ID NO: 18 |
| RPLPO | SEQ ID NO: 19 |
| TUB | SEQ ID NO: 20 |
| ACTB | SEQ ID NO: 21 |
| 18SRNA | SEQ ID NO: 22 |

In one embodiment, measuring the mRNA expression levels of 5 genes of said set of genes is a measuring of the expression levels of BIRC5, CCNB2, NEK2, RRM2, and TOP2A, and wherein measuring the mRNA expression levels of 6 genes of said set of genes is a measuring of the expression levels of BIRC5, CCNB2, NEK2, RRM2, and TOP2A, and CENPE,
  wherein said measuring the mRNA expression levels of said 5 or 6 genes is optionally in combination with measuring the mRNA expression levels of ZFP36 (TTP) and ELAVL1 (HuR) in said tumor sample of said patient, wherein, preferably, measuring ELAVL1 mRNA levels is a measuring of (i) all ELAVL1 variants or of (ii) said 1.5 kb and said 2.7 kb ELAVL1 variant or of (iii) said 6 kb ELAVL1 variant.

In one embodiment, said patient is a breast cancer patient who is either (i) ESR1-positive or ERBB2-negative, (ii) ESR1-positive and ERBB2-negative, (iii) ESR1-positive and/or PGR-positive and/or ERBB2-positive ("Luminal B breast cancer"), or (iv) ESR1-positive and/or PGR-positive, ERBB2-negative ("Luminal A breast cancer"), wherein optionally said patient is any of (i)-(iv) and said patient's lymph nodes are not affected by said breast cancer ("lymph node-negative").

In one embodiment, said patient is a patient whose lymph nodes are not affected by said breast cancer ("lymph node-negative" patient).

In a further aspect the present invention also relates to a kit for use in a method of the present invention, said kit comprising, preferably consisting of probes for determining the expression of mRNAs of 5, 6, 7, 8 or all genes of a set of genes, and said kit optionally also consisting of probes for determining expression of mRNAs of each of ZFP36 and ELAVL1, and/or of ERBB2, ESR1 and PGR, and/or of GAPDH, GUS, RPLPO, TUB, ACTB and 18SRNA, and of means for detecting a hybridization event between any of said probes and a corresponding mRNA in a sample of a patient,
said set of genes consisting of
  BIRC5, CCNB2, CDC6, MMP13, NEK2, RRM2, TOP2A, CENPE, and optionally MKI67, said probes being for determining the expression of mRNAs of each of said set in a sample of a patient having breast cancer or being diagnosed with breast cancer.

In one embodiment, the kit according to the present invention additionally comprises, preferably additionally also consists of probes for determining expression of mRNAs of each of ZFP36 and ELAVL1.

In one embodiment, the kit according to the present invention additionally comprises, preferably additionally also consists of probes for determining expression of mRNAs of ERBB2, ESR1 and PGR.

In one embodiment, the kit according to the present invention additionally comprises, preferably additionally also consists of probes for determining expression of mRNAs of at least one housekeeping gene, preferably selected from GAPDH, GUS, RPLPO, TUB, ACTB and 18SRNA.

In one embodiment, the kit according to the present invention additionally comprises, preferably additionally also consists of means for detecting a hybridization event between any of said probes and an mRNA in a sample of a patient.

In one embodiment, said probes are complementary to the mRNA sequences of said genes and consist of 10-100 adjacent nucleotides which are complementary to said sequences, wherein said probes are preferably any suitable nucleic acid probe for hybridization and/or quantification including but not limited to DNA oligonucleotides, cDNA, cRNA, PNA, or others.

In a preferred embodiment, the measuring of mRNA expression levels is done by amplification using appropriate RT-PCR primers (or -probes, such terms being used interchangeably herein) and subsequent quantification.

In one embodiment, for calculation purposes, the mRNA levels are sometimes expressed as weighted means, using a weighting factor, preferably as outlined in Example 1.

The present inventors have surprisingly found that a specific combination of 5, 6, 7, 8 or all genes of a set of genes which consists of the following genes: BIRC5, CCNB2, CDC6, MMP13, NEK2, RRM2, TOP2A, CENP, and, optionally, MKI67, is particularly useful for predicting the likelihood of a breast cancer patient's survival or the likelihood of a recurrence of a breast cancer in a breast cancer patient. Preferably, such survival is a 5-year survival.

In one embodiment, the recurrence of a breast cancer is a 5-year recurrence, i. e. a reappearance of the breast cancer within an interval of 5 years. The present inventors have identified a set of nine genes which are particularly suitable as prognostic markers and which are particularly suitable for predicting the likelihood of survival or of recurrence of a breast cancer. The inventors have found that if one takes a combination of five genes or six genes or seven genes or eight genes or nine genes, i. e. all of the genes of such gene set and measures mRNA-levels thereof in a tumor sample of a breast cancer patient, it is possible to use such mRNA-level measurements for predicting the likelihood of survival of said breast cancer patient. In one embodiment, a combination of five genes of the set of genes consists of BIRC5, CCNB2, NEK2, RRM2, and TOP2A. In one embodiment, a combination of six genes of the set of genes consists of BIRC5, CCNB2, NEK2, RRM2, TOP2A, and CENPE. In one embodiment, the set of genes consists of the five genes BIRC5, CCNB2, NEK2, RRM2, and TOP2A. In another embodiment, the set of genes consists of the six genes BIRC5, CCNB2, NEK2, RRM2, TOP2A, and CENPE.

The term "measuring the mRNA expression levels of x genes", with x being an integer number selected from 5, 6, 7, 8 or 9, is meant to refer to a measurement of the mRNA expression levels of these x genes and not of x−1 genes or x+1 genes. Hence in a measurement of the mRNA levels of 5 genes, the mRNA levels of precisely 5 genes are measured, in a measurement of the mRNA levels of 6 genes, the mRNA levels of precisely 6 genes are measured, in a measurement of the mRNA levels of 7 genes, the mRNA levels of precisely 7 genes are measured, in a measurement of the mRNA levels of 8 genes, the mRNA levels of precisely 8 genes are measured, and in a measurement of the mRNA levels of 9 genes, the mRNA levels of precisely 9 genes are measured (notwithstanding an optional measurement of any of the following group of expressions: (i) expression of genes pertaining to a classification of the breast cancer in terms of receptor expression and (ii) ZFP36/ELAVL1 expression and (iii) housekeeping gene expression. The term "housekeeping gene" is meant to refer to any gene that is constitutively expressed in a cell and required for maintaining basic cellular function; typically a housekeeping gene is expressed irrespective of whether a cell is in a normal healthy or a pathological state. Preferred examples of housekeeping genes as used herein are GAPDH, GUS, RPLPO, TUB, ACTB and 18SRNA.

In one embodiment, for measuring the mRNA-expression levels of each gene of said set of genes, one uses a corresponding set of probes or a corresponding set of primers which are complementary to said genes or to the mRNA of the respective genes. The terms "probes" and "primers" as used herein are used interchangeable. In one embodiment, said probes or said primers consist of 10-100 adjacent nucleotides. In one embodiment, said probes or said primers are complementary to said genes, in another embodiment, said probes or said primers are complementary to mRNAs of said genes. In one embodiment, said probes or said primers are complementary to the sense strand of the respective gene(s), in another embodiment, said probes or said primers are complementary to the antisense-strand of the respective gene(s). In a preferred embodiment, said probes or said primers are complementary to the mRNAs of the respective gene(s), and are cDNA.

The present inventors have surprisingly found that an overexpression of mRNA of the 5, 6, 7, 8 or 9 of the aforementioned genes, in a sample of a breast cancer patient, in comparison to the mRNA expression levels of the respective same gene(s) in a sample of a healthy individual or a healthy, non-tumor sample of the same (breast cancer) patient is indicative of a likelihood of a 5-year survival of <70%. Such an overexpression is or may also be indicative of a likelihood of a 5-year recurrence of breast cancer of >30%. Moreover, such an overexpression is or may also be indicative of a distant metastasis free survival over 5 years of <70%.

The term "metastasis-free survival" (MFS) or "distant metastasis-free survival" (DMFS) refers to the period after a curative treatment, when no disease can be detected, until a metastasis is detected. In the case of "distant metastasis-free survival", such metastasis is detected in a tissue which is not breast tissue.

The term "healthy individual" as used herein is meant to refer to an individual not affected by breast cancer. The term "healthy sample" or "non-tumor sample" is meant to refer to a sample (e.g. of tissue) which is not affected by breast cancer. The term "tumor sample" is meant to refer to a sample (e.g. tissue) which is affected by breast cancer.

The term "overexpression", as used herein, refers to an overexpression of gene(s) in the tumor sample of said patient in comparison to the expression of the same gene(s) in a non-tumor sample of the same patient or a non-tumor sample of a healthy individual. A measured mRNA expression level of said gene(s) in said tumor sample represents an "overexpression" over the measured mRNA expression levels of said gene(s) in a non-tumor sample of a healthy individual or in a healthy, non-tumor sample of the same breast cancer patient if the measured mRNA expression level(s) of said gene(s) in said tumor sample is at least 1.2-fold, preferably at least 1.5-fold, more preferably at least 2-fold the mRNA expression level(s) of the respective gene(s) in a non-tumor sample of a healthy individual or in a non-tumor sample of the same patient. An "overexpression" of the mRNA of a gene in a tumor sample, as used herein, is meant to refer to an increase of expression to an expression level which is at least 1.2-fold, preferably at least 1.5-fold, preferably at least 2-fold the expression level of the same mRNA in a healthy sample ("normal" expression level or "reference" expression level). An increase of expression to a level of 1-fold to 1.2-fold the normal level is herein also sometimes referred to as "low overexpression" or "low expression". An increase of expression to a level of 1.2- to 2-fold, preferably 1.5- to 2-fold, the normal level is herein also sometimes referred to as "intermediate overexpression" or "intermediate expression", and an increase to a level of more than 2-fold the normal level is herein also referred to as "high overexpression". Such "low overexpression", "intermediate overexpression" and "high overexpression" may be of importance if a patient cohort is classified into more than two risk groups, e.g. three risk groups. Such a stratification into more than two groups may give a better risk prediction.

Accordingly, in one embodiment, the method for predicting the likelihood of a breast cancer patient's 5-year survival or the likelihood of recurrence of a breast cancer over a 5-year period in a breast cancer patient or the likelihood of a breast cancer patient's distant metastasis free survival (DMFS) over a 5-year period comprises the following steps:

measuring, in a tumor sample of said breast cancer patient, the mRNA expression levels of 5, 6, 7, 8 or all genes of a set of genes, said set of genes comprising, preferably consisting of BIRC5, CCNB2, CDC6, MMP13, NEK2, RRM2, TOP2A, CENPE, and, optionally, MKI67 comparing the measured mRNA expression levels from said tumor sample of said breast cancer patient with mRNA expression levels of the same genes in a non-tumor sample of a healthy individual or with mRNA expression levels of the same genes in a healthy, non-tumor sample of the same breast cancer patient, and determining, based on such comparison, whether there is a low overexpression, an intermediate overexpression or a high overexpression of the respective genes in said tumor sample of said breast cancer patient, wherein a low overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <95% and/or of a likelihood of recurrence of said breast cancer over 5-year period of >5% or of a likelihood of DMFS over a 5-year period of <95%, and wherein an intermediate overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <85% and/or of a likelihood of recurrence of said breast cancer over 5-year period of >15% or of a likelihood of DMFS over a 5-year period of <85%, and wherein a high overexpression of the mRNAs of each gene in said tumor sample of said patient in comparison to the mRNA expression levels of the same genes of said healthy individual or in said healthy, non-tumor sample of the same breast cancer patient is indicative of a likelihood of 5-year survival of <70% and/or of a likelihood of recurrence of said breast cancer over 5-year period of >30% or of a likelihood of DMFS over a 5-year period of <70%.

In such an embodiment, the method preferably additionally comprises
assigning a treatment by chemotherapy if said likelihood of 5-year survival has been determined as being <70% and/or if said likelihood of recurrence over a 5-year period has been determined as being >30%, and/or
assigning a treatment by hormones, if said likelihood of 5-year survival has been determined as being <85% and/or if said likelihood of recurrence over a 5-year period has been determined as being <15%, and/or
assigning no treatment, if said likelihood of 5-year survival has been determined as being <95% and/or if said likelihood of recurrence over a 5-year period has been determined as being <5%.

The term "underexpression", as used herein, refers to a lower expression of gene(s) in the tumor sample of said patient in comparison to the expression of the same gene(s) in a non-tumor sample of the same patient or a non-tumor sample of a healthy individual. A measured mRNA expression level of said gene(s) in said tumor sample represents an "underexpression" over the measured mRNA expression levels of said gene(s) in a non-tumor sample of a healthy individual or in a healthy, non-tumor sample of the same breast cancer patient if the measured mRNA expression level(s) of said gene(s) in said tumor sample is less than the mRNA expression level(s) of the respective gene(s) in a non-tumor sample of a healthy individual or in a non-tumor sample of the same patient.

The term "recurrence", as used herein is meant to refer to the reappearance of breast cancer within a defined period of time. For example a 5-year recurrence refers to a reappearance of breast cancer in a patient within 5 years after a curative treatment when no disease can be detected.

The term "5-year survival" refers to a period of survival for five years after a timepoint at which timepoint no disease could be detected (e.g. because of a curative treatment that had taken place or because of a spontaneous disappearance of the breast cancer). The term "relapse-free survival" (also abbreviated as "RFS") refers to a survival period measured over time in which period no disease can be detected.

In one embodiment, the measurements of mRNA expression levels of the 5, 6, 7, 8 or all of the genes of said set of genes is combined with measurements of mRNA expression levels of ZFP36 (also referred to as "zinc finger protein 36 homolog" or "tristetraproline" or "TTP") and measurement of mRNA expression levels of ELAVL1 (also referred to as "ELAV-like protein 1" or "human antigen R" or "HuR"). The inventors have surprisingly found that ZFP36 mRNA expression levels are generally 3- to 6-fold decreased in breast cancer tissue in comparison to normal, i.e. healthy, tissues, i.e., they are only $\frac{1}{3}^{rd}$ to $\frac{1}{6}^{th}$ of the expression in healthy tissues. Moreover, the inventors found that ELAV1 mRNA is overexpressed in breast cancer tissue of a breast cancer patient, if one looks at a polyadenylation variant of 2.7 kb of ELAVL1. ELAVL1 has three variants namely a 1.5 kb variant, a 2.7 kb variant which is the most abundant form, and another, less abundant, 6 kb variant. The 1.5 and 2.7 kb variants mRNA is/are overexpressed in breast cancer patients with a poor prognosis, whereas the longer (6 kb) variant is under-expressed in breast cancer patients with a poor prognosis compared with normal/healthy tissues.

A combination of the measurements of the mRNA expression levels of the above-mentioned 5, 6, 7, 8 or 9 genes from the above-mentioned set of genes, with a measurement of the mRNA expression levels of ZFP36 and ELAVL1 even improves the prognostic value of such measurements. Because, in breast cancer tissues, ZFP36 is under-expressed, as is the 6 kb variant of ELAVL1, for calculation purposes, in embodiments of the present invention, one typically works with the reciprocal values of these under expressed genes (or mRNAs). If, instead, one looks at the expression of the shorter 1.5 or 2.7 kb variants (which are overexpressed in breast cancer tissue in comparison with normal tissue), for calculation purposes, in embodiments of the present invention, one uses the measured mRNA levels as such. A combination of the aforementioned measurements of the mRNA levels, i. e. of the expression of the 5, 6, 7, 8 or 9 genes, together with measurements of the mRNAs of ZFP36 and ELAVL1, can increase the accuracy of the prognosis even further. In one embodiment, the method according to the present invention additionally comprises a measuring of the mRNA expression levels of ZFP36 (TTP) and the mRNA expression levels of ELAVL1 (HuR) in said tumor sample of said patient, wherein measuring ELAVL1 mRNA levels is a measuring of the 1.5 kb, the 2.7 kb and/or the 6 kb variant of ELAVL1. Because, in breast cancer patients with a poor prognosis of 5-year survival, ZFP36 is typically under-expressed and ELAVL1 is over-expressed (as far as the expression of the 1.5 and 2.7 kb variants are concerned), a ratio of such expression levels being <1 is indicative of a likelihood of 5-year survival <70%.

In one embodiment, the method additionally comprises measuring the mRNA expression levels of the ERBB2, ESR1 and PGR in said tumor sample of said breast cancer patient to classify the type of breast cancer of said breast cancer patient according to its expression or non-expression of ERBB2, ESR 1 and/or PGR. The term "ERBB2", as used herein, is meant to refer to the human epidermal growth factor receptor 2, also referred to as "HER2/neu". The term "ESR1", as used herein, is meant to refer to estrogen receptor 1.

The term "PGR", as used herein, is meant to refer to the progesterone receptor.

A person skilled in the art knows how to measure mRNA expression and is familiar with techniques for that purpose, such as hybridization, preferably on a microarray, next-generation sequencing, in-situ hybridization, RT-PCR, flow cytometry, immunohistochemistry etc. (see for example "Molecular Cell Biology", Lodish et al. 2000, $4^{th}$ ed., eds. W.H. Freeman). A person skilled in the art is also familiar with techniques to detect hybridization events (ibid.; Alberts et al. "Molecular Biology of the Cell", 2014, $6^{th}$ ed., Garland Science), as well as with methods for the design and generation of suitable primers or probes. (ibid.)

Moreover, reference is made to the following examples which are given to illustrate, not to limit the present invention.

EXAMPLES

Example 1: Methodologies

Cancer Patient Data

The Oncomine web-based data mining platform (www.oncomine.com) was used to mine data from The Cancer Genome Atlas (TCGA) and METABRIC databases (Curtis C, Shah S P, Chin S F, Turashvili G, Rueda O M, Dunning M J, et al. The genomic and transcriptomic architecture of 2,000 breast tumours reveals novel subgroups. Nature. 2012; 486:346-52.). Gene expression levels for 389 and 1556 invasive ductal breast cancer samples were downloaded for TCGA and METABRIC datasets, respectively, along with the 61 and 144 corresponding matched normal samples. Cancer upregulated genes were sought using a threshold of 1.7-fold increase in mRNA expression and Q<0.0001. Intersecting 2396 upregulated genes with 3658 genes from the ARE database (ARED) allowed the identification of the over-expressed AU-rich element-containing genes. Log 2 median-centered intensity ratios were used. Other cancer datasets were used and extracted through Oncomine and Nextbio portals.

Regression and Statistical Analysis

Linear regression and Pearson pairwise correlations between the expression values of upregulated ARE genes and TTP/HuR ratios were determined for the TCGA data using GraphPad Prism, version 6 for Windows (GraphPad Software, La Jolla, Calif.). Multiple regression models (JMP®, Version 10, SAS Institute Inc., Cary, N.C., 1989-2007) were used to fit TTP, HuR and TTP/HuR mRNA ratio expressions with an upregulated ARE-gene list (414) and ARE-gene cluster set (23 genes). Concordance correlation was used to assess the goodness of fit (Lin 1989, *Biometrics*). Goodness-of-fit tests for TTP, HuR, and TTP/HuR were performed by comparing actual values to those predicted by the fit model using the standard least square test.

Weighted means were calculated by multiplying the mean by its weight for each gene. This was achieved by computing the function $$\bar{x} = \left(\frac{\Sigma w_i * \text{mean}(i)}{\Sigma w_i}\right), \text{ -here } \left(w_i = \frac{1}{(SE_i)^2}\right)$$

and mean $_{(i)}$ is the average of the gene expression and $(SE_i)$ is the standard error for each gene.

All data are presented as mean±standard error of the mean (SEM). Unpaired Student's t-test was used to analyze statistical difference when comparing two datasets, whereas one-way ANOVA was used for determining statistical significance for three or more datasets. The results with $p<0.05$ were considered significant and indicated as asterisks. Statistical analyses were performed using GraphPad Prism and JMP®, Version 10 as well as SPSS.

Clustering and Functional Annotation

Clustering analysis of the resulting genes was performed based on normal mixture modeling to extract the ARE-mRNAs with the most significant negative correlation with the TTP/HuR ratio. The Akaike Information Criterion (AIC) value was used as an indicator of goodness of fit (smallest AIC). The over-expressed ARE-mRNAs were then analyzed using the AIC value and Johnson's transformation, which resulted in a best-fit normal mixture. Supervised hierarchical clustering and heat map visualization of gene expression data were performed using Gene-E (Broad Institute). Functional enrichment was performed using several web-based resources, including GEneSeT analysis, Database for Annotation, Visualization and Integrated Discovery (DAVID), and STRING protein-protein interaction resource.

Cell Culture

The normal-like mammary cell lines MCF10A and MCF12A, and the breast tumorigenic cell lines MCF-7 and MDA-MB-231, and the HEK293 cells were obtained from ATCC (Rockville, Md., USA). MCF10A and MCF12A were cultured in Dulbecco's Modified Eagle Medium: F12 (DMEM: F12, Life Technologies, Grand Island, N.Y., USA) fortified with HuMEC supplement (Gibco, Thermofisher, Grand Island, N.Y.), 10% FBS and antibiotics. MDA-MB-231, MCF-7, and HEK293 cells were grown in DMEM supplemented with 10% FBS and antibiotics. Tet-On Advanced HEK293 cells were obtained from ClonTech (Mountain View, Calif., USA) and were cultured in DMEM supplemented with 10% Tet-System Approved FBS (ClonTech), 100 ug/mL G418 (Sigma), and 5% penicillin-streptomycin (Invitrogen, Carlsbad, Calif., USA).

Quantitative Real-Time PCR

Total RNA was extracted (TRI reagent, Sigma) and reverse transcribed as described previously (Al-Souhibani N, Al-Ghamdi M, Al-Ahmadi W, Khabar K S A. Posttranscriptional control of the chemokine receptor CXCR4 expression in cancer cells. Carcinogenesis. 2014; 35:1983-92). Quantitative real-time PCR (qPCR) was performed in multiplex using FAM-labeled Taqman primer and probe sets (Applied Biosystems, Foster City, Calif., USA) for the following: human BIRC5, CCNB2, CDC6, MMP13, NEK2, RRM2, TOP2A, CENPE, and, MK167, and optionally normalized to VIC-labeled human GAPDH as the endogenous control. Samples were amplified in triplicate in a CFX96 cycler (Bio-Rad), and quantification of relative expression was performed using the $\Delta\Delta Ct$ method.

Survival Analysis

The Kaplan-Meier survival analyses were performed using the Kaplan-Meier plotter portal, a manually curated and comprehensive dataset for survival analysis that covers 54,675 genes in 4,142 breast cancer patients (Gyorffy B, Lanczky A, Eklund A C, Denkert C, Budczies J, Li Q, et al. An online survival analysis tool to rapidly assess the effect of 22,277 genes on breast cancer prognosis using microarray data of 1,809 patients. Breast Cancer Res Treat. 2010; 123:725-31.). The database was built from the gene expression and survival data extracted from the European Genome-Phenome Archive (EGA) and the Gene Expression Omnibus (GEO) repositories. Overall survival (OS), recurrence-free survival (RFS), and distant metastasis free survival (DMFS) were determined using gene cluster stratification. In addition, survival analysis in the METABRIC and TCGA RNA sequence databases was performed separately. Associations between gene expression and patient survival were assessed by the Kaplan-Meier method (log-rank test, Graphpad 6.0). Kaplan-Meier analysis was performed as described previously (Mihaly Z, Kormos M, Lanczky A, Dank M, Budczies J, Szasz M A, et al. A meta-analysis of gene expression-based biomarkers predicting outcome after tamoxifen treatment in breast cancer. Breast Cancer Res Treat. 2013; 140:219-32.). The JETSET best probe set was selected in case multiple probe sets measured the same gene to ensure the optimal probe set for each gene. Hazard ratios and p-values were determined by Cox proportional hazards regression.

Example 2: Results

Associations between gene expression and patient survival were assessed by the Kaplan-Meier method (log-rank test). Survival data in association with gene expression data were collected from several public databases aided by web portals.

These resources include combined databases such as TCGA (tumor cancer genome atlas), METABRIC breast cancer data, and many others.

In all the examples, the proportion of patients surviving were plotted against time in months using two sets of groups reflecting two or more populations that are associated with two or more of relative gene expression, e.g., high and low, or high, intermediate and low. The median can be used as a cut-off between low and high in these plots. Any other cut-off statistical method that determine best percentile can be used. Values of gene expression are generally normalized to a housekeeping gene.

FIG. 1

Patient samples with gene expression data using the mean for inverted levels of ZFP36 and ELAVL1 6 kb were stratified into low and high expression based on the median. The proportions of patients surviving (Relapse-free survival, RFS) in each of this group were plotted against time. Hazard ratio (risk) with p-values are shown in the graph. Patients with high mean inverted levels of TTP and ELAVL1 6 kb mRNA had a poor survival outcome, while those with low inverted better survival outcome.

FIG. 2

Patient samples with gene expression data using the mean for the mRNA expression levels of BIRC5, NEK2, CCNB2, RRM2, TOP2A, and CENPE were stratified into low and high expression based on the median. These mRNAs were chosen by the inventors because the inventors found that they bind to RNA-binding proteins, ZFP36 and ELAVL1 and are regulated by them and also over-expressed in cancer. The proportions of patients surviving (Relapse-free survival, RFS) in each of this group were plotted against time. Hazard ratio (risk) (HR) with p-values are shown in the graph. Patients with high median levels of expression had a poor survival outcome, while those with low median levels of expression had better survival outcome. More specifically, as can be seen from the figure, patients with an overexpression had a likelihood of 5-year survival of <70%.

FIG. 3

Patient samples with gene expression data using the mean for the mRNA expression levels of BIRC5, NEK2, CCNB2, RRM2, TOP2A, and CENPE were stratified into low and high expression based on the median. The proportions of patients surviving (distant metastasis free survival (DMFS) in each of this group were plotted against time. Hazard ratio (risk) with p-values are shown in the graph. Patients with high median levels of expression had a poor survival outcome, while those with low had better survival outcome. More specifically, as can be seen from the figure, patients with an overexpression had a likelihood of DMFS over a 5-year period of <70%. It appears that the classification predicts better in case of patients who are lymph-node negative (i.e., their lymph nodes are unaffected by the breast cancer) and ER-positive.

FIG. 4

Patient samples with gene expression data using the mean for the mRNA expression levels of BIRC5, NEK2, CCNB2, RRM2, TOP2A, and CENPE were stratified into three quantile groups low, intermediate, and high expression. The proportions of patients surviving (distant metastasis free survival (DMFS) in each of this group were plotted against time. Hazard ratio (risk) with p-values are shown in the graph. Patients with high median levels of expression had a poor survival outcome, while those with low median levels had better survival outcome. More specifically, as can be seen from the figure, patients with a high overexpression had a likelihood of DMFS over a 5-year period of <70%, patients with an intermediate overexpression had a likelihood of DMFS over a 5-year period of <85%, and patients with a low overexpression had a likelihood of DMFS over a 5-year period of <95%. It appears that the classification predicts better in case of patients who are lymph-node negative (i.e., their lymph nodes are unaffected by the breast cancer) and ESR1-positive.

Figure 3:
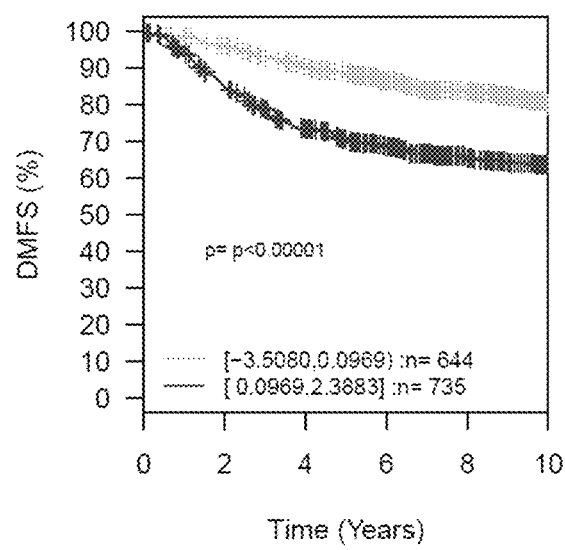
FIGS. 3 and 4 show a risk stratification of the same measurements when looking at the distant metastasis free survival (DMFS) in 2 (FIG. 3) and 3 groups (FIG. 4) as probability over time.
Figure 4:
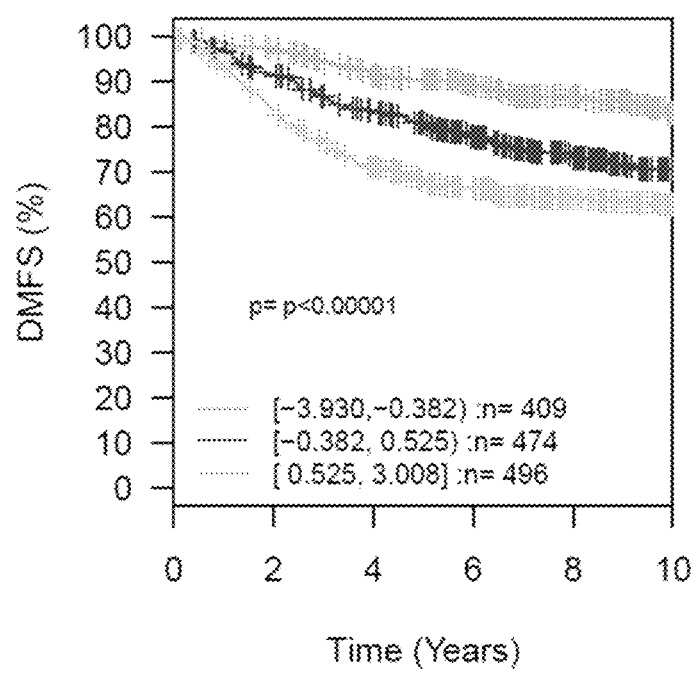
Figure 5:
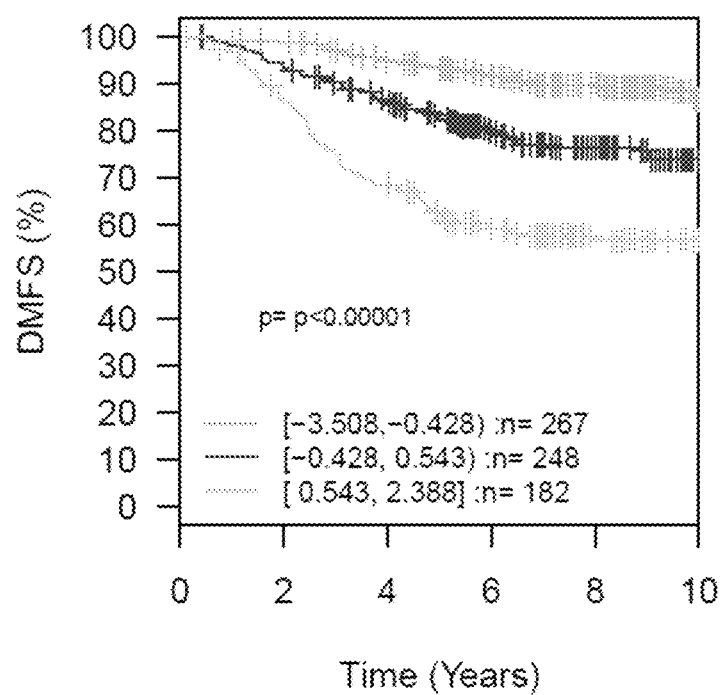
FIG. 5 shows risk stratification of the same measurements when looking at the distant metastasis free survival (DMFS) in 3 groups taking into account also the lymph node status, ESR1 expression and ERBB2 expression as probability of DMFS over time.

The results of FIGS. 3 and 4 can be represented in the following Table 1:

TABLE 1

| | P value 3 groups | p VALUE 2 groups |
|---|---|---|
| ALL | e−17 | e−14 |
| LYMPH NODE-NEGATIVE | e−17 | e−14 |
| LYMPH NODE-POSITIVE | 0.02 | Ns |
| ESR1-POSTIVE | e−15 | e−12 |
| ESR1-NEGATIVE | ns | ns |

"ns" means "not significant".

FIG. 5

Samples of patients who are both lymph-node negative and estrogen-receptor-positive (ESR1) were used. Gene expression data using the mean for the mRNA expression levels of BIRC5, NEK2, CCNB2, RRM2, TOP2A, and CENPE were stratified into low and high expression based on the median. The proportions of patients surviving (distant metastasis free survival (DMFS) in each of this group were plotted against time. Hazard ratio (risk) with p-values are shown in the graph. Patients with the high median levels of the expression had a poor survival outcome, while those with low had better survival outcome. More specifically, as can be seen from the figure, patients with a high overexpression had a likelihood of DMFS over a 5-year period of <70%, patients with an intermediate overexpression had a likelihood of DMFS over a 5-year period of <85%, and patients with a low overexpression had a likelihood of DMFS over a 5-year period of <95%. It appears that the classification predicts better in case of patients who are lymph-node negative (i.e. their lymph nodes are unaffected by the breast cancer) and ER-positive.

FIG. 6

Patient samples with gene expression data using the mean for the mRNA expression levels of BIRC5, NEK2, CCNB2, RRM2, TOP2A, and CENPE, in combination with inverted levels of the mRNA expression of ZFP36 and ELAVL1 6 kb mRNA (long variant) were stratified into low and high expression based on the median. The proportions of patients surviving (RFS) in each of this group were plotted against time. Hazard ratio (risk) with p-values are shown in the graph. Patients with high median levels of expression had a poor survival outcome, while those with low had better survival outcome. More specifically, as can be seen from the figure, patients with an overexpression had a likelihood of 5-year survival of <70%, possibly even <60%.

Figure 6:
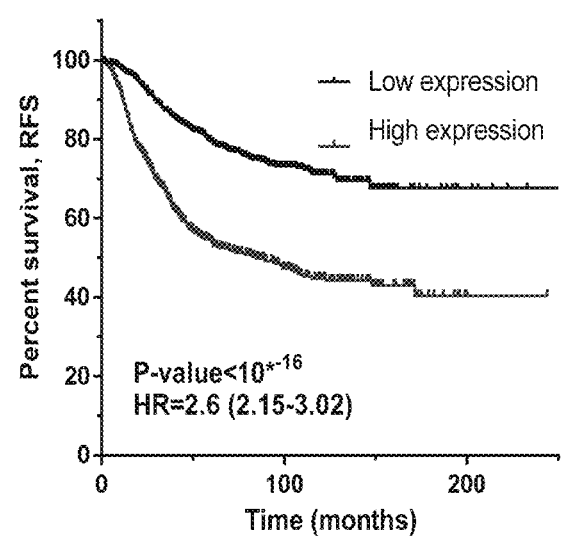
FIG. 6 shows the results of measurements of mRNA expression levels of BIRC5, NEK2, CCNB2, RRM2, TOP2A, and CENPE, in combination with the mRNA expression levels ZFP36/ELAVL1 (using the ELAVL1 6 kb variant) taking into account also the lymph node status, ESR1 expression and ERBB2 expression, as probability of survival over time.

The correlation of such poor survival outcome is mostly stronger with ESR1-positive status. The results of FIG. 6 can also be represented in the following Table 2.

TABLE 2

| | HR | p VALUE | No. |
|---|---|---|---|
| ALL | 2.6 | e−16 | |
| ERBB2-NEGATIVE | 2.7 | e−12 | 635 |
| ERBB2-POSITIVE | 0.83 | NS | 150 |
| LYMPH NODE-NEGATIVE | 2.22 | e−6 | 1118 |
| LYMPH NODE-POSITIVE | 2.32 | e−9 | 655 |
| ESR1-POSTIVE | 2.6 | e−9 | 1802 |
| ESR1-NEGATIVE | 1.4 | .02 | 313 |

"No." refers to the number of patients; "HR" is hazard ratio.

The invention claimed is:

1. A method for assigning treatment to a breast cancer patient based on the likelihood of said patient's relapse-free 5-year survival, said method comprising:
   a) measuring, in a tumor sample of said breast cancer patient and a non-tumor sample of a healthy subject or said breast cancer patient, mRNA expression levels of a set of genes consisting of CCNB2, NEK2, RRM2, TOP2A, and CENPE, and determining a median mRNA expression from the measured mRNA expression level for each gene in the tumor sample and a median mRNA expression from the measured mRNA expression level for each gene in the non-tumor sample,
   b) stratifying the patient into a low or high expression group based on the median mRNA expression of the set of genes in the tumor sample compared to the median mRNA expression of the set of genes in the non-tumor sample, wherein the low expression group has a likelihood of relapse-free 5-year survival of over 70% and the high expression group has a likelihood of relapse-free 5-year survival of less than 70%,
   c) assigning treatment with a hormone therapy to the patient if the patient has a likelihood of relapse-free 5-year survival of over 70% or assigning treatment with a chemotherapy to the patient if the patient has a likelihood of relapse-free 5-year survival of less than 70%, and
   d) carrying out said treatment with the hormone therapy to the patient if the patient has a likelihood of relapse-free 5-year survival of over 70%, or carrying out said treatment with the chemotherapy to the patient if the patient has a likelihood of relapse-free 5-year survival of less than 70%.

2. The method according to claim 1, wherein said tumor sample of said breast cancer patient is a sample obtained from a breast cancer tumor of said breast cancer patient or is a body fluid sample containing exosomes of said breast cancer patient.

3. The method according to claim 1, comprising measuring the mRNA expression levels by hybridization, next-generation sequencing, in-situ hybridization, RT-PCR flow cytometry, immunohistochemistry or any combination of the foregoing.

4. The method according to claim 1, comprising measuring the mRNA expression levels of said set of genes using a set of probes that is complementary to genes from the said set of genes or to the respective mRNAs of said genes.

5. The method according to claim 1, wherein the patient is in a high expression group when the median mRNA expression of the set of genes in tumor sample is at least 1.5 fold higher than the median mRNA expression of the same genes in the non-tumor sample of a healthy subject or the non-tumor sample of said breast cancer patient.

6. The method according to claim 1, wherein the genes have sequences designated as the following SEQ ID NOs:

| | |
|---|---|
| CCNB2 | SEQ ID NO: 2, |
| NEK2 | SEQ ID NO: 5, |
| RRM2 | SEQ ID NO: 6, |
| TOP2A | SEQ ID NO: 7, and |
| CENPE | SEQ ID NO: 8. |

7. The method according to claim 1, wherein said patient is either (i) ESR1-positive or ERBB2-negative, (ii) ESR1-positive and ERBB2-negative, (iii) ESR1-positive or PGR-positive or ERBB2-positive, (iv) ESR1-positive or PGR-positive, and ERBB2-negative, (v) ESR1-positive and PGR-positive and ERBB-2 positive, or (vi) ESR1-positive and PGR-positive and ERBB2-negative.

8. The method according to claim 1, wherein said patient is a patient whose lymph nodes are not affected by said breast cancer.

9. The method according to claim 1, wherein said patient is ESR1-positive or PGR-positive, and ERBB-2 positive.

10. The method according to claim 1, wherein said patient is ESR1-positive and PGR-positive and ERBB-2 positive.

* * * * *

SEQUENCE LISTING

<160> NUMBER OF SEQ ID NOS: 22

<210> SEQ ID NO 1
<211> LENGTH: 2724
<212> TYPE: DNA
<213> ORGANISM: Homo sapiens

<400> SEQUENCE: 1

| | | | | | |
|---|---|---|---|---|---|
| cccagaaggc | cgcgggggt | ggaccgccta | agagggcgtg | cgctcccgac | atgccccgcg | 60 |
| gcgcgccatt | aaccgccaga | tttgaatcgc | gggacccgtt | ggcagaggtg | gcggcggcgg | 120 |
| catgggtgcc | ccgacgttgc | ccctgcctg | gcagccctt | ctcaaggacc | accgcatctc | 180 |
| tacattcaag | aactggccct | tcttggaggg | ctgcgcctgc | accccggagc | ggatggccga | 240 |
| ggctggcttc | atccactgcc | ccactgagaa | cgagccagac | ttgcccagt | gtttcttctg | 300 |
| cttcaaggag | ctggaaggct | gggagccaga | tgacgacccc | attgggccgg | gcacggtggc | 360 |
| ttacgcctgt | aataccagca | cttgggagg | ccgaggcggg | cggatcacga | gagggaaca | 420 |
| taaaaagcat | tcgtccggtt | gcgctttcct | ttctgtcaag | aagcagtttg | aagaattaac | 480 |
| ccttggtgaa | tttttgaaac | tggacagaga | aagagccaag | aacaaaattg | caaggaaac | 540 |
| caacaataag | aagaaagaat | ttgaggaaac | tgcggagaaa | gtgcgccgtg | ccatcgagca | 600 |
| gctggctgcc | atggattgag | gcctctggcc | ggagctgcct | ggtcccagag | tggctgcacc | 660 |
| acttccaggg | tttattccct | ggtgccacca | gccttcctgt | gggccccta | gcaatgtctt | 720 |
| aggaaaggag | atcaacattt | tcaaattaga | tgtttcaact | gtgctcttgt | tttgtcttga | 780 |
| aagtggcacc | agaggtgctt | ctgcctgtgc | agcgggtgct | gctggtaaca | gtggctgctt | 840 |
| ctctctctct | ctctctttt | tgggggctca | ttttgctgt | tttgattccc | gggcttacca | 900 |
| ggtgagaagt | gagggaggaa | gaaggcagtg | tcccttttgc | tagagctgac | agctttgttc | 960 |
| gcgtgggcag | agccttccac | agtgaatgtg | tctggacctc | atgttgttga | ggctgtcaca | 1020 |
| gtcctgagtg | tggacttggc | aggtgcctgt | tgaatctgag | ctgcaggttc | cttatctgtc | 1080 |
| acacctgtgc | ctcctcagag | gacagttttt | ttgttgttgt | gtttttttgt | tttttttttt | 1140 |
| ttggtagatg | catgacttgt | gtgtgatgag | agaatggaga | cagagtccct | ggctcctcta | 1200 |
| ctgtttaaca | acatggcttt | cttattttgt | ttgaattgtt | aattcacaga | atagcacaaa | 1260 |
| ctacaattaa | aactaagcac | aaagccattc | taagtcattg | gggaaacggg | gtgaacttca | 1320 |
| ggtggatgag | gagacagaat | agagtgatag | gaagcgtctg | gcagatactc | cttttgccac | 1380 |
| tgctgtgtga | ttagacaggc | ccagtgagcc | gcggggcaca | tgctggccgc | tcctccctca | 1440 |
| gaaaaaggca | gtggcctaaa | tcctttttaa | atgacttggc | tcgatgctgt | gggggactgg | 1500 |
| ctgggctgct | gcaggccgtg | tgtctgtcag | cccaaccttc | acatctgtca | cgttctccac | 1560 |
| acggggaga | gacgcagtcc | gcccaggtcc | ccgctttctt | tggaggcagc | agctcccgca | 1620 |
| gggctgaagt | ctggcgtaag | atgatggatt | tgattcgccc | tcctccctgt | catagagctg | 1680 |
| cagggtggat | tgttacagct | tcgctggaaa | cctctggagg | tcatctcggc | tgttcctgag | 1740 |
| aaataaaaag | cctgtcattt | caaacactgc | tgtggaccct | actgggtttt | taaaatattg | 1800 |
| tcagttttc | atcgtcgtcc | ctagcctgcc | aacagccatc | tgcccagaca | gccgcagtga | 1860 |
| ggatgagcgt | cctggcagag | acgcagttgt | ctctgggcgc | ttgccagagc | cacgaacccc | 1920 |
| agacctgttt | gtatcatccg | ggctccttcc | gggcagaaac | aactgaaaat | gcacttcaga | 1980 |
| cccacttatt | tctgccacat | ctgagtcggc | ctgagataga | cttttccctc | taaactggga | 2040 |
| gaatatcaca | gtggtttttg | ttagcagaaa | atgcactcca | gcctctgtac | tcatctaagc | 2100 |

```
tgcttatttt tgatatttgt gtcagtctgt aaatggatac ttcactttaa taactgttgc    2160
ttagtaattg gctttgtaga gaagctggaa aaaaatggtt ttgtcttcaa ctcctttgca    2220
tgccaggcgg tgatgtggat ctcggcttct gtgagcctgt gctgtgggca gggctgagct    2280
ggagccgccc ctctcagccc gcctgccacg gcctttcctt aaaggccatc cttaaaacca    2340
gaccctcatg gctaccagca cctgaaagct tcctcgacat ctgttaataa agccgtaggc    2400
ccttgtctaa gtgcaaccgc ctagactttc tttcagatac atgtccacat gtccattttt    2460
caggttctct aagttggagt ggagtctggg aagggttgtg aatgaggctt ctgggctatg    2520
ggtgaggttc caatggcagg ttagagcccc tcgggccaac tgccatcctg gaaagtagag    2580
acagcagtgc ccgctgccca gaagagacca gcaagccaaa ctggagcccc cattgcaggc    2640
tgtcgccatg tggaaagagt aactcacaat tgccaataaa gtctcatgtg gttttatcta    2700
aaaaaaaaaa aaaaaaaaaa aaaa                                          2724

<210> SEQ ID NO 2
<211> LENGTH: 1566
<212> TYPE: DNA
<213> ORGANISM: Homo sapiens

<400> SEQUENCE: 2
gggccgccca atggggcgca agcgacgcgg tatttgaatc ctggaacaag gctacagcgt      60
cgaagatccc cagcgctgcg ggctcggaga gcagtcctaa cggcgcctcg tacgctagtg     120
tcctcccttt tcagtccgcg tccctccctg ggcggggctg gcactcttgc cttccccgtc     180
cctcatggcg ctgctccgac gcccgacggt gtccagtgat ttggagaata ttgacacagg     240
agttaattct aaagttaaga gtcatgtgac tattaggcga actgttttag aagaaattgg     300
aaatagagtt acaaccagag cagcacaagt agctaagaaa gctcagaaca ccaaagttcc     360
agttcaaccc accaaaacaa caaatgtcaa caaacaactg aaacctactg cttctgtcaa     420
accagtacag atggaaaagt tggctccaaa gggtccttct cccacacctg aggatgtctc     480
catgaaggaa gagaatctct gccaagcttt ttctgatgcc ttgctctgca aaatcgagga     540
cattgataac gaagattggg agaaccctca gctctgcagt gactacgtta aggatatcta     600
tcagtatctc aggcagctgg aggttttgca gtccataaac ccacatttct tagatggaag     660
agatataaat ggacgcatgc gtgccatcct agtggattgg ctggtacaag tccactccaa     720
gtttaggctt ctgcaggaga ctctgtacat gtgcgttggc attatggatc gattttttaca     780 ggttcagcca gtttcccgga agaagcttca attagttggg attactgctc tgctcttggc     840
ttccaagtat gaggagatgt tttctccaaa tattgaagac tttgtttaca tcacagacaa     900
tgcttatacc agttcccaaa tccgagaaat ggaaactcta attttgaaag aattgaaatt     960
tgagttgggt cgaccccttgc cactacactt cttaaggcga gcatcaaaag ccggggaggt    1020
tgatgttgaa cagcacactt tagccaagta tttgatggag ctgactctca tcgactatga    1080
tatggtgcat tatcatcctt ctaaggtagc agcagctgct tcctgcttgt ctcagaaggt    1140
tctaggacaa ggaaaatgga acttaaagca gcagtattac acaggataca cagagaatga    1200 agtattgaa gtcatgcagc acatggccaa gaatgtggtg aaagtaaatg aaaacttaac    1260
taaattcatc gccatcaaga ataagtatgc aagcagcaaa ctcctgaaga tcagcatgat    1320
ccctcagctg aactcaaaag ccgtcaaaga ccttgcctcc ccactgatag gaaggtccta    1380
ggctgccgtg gcccctgggg atgtgtgctt cattgtgccc tttttcttat tggtttagaa    1440
```

```
ctcttgattt tgtacatagt cctctggtct atctcatgaa acctcttctc agaccagttt      1500
tctaaacata tattgaggaa aaataaagcg attggttttt cttaaggtaa aaaaaaaaaa      1560
aaaaaa                                                                  1566

<210> SEQ ID NO 3
<211> LENGTH: 3053
<212> TYPE: DNA
<213> ORGANISM: Homo sapiens

<400> SEQUENCE: 3
gagcgcggct ggagtttgct gctgccgctg tgcagtttgt tcagggcctt gtggtggtga        60
gtccgagagg ctgcgtgtga gagacgtgag aaggatcctg cactgaggag gtggaaagaa       120
gaggattgct cgaggaggcc tggggtctgt gaggcagcgg agctgggtga aggctgcggg       180
ttccggcgag gcctgagctg tgctgtcgtc atgcctcaaa cccgatccca ggcacaggct       240
acaatcagtt ttccaaaaag gaagctgtct cgggcattga acaaagctaa aaactccagt       300
gatgccaaac tagaaccaac aaatgtccaa accgtaacct gttctcctcg tgtaaaagcc       360
ctgcctctca gccccaggaa acgtctgggc gatgacaacc tatgcaacac tccccattta       420
cctccttgtt ctccaccaaa gcaaggcaag aaagagaatg gtcccccctca ctcacataca      480 cttaagggac gaagattggt atttgacaat cagctgacaa ttaagtctcc tagcaaaaga       540
gaactagcca aagttcacca aaacaaaata ctttcttcag ttagaaaaag tcaagagatc       600
acaacaaatt ctgagcagag atgtccactg aagaaagaat ctgcatgtgt gagactattc       660
aagcaagaag gcacttgcta ccagcaagca agctggtcc tgaacacagc tgtcccagat        720
cggctgcctg ccagggaaag ggagatggat gtcatcagga atttcttgag ggaacacatc       780 tgtggggaaaa aagctggaag cctttacctt tctggtgctc ctggaactgg aaaaactgcc       840
tgcttaagcc ggattctgca agacctcaag aaggaactga aaggctttaa aactatcatg       900
ctgaattgca tgtccttgag gactgcccag gctgtattcc cagctattgc tcaggagatt       960
tgtcaggaag aggtatccag gccagctggg aaggacatga tgaggaaatt ggaaaaacat      1020
atgactgcag agaagggccc catgattgtg ttggtattgg acgagatgga tcaactggac      1080
agcaaaggcc aggatgtatt gtacacgcta tttgaatggc catggctaag caattctcac      1140
ttggtgctga ttggtattgc taatacccctg gatctcacag atagaattct acctaggctt      1200
caagctagag aaaaatgtaa gccacagctg ttgaacttcc caccttatac cagaaatcag      1260
atagtcacta ttttgcaaga tcgacttaat caggtatcta gagatcaggt tctggacaat      1320
gctgcagttc aattctgtgc ccgcaaagtc tctgctgttt caggagatgt tcgcaaagca      1380
ctggatgttt gcaggagagc tattgaaatt gtagagtcag atgtcaaaag ccagactatt      1440
ctcaaaccac tgtctgaatg taaatcacct tctgagcctc tgattcccaa gagggttggt      1500
cttattcaca tatcccaagt catctcagaa gttgatggta acaggatgac cttgagccaa      1560
gaaggagcac aagattcctt ccctcttcag cagaagatct tggtttgctc tttgatgctc      1620
ttgatcaggc agttgaaaat caaagaggtc actctgggga agttatatga agcctacagt      1680
aaagtctgtc gcaaacagca ggtggcggct gtggaccagt cagagtgttt gtcactttca      1740
gggctcttgg aagccagggg catttttagga ttaaagagaa acaaggaaac ccgtttgaca      1800
aaggtgtttt tcaagattga agagaaagaa atagaacatg ctctgaaaga taaagcttta      1860
attggaaata tcttagctac tggattgcct taaattcttc tcttacaccc cacccgaaag      1920
tattcagctg gcatttagag agctacagtc ttcattttag tgctttacac attcgggcct      1980
```

| | |
|---|---:|
| gaaaacaaat atgacctttt ttacttgaag ccaatgaatt ttaatctata gattctttaa | 2040 |
| tattagcaca gaataatatc tttgggtctt actatttta cccataaaag tgaccaggta | 2100 |
| gaccctttt aattacattc actacttcta ccacttgtgt atctctagcc aatgtgcttg | 2160 |
| caagtgtaca gatctgtgta gaggaatgtg tgtatattta cctcttcgtt tgctcaaaca | 2220 |
| tgagtgggta ttttttgtt tgttttttt gttgttgttg ttttgaggc gcgtctcacc | 2280 |
| ctgttgccca ggctggagtg caatggcgcg ttctctgctc actacagcac ccgcttccca | 2340 |
| ggttgaagtg attctcttgc ctcagcctcc cgagtagctg ggattacagg tgcccaccac | 2400 |
| cgcgcccagc taattttta attttagta gagacaggt tttaccatgt tggccaggct | 2460 |
| ggtcttgaac tcctgaccct caagtgatct gcccaccttg gcctcctaa gtgctgggat | 2520 |
| tataggcgtg agccaccatg ctcagccatt aaggtatttt gttaagaact ttaagtttag | 2580 |
| ggtaagaaga atgaaaatga tccagaaaaa tgcaagcaag tccacatgga gatttggagg | 2640 |
| acactggtta aagaatttat ttctttgtat agtatactat gttcatggtg cagatactac | 2700 |
| aacattgtgg cattttagac tcgttgagtt tcttgggcac tcccaagggc gttggggtca | 2760 |
| taaggagact ataactctac agattgtgaa tatatttatt ttcaagttgc attctttgtc | 2820 |
| tttttaagca atcagatttc aagagagctc aagctttcag aagtcaatgt gaaaattcct | 2880 |
| tcctaggctg tcccacagtc tttgctgccc ttagatgaag ccacttgttt caagatgact | 2940 |
| actttggggt tgggttttca tctaaacaca tttttccagt cttattagat aaattagtcc | 3000 |
| atatggttgg ttaatcaaga gccttctggg tttggtttgg tggcattaaa tgg | 3053 |

<210> SEQ ID NO 4
<211> LENGTH: 2735
<212> TYPE: DNA
<213> ORGANISM: Homo sapiens

<400> SEQUENCE: 4

| | |
|---|---:|
| acaacagtcc ccaggcatca ccattcaaga tgcatccagg ggtcctggct gccttcctct | 60 |
| tcttgagctg gactcattgt cgggccctgc cccttcccag tggtggtgat gaagatgatt | 120 |
| tgtctgagga agacctccag tttgcagagc gctacctgag atcatactac catcctacaa | 180 |
| atctcgcggg aatcctgaag gagaatgcag caagctccat gactgagagg ctccgagaaa | 240 |
| tgcagtcttt cttcggctta gaggtgactg gcaaacttga cgataacacc ttagatgtca | 300 |
| tgaaaaagcc aagatgcggg gttcctgatg tgggtgaata caatgttttc cctcgaactc | 360 |
| ttaaatggtc caaaatgaat ttaacctaca gaattgtgaa ttacacccct gatatgactc | 420 |
| attctgaagt cgaaaaggca ttcaaaaaag ccttcaaagt ttggtccgat gtaactcctc | 480 |
| tgaattttac cagacttcac gatggcattg ctgacatcat gatctctttt ggaattaagg | 540 |
| agcatggcga cttctaccca tttgatgggc cctctggcct gctggctcat gcttttcctc | 600 |
| ctgggccaaa ttatggagga gatgccatt tgatgatga tgaaacctgg acaagtagtt | 660 |
| ccaaaggcta caacttgttt cttgttgctg cgcatgagtt cggccactcc ttaggtcttg | 720 |
| accactccaa ggaccctgga gcactcatgt ttcctatcta cacctacacc ggcaaaagcc | 780 |
| actttatgct tcctgatgac gatgtacaag ggatccagtc tctctatggt ccaggagatg | 840 |
| aagaccccaa ccctaaacat ccaaaaacgc cagacaaatg tgaccttcc ttatccttg | 900 |
| atgccattac cagtctccga ggagaaacaa tgatctttaa agacagattc ttctggcgcc | 960 |
| tgcatcctca gcaggttgat gcggagctgt ttttaacgaa atcattttgg ccagaacttc | 1020 |

-continued

```
ccaaccgtat tgatgctgca tatgagcacc cttctcatga cctcatcttc atcttcagag   1080
gtagaaaatt ttgggctctt aatggttatg acattctgga aggttatccc aaaaaaatat   1140
ctgaactggg tcttccaaaa gaagttaaga agataagtgc agctgttcac tttgaggata   1200
caggcaagac tctcctgttc tcaggaaacc aggtctggag atatgatgat actaaccata   1260
ttatggataa agactatccg agactaatag aagaagactt cccaggaatt ggtgataaag   1320
tagatgctgt ctatgagaaa aatggttata tctattttt caacggaccc atacagtttg    1380
aatacagcat ctggagtaac cgtattgttc gcgtcatgcc agcaaattcc attttgtggt   1440
gttaagtgtc ttttaaaaa ttgttattta aatcctgaag agcatttggg gtaatacttc    1500
cagaagtgcg gggtagggga agaagagcta tcaggagaaa gcttggttct gtgaacaagc   1560
ttcagtaagt tatctttgaa tatgtagtat ctatatgact atgcgtggct ggaaccacat   1620
tgaagaatgt tagagtaatg aaatggagga tctctaaaga gcatctgatt cttgttgctg   1680
tacaaaagca atggttgatg atacttccca caccacaaat gggacacatg gtctgtcaat   1740
gagagcataa tttaaaaata tatttataag gaaattttac aagggcataa agtaaataca   1800
tgcatataat gaataaatca ttcttactaa aaagtataaa atagtatgaa aatggaaatt   1860
tgggagagcc atacataaaa gaaataaacc aaaggaaaat gtctgtaata atagactgta   1920
acttccaaat aaataatttt cattttgcac tgaggatatt cagatgtatg tgcccttctt   1980
cacacagaca ctaacgaaat atcaaagtca ttaaagacag gagacaaaag agcagtggta   2040
agaatagtag atgtggcctt tgaattctgt ttaatttttca cttttggcaa tgactcaaag   2100
tctgctctca tataagacaa atattccttt gcatattata aaggataaag aaggatgatg   2160
tcttttttatt aaaatatttc aggttcttca gaagtcacac attacaaagt taaaattgtt   2220
atcaaaaatag tctaaggcca tggcatccct ttttcataaa ttatttgatt atttaagact   2280
aaaagttgca ttttaacccct attttaccta gctaattatt taattgtcca gtttgtcttg   2340
gatatatagg ctattttcta aagacttgta tagcatgaaa taaatatat cttataaagt    2400
ggaagtatgt atattaaaaa agagacatcc aaattttttt ttaaagcagt ctactagatt   2460
gtgatccctt gagatatgga aggatgcctt ttttctctg catttaaaaa aatcccccag    2520
cacttcccac agtgcctatt gatacttggg gagggtgctt ggcacttatt gaatatatga   2580
tcggccatca agggaagaac tattgtgctc agagacactg ttgataaaaa ctcaggcaaa   2640
gaaaatgaaa tgcatatttg caaagtgtat taggaagtgt ttatgttgtt tataataaaa   2700
atatattttc aacagacaaa aaaaaaaaaa aaaaa                              2735
```

<210> SEQ ID NO 5
<211> LENGTH: 1750
<212> TYPE: DNA
<213> ORGANISM: Homo sapiens

<400> SEQUENCE: 5

```
gcgacggtta acgggcccc aaggcagggg tggcgggtca gtgctgctcg ggggcttctc     60
catccaggtc cctggagttc ctggtccctg gagctccgca cttggcggcg caacctgcgt   120
gaggcagcgc gactctggcg actggccggc catgccttcc cgggctgagg actatgaagt   180
gttgtacacc attggcacag gctcctacgg ccgctgccag aagatccgga ggaagagtga   240
tgcaagata ttagttttgga agaacttga ctatggctcc atgacagaag ctgagaaaca    300
gatgcttgtt tctgaagtga attgcttcg tgaactgaaa catccaaaca tcgttcgtta   360
ctatgatcgg attattgacc ggaccaatac aacactgtac attgtaatgg aatattgtga   420
```

-continued

| | |
|---|---|
| aggaggggat ctggctagtg taattacaaa gggaaccaag gaaaggcaat acttagatga | 480 |
| agagtttgtt cttcgagtga tgactcagtt gactctggcc ctgaaggaat gccacagacg | 540 |
| aagtgatggt ggtcataccg tattgcatcg ggatctgaaa ccagccaatg ttttcctgga | 600 |
| tggcaagcaa aacgtcaagc ttggagactt tgggctagct agaatattaa accatgacac | 660 |
| gagttttgca aaacatttg ttggcacacc ttattacatg tctcctgaac aaatgaatcg | 720 |
| catgtcctac aatgagaaat cagatatctg tcattgggc tgcttgctgt atgagttatg | 780 |
| tgcattaatg cctccattta cagcttttag ccagaaagaa ctcgctggga aaatcagaga | 840 |
| aggcaaattc aggcgaattc ataccgtta ctctgatgaa ttgaatgaaa ttattacgag | 900 |
| gatgttaaac ttaaaggatt accatcgacc ttctgttgaa gaaattcttg agaacccttt | 960 |
| aatagcagat ttggttgcag acgagcaaag aagaaatctt gagagaagag ggcgacaatt | 1020 |
| aggagagcca gaaaaatcgc aggattccag ccctgtattg agtgagctga actgaagga | 1080 |
| aattcagtta caggagcgag agcgagctct caaagcaaga gaagaaagat tggagcagaa | 1140 |
| agaacaggag ctttgtgttc gtgagagact agcagaggac aaactggcta gagcagaaaa | 1200 |
| tctgttgaag aactacagct tgctaaagga acggaagttc ctgtctctgg caagtaatcc | 1260 |
| agagtctcac tttgttgccc aggctggaat gcagtggtgt gatcacagct caatgtagcc | 1320 |
| ttggcctcgt aggctcaagt aatcctccca cttcagcctc ctgtgatgga gtctcactgt | 1380 |
| tttgcccagg atggtcttga actcatgggc tcaagcaatc ctcccacctt ggctgggatt | 1440 |
| acaggtatga gccattgcgc ccagcccctt tatgacctat ttctttatga atatggcttg | 1500 |
| tctgttcatt actgatataa ttatgcaact ttcattagta tatatgaatg tttatgcttg | 1560 |
| cacaaaaatg tatgttatta ttgcctattt tattgcataa agtgacctat gaagtgttct | 1620 |
| gtgttttcat atgtttctca aataaattcc ctttaaaaat gtaaatacat gtaaatgtaa | 1680 |
| aaaaaaaagt aaataaatat cttttaaaga attttttaaaa aaaaaaaaaa aaaaaaaaa | 1740 |
| aaaaaaaaaa | 1750 |

<210> SEQ ID NO 6
<211> LENGTH: 3452
<212> TYPE: DNA
<213> ORGANISM: Homo sapiens

<400> SEQUENCE: 6

| | |
|---|---|
| aaaatcgcgc gcggccccgc ggccagcctg ggtaggggca aggcgcagcc aatgggaagg | 60 |
| gtcggaggca tggcacagcc aatgggaagg gccggggcac caaagccaat gggaagggcc | 120 |
| gggagcgcgc ggcgcgggag atttaaaggc tgctggagtg aggggtcgcc cgtgcaccct | 180 |
| gtcccagccg tcctgtcctg gctgctcgct ctgcttcgct cgcgcctccac tatgctctcc | 240 |
| ctccgtgtcc cgctcgcgcc catcacggac ccgcagcagc tgcagctctc gccgctgaag | 300 |
| gggctcagct tggtcgacaa ggagaacacg ccgccgccc tgagcgggac ccgcgtcctg | 360 |
| gccagcaaga ccgcgaggag gatcttccag gagcccacgg agccgaaaac taaagcagct | 420 |
| gccccggcg tggaggatga gccgctgctg agagaaaacc cccgccgctt tgtcatcttc | 480 |
| cccatcgagt accatgatat ctggcagatg tataagaagg cagaggcttc cttttggacc | 540 |
| gccgaggagg tggacctctc caaggacatt cagcactggg aatccctgaa acccgaggag | 600 |
| agatatttta tatcccatgt tctggctttc tttgcagcaa gcgatggcat agtaaatgaa | 660 |
| aacttggtgg agcgatttag ccaagaagtt cagattacag aagcccgctg tttctatggc | 720 |

-continued

```
ttccaaattg ccatggaaaa catacattct gaaatgtata gtcttcttat tgacacttac    780
ataaaagatc ccaaagaaag ggaatttctc ttcaatgcca ttgaaacgat gccttgtgtc    840
aagaagaagg cagactgggc cttgcgctgg attggggaca agaggctac ctatggtgaa     900 cgtgttgtag cctttgctgc agtggaaggc attttctttt ccggttcttt tgcgtcgata    960
ttctggctca agaaacgagg actgatgcct ggcctcacat tttctaatga acttattagc   1020
agagatgagg gtttacactg tgattttgct tgcctgatgt tcaaacacct ggtacacaaa   1080
ccatcggagg agagagtaag agaaataatt atcaatgctg ttcggataga acaggagttc   1140
ctcactgagg ccttgcctgt gaagctcatt gggatgaatt gcactctaat gaagcaatac   1200
attgagtttg tggcagacag acttatgctg gaactgggtt ttagcaaggt tttcagagta   1260
gagaacccat ttgactttat ggagaatatt tcactggaag gaaagactaa cttctttgag   1320
aagagagtag gcgagtatca gaggatggga gtgatgtcaa gtccaacaga gaattctttt   1380
accttggatg ctgacttcta aatgaactga agatgtgccc ttacttggct gattttttt    1440 ttccatctca taagaaaaat cagctgaagt gttaccaact agccacacca tgaattgtcc   1500
gtaatgttca ttaacagcat cttaaaact gtgtagctac ctcacaacca gtcctgtctg    1560
tttatagtgc tggtagtatc acctttgcc agaaggcctg gctggctgtg acttaccata    1620
gcagtgacaa tggcagtctt ggcttttaaag tgaggggtga ccctttagtg agcttagcac   1680
agcgggatta aacagtcctt taaccagcac agccagttaa aagatgcagc ctcactgctt   1740
caacgcagat tttaatgttt acttaaatat aaacctggca ctttacaaac aaataaacat   1800
tgtttgtact cacaaggcga taatagcttg atttatttgg tttctacacc aaatacattc   1860
tcctgaccac taatgggagc caattcacaa ttcactaagt gactaaagta agttaaactt   1920
gtgtagacta agcatgtaat ttttaagttt tattttaatg aattaaaata tttgttaacc   1980
aactttaaag tcagtcctgt gtatacctag atattagtca gttggtgcca gatagaagac   2040
aggttgtgtt tttatcctgt ggcttgtgta gtgtcctggg attctctgcc ccctctgagt   2100
agagtgttgt gggataaagg aatctctcag ggcaaggagc ttcttaagtt aaatcactag   2160
aaatttaggg gtgatctggg ccttcatatg tgtgagaagc cgtttcattt tatttctcac   2220
tgtattttcc tcaacgtctg gttgatgaga aaaaattctt gaagagtttt catatgtggg   2280
agctaaggta gtattgtaaa atttcaagtc atccttaaac aaaatgatcc acctaagatc   2340
ttgcccctgt taagtggtga aatcaactag aggtggttcc tacaagttgt tcattctagt   2400
tttgtttggt gtaagtaggt tgtgtgagtt aattcattta tatttactat gtctgttaaa   2460
tcagaaattt tttattatct atgttcttct agattttacc tgtagttcat acttcagtca   2520
cccagtgtct tattctggca ttgtctaaat ctgagcattg tctaggggga tcttaaactt   2580
tagtaggaaa ccatgagctg ttaatacagt ttccattcaa atattaattt cagaatgaaa   2640
cataattttt ttttttttt ttgagatgga gtctcgctct gttgcccagg ctggagtgca   2700
gtggcgcgat tttggctcac tgtaacctcc atctcctggg ttcaagcaat tctcctgtct   2760
cagcctccct agtagctggg actgcaggta tgtgctacca cacctggcta atttttgtat   2820
ttttagtaga gatggagttt caccatattg gtcaggctgg tcttgaactc ctgacctcag   2880
gtgatccacc cacctcggcc tcccaaagtg ctgggattgc aggcgtgata aacaaatatt   2940
cttaataggg ctactttgaa ttaatctgcc tttatgtttg ggagaagaaa gctgagacat   3000
tgcatgaaag atgatgagag ataaatgttg atctttggc cccatttgtt aattgtattc    3060
agtatttgaa cgtcgtcctg tttattgtta gttttcttca tcatttattg tatagacaat   3120
```

| | |
|---|---|
| ttttaaatct ctgtaatatg atacattttc ctatcttta agttattgtt acctaaagtt | 3180 |
| aatccagatt atatggtcct tatatgtgta caacattaaa atgaaaggct ttgtcttgca | 3240 |
| ttgtgaggta caggcggaag ttggaatcag gttttaggat tctgtctctc attagctgaa | 3300 |
| taatgtgagg attaacttct gccagctcag accatttcct aatcagttga aagggaaaca | 3360 |
| agtatttcag tctcaaaatt gaataatgca caagtcttaa gtgattaaaa taaaactgtt | 3420 |
| cttatgtcag tttcaaaaaa aaaaaaaaaa aa | 3452 |

<210> SEQ ID NO 7
<211> LENGTH: 5753
<212> TYPE: DNA
<213> ORGANISM: Homo sapiens
<400> SEQUENCE: 7

| | |
|---|---|
| gattggctgg tctgcttcgg gcgggctaaa ggaaggttca agtggagctc tcctaaccga | 60 |
| cgcgcgtctg tggagaagcg gcttggtcgg gggtggtctc gtggggtcct gcctgtttag | 120 |
| tcgctttcag ggttcttgag ccccttcacg accgtcacca tggaagtgtc accattgcag | 180 |
| cctgtaaatg aaatatgca agtcaacaaa ataagaaaa atgaagatgc taagaaaaga | 240 |
| ctgtctgttg aaagaatcta tcaaaagaaa acacaattgg aacatatttt gctccgccca | 300 |
| gacacctaca ttggttctgt ggaattagtg acccagcaaa tgtgggttta cgatgaagat | 360 |
| gttggcatta actatagga agtcactttt gttcctggtt tgtacaaaat ctttgatgag | 420 |
| attctagtta atgctgcgga caacaaacaa agggacccaa aaatgtcttg tattagagtc | 480 |
| acaattgatc cggaaaacaa tttaattagt atatggaata tggaaaagg tattcctgtt | 540 |
| gttgaacaca aagttgaaaa gatgtatgtc ccagctctca tatttggaca gctcctaact | 600 |
| tctagtaact atgatgatga tgaaaagaaa gtgacaggtg gtcgaaatgg ctatggagcc | 660 |
| aaattgtgta acatattcag taccaaatt actgtggaaa cagccagtag agaatacaag | 720 |
| aaaatgttca acagacatg gatggataat atgggaagag ctggtgagat ggaactcaag | 780 |
| cccttcaatg gagaagatta tacatgtatc acctttcagc ctgatttgtc taagtttaaa | 840 |
| atgcaaagcc tggacaaaga tattgttgca ctaatggtca aagagcata tgatattgct | 900 |
| ggatccacca agatgtcaa agtctttctt aatggaaata aactgccagt aaaaggattt | 960 |
| cgtagttatg tggacatgta tttgaaggac aagttggatg aaactggtaa ctccttgaaa | 1020 |
| gtaatacatg aacaagtaaa ccacaggtgg gaagtgtgtt taactatgag tgaaaaaggc | 1080 |
| tttcagcaaa ttagctttgt caacagcatt gctacatcca agggtggcag acatgttgat | 1140 |
| tatgtagctg atcagattgt gactaaactt gttgatgttg tgaagaagaa gaacaagggt | 1200 |
| ggtgttgcag taaaagcaca tcaggtgaaa aatcacatgt ggattttgt aaatgcctta | 1260 |
| attgaaaacc caacctttga ctctcagaca aagaaaaca tgactttaca acccaagagc | 1320 |
| tttggatcaa catgccaatt gagtgaaaaa tttatcaaag ctgccattgg ctgtggtatt | 1380 |
| gtagaaagca tactaaactg ggtgaagttt aaggcccaag tccagttaaa caagaagtgt | 1440 |
| tcagctgtaa acataatag aatcaaggga attcccaaac tcgatgatgc caatgatgca | 1500 |
| gggggccgaa actccactga gtgtacgctt atcctgactg agggagattc agccaaaact | 1560 |
| ttggctgttt caggccttgg tgtggttggg agagacaaat atgggttttt ccctcttaga | 1620 |
| ggaaaaatac tcaatgttcg agaagcttct cataagcaga tcatggaaaa tgctgagatt | 1680 |
| aacaatatca tcaagattgt gggtcttcag tacaagaaaa actatgaaga tgaagattca | 1740 |

```
ttgaagacgc ttcgttatgg gaagataatg attatgacag atcaggacca agatggttcc    1800
cacatcaaag gcttgctgat taattttatc catcacaact ggccctctct tctgcgacat    1860
cgttttctgg aggaatttat cactcccatt gtaaaggtat ctaaaaacaa gcaagaaatg    1920
gcattttaca gccttcctga atttgaagag tggaagagtt ctactccaaa tcataaaaaa    1980
tggaaagtca atattacaa aggtttgggc accagcacat caaggaagc taagaatac     2040 tttgcagata tgaaaagaca tcgtatccag ttcaaatatt ctggtcctga agatgatgct    2100
gctatcagcc tggcctttag caaaaaacag atagatgatc gaaaggaatg gttaactaat    2160
ttcatggagg atagaagaca cgaaagtta cttgggcttc ctgaggatta cttgtatgga    2220
caaactacca catatctgac atataatgac ttcatcaaca aggaacttat cttgttctca    2280
aattctgata cgagagatc tatcccttct atggtggatg gtttgaaacc aggtcagaga    2340
aaggttttgt ttacttgctt caaacggaat gacaagcgag aagtaaaggt tgcccaatta    2400
gctggatcag tggctgaaat gtcttcttat catcatggtg agatgtcact aatgatgacc    2460
attatcaatt tggctcagaa ttttgtgggt agcaataatc taaacctctt gcagcccatt    2520
ggtcagtttg gtaccaggct acatggtggc aaggattctg ctagtccacg atacatcttt    2580
acaatgctca gctcttttggc tcgattgtta tttccaccaa aagatgatca cacgttgaag    2640
tttttatatg atgacaacca gcgtgttgag cctgaatggt acattcctat tattcccatg    2700
gtgctgataa atggtgctga aggaatcggt actgggtggt cctgcaaaat ccccaacttt    2760
gatgtgcgtg aaattgtaaa taacatcagg cgtttgatgg atggagaaga acctttgcca    2820
atgcttccaa gttacaagaa cttcaagggt actattgaag aactggctcc aaatcaatat    2880
gtgattagtg gtgaagtagc tattcttaat tctacaacca ttgaaatctc agagcttccc    2940
gtcagaacat ggacccagac atacaaagaa caagttctag aacccatgtt gaatggcacc    3000
gagaagacac ctcctctcat aacagactat agggaatacc atacagatac cactgtgaaa    3060
tttgttgtga agatgactga agaaaaactg gcagaggcag agagagttgg actacacaaa    3120
gtcttcaaac tccaaactag tctcacatgc aactctatgg tgcttttga ccacgtaggc    3180 tgtttaaaga aatatgacac ggtgttggat attctaagag acttttttga actcagactt    3240
aaatattatg gattaagaaa agaatggctc ctaggaatgc ttggtgctga atctgctaaa    3300
ctgaataatc aggctcgctt tatcttagag aaaatagatg gcaaaataat cattgaaaat    3360
aagcctaaga agaattaat taaagttctg attcagaggg gatatgattc ggatcctgtg    3420
aaggcctgga agaagcccca gcaaaaggtt ccagatgaag aagaaaatga agagagtgac    3480
aacgaaaagg aaactgaaaa gagtgactcc gtaacagatt ctggaccaac cttcaactat    3540
cttcttgata tgccccttg gtatttaacc aaggaaaaga aagatgaact ctgcaggcta    3600
agaaatgaaa aagaacaaga gctggacaca ttaaaaagaa agagtccatc agatttgtgg    3660
aaagaagact tggctacatt tattgaagaa ttggaggctg ttgaagccaa ggaaaaacaa    3720
gatgaacaag tcggacttcc tgggaaaggg gggaaggcca aggggaaaaa aacacaaatg    3780
gctgaagttt tgccttctcc gcgtggtcaa agagtcattc cacgaataac catagaaatg    3840
aaagcagagc agaaaagaa aaataaaag aaaattaaga atgaaaatac tgaaggaagc    3900
cctcaagaag atggtgtgga actagaaggc ctaaacaaa gattagaaaa gaaacagaaa    3960
agagaaccag gtacaaagac aaagaaacaa actacattgg catttaagcc aatcaaaaaa    4020
ggaaagaaga gaaatccctg gtctgattca gaatcagata ggagcagtga cgaaagtaat    4080
tttgatgtcc ctccacgaga aacagagcca cggagagcag caacaaaaac aaaattcaca    4140
```

```
atggatttgg attcagatga agatttctca gattttgatg aaaaaactga tgatgaagat    4200
tttgtcccat cagatgctag tccacctaag accaaaactt ccccaaaact tagtaacaaa    4260
gaactgaaac cacagaaaag tgtcgtgtca gaccttgaag ctgatgatgt taagggcagt    4320
gtaccactgt cttcaagccc tcctgctaca catttcccag atgaaactga aattacaaac    4380
ccagttccta aaagaatgt gacagtgaag aagacagcag caaaaagtca gtcttccacc    4440
tccactaccg gtgccaaaaa aagggctgcc ccaaaaggaa ctaaaaggga tccagctttg    4500
aattctggtg tctctcaaaa gcctgatcct gccaaaacca gaatcgccg caaaaggaag    4560
ccatccactt ctgatgattc tgactctaat tttgagaaaa ttgtttcgaa agcagtcaca    4620
agcaagaaat ccaaggggga gagtgatgac ttccatatgg actttgactc agctgtggct    4680
cctcgggcaa atctgtacg ggcaaagaaa cctataaagt acctggaaga gtcagatgaa    4740
gatgatctgt tttaaaatgt gaggcgatta ttttaagtaa ttatcttacc aagcccaaga    4800
ctggttttaa agttacctga agctcttaac ttcctcccct ctgaatttag tttggggaag    4860
gtgtttttag tacaagacat caaagtgaag taaagcccaa gtgttcttta gcttttata    4920
atactgtcta aatagtgacc atctcatggg cattgttttc ttctctgctt tgtctgtgtt    4980
ttgagtctgc tttcttttgt ctttaaaacc tgattttta gttcttctga actgtagaaa    5040
tagctatctg atcacttcag cgtaaagcag tgtgtttatt aaccatccac taagctaaaa    5100
ctagagcagt ttgatttaaa agtgtcactc ttcctccttt tctactttca gtagatatga    5160
gatagagcat aattatctgt tttatcttag ttttatacat aatttaccat cagatagaac    5220
tttatggttc tagtacagat actctactac actcagcctc ttatgtgcca agttttttctt    5280
taagcaatga gaaattgctc atgttcttca tcttctcaaa tcatcagagg ccgaagaaaa    5340
acactttggc tgtgtctata acttgacaca gtcaatagaa tgaagaaaat tagagtagtt    5400
atgtgattat ttcagctctt gacctgtccc ctctggctgc ctctgagtct gaatctccca    5460
aagagagaaa ccaatttcta agaggactgg attgcagaag actcggggac aacatttgat    5520
ccaagatctt aaatgttata ttgataacca tgctcagcaa tgagctatta gattcatttt    5580
gggaaatctc cataatttca atttgtaaac tttgttaaga cctgtctaca ttgttatatg    5640
tgtgtgactt gagtaatgtt atcaacgttt ttgtaaatat ttactatgtt tttctattag    5700
ctaaattcca acaattttgt actttaataa aatgttctaa acattgcaac cca           5753

<210> SEQ ID NO 8
<211> LENGTH: 8630
<212> TYPE: DNA
<213> ORGANISM: Homo sapiens

<400> SEQUENCE: 8
taaatttaaa ggcggggcgg cctgtgagcc ctgaagtgcc ggccgcggag ggtcctggcc      60
attttcctgg gaccagttca gcctgatagg atggcggagg aaggagccgt ggccgtctgc     120
gtgcgagtgc ggccgctgaa cagcagagaa gaatcacttg gagaaactgc ccaagtttac     180
tggaaaactg acaataatgt catttatcaa gttgatggaa gtaaatcctt caattttgat     240
cgtgtctttc atggtaatga aactaccaaa atgtgtatg aagaaatagc agcaccaatc     300
atcgattctg ccatacaagg ctacaatggt actatatttg cctatggaca gactgcttca     360
ggaaaaacat ataccatgat gggttcagaa gatcatttgg gagttatacc cagggcaatt     420
catgacattt tccaaaaaat taagaagttt cctgataggg aatttctctt acgtgtatct     480
```

```
tacatggaaa tatacaatga aaccattaca gatttactct gtggcactca aaaaatgaaa      540
cctttaatta ttcgagaaga tgtcaatagg aatgtgtatg ttgctgatct cacagaagaa      600
gttgtatata catcagaaat ggctttgaaa tggattacaa agggagaaaa gagcaggcat      660
tatggagaaa caaaaatgaa tcaaagaagc agtcgttctc ataccatctt taggatgatt      720
ttggaaagca gagagaaggg tgaaccttct aattgtgaag gatctgttaa ggtatcccat      780
ttgaatttgg ttgatcttgc aggcagtgaa agagctgctc aaacaggcgc tgcaggtgtg      840
cggctcaagg aaggctgtaa tataaatcga agcttattta ttttgggaca agtgatcaag      900
aaacttagtg atggacaagt tggtggtttc ataaattatc gagatagcaa gttaacacga      960
attctccaga attccttggg aggaaatgca aagacacgta ttatctgcac aattactcca     1020
gtatcttttg atgaaacact tactgctctc cagtttgcca gtactgctaa atatatgaag     1080
aatactcctt atgttaatga ggtatcaact gatgaagctc tcctgaaaag gtatagaaaa     1140 gaataatgg atcttaaaaa acaattagag gaggtttctt tagagacgcg ggctcaggca     1200
atggaaaaag accaattggc ccaacttttg gaagaaaaag atttgcttca gaaagtacag     1260
aatgagaaaa ttgaaaactt aacacggatg ctggtgacct cttcttccct cacgttgcaa     1320
caggaattaa aggctaaaag aaaacgaaga gttacttggt gccttggcaa aattaacaaa     1380
atgaagaact caaactatgc agatcaattt aatataccaa caaatataac aacaaaaaca     1440
cataagcttt ctataaattt attacgagaa attgatgaat ctgtctgttc agagtctgat     1500
gttttcagta acactcttga tacattaagt gagatagaat ggaatccagc aacaaagcta     1560
ctaaatcagg agaatataga aagtgagttg aactcacttc gtgctgacta tgataatctg     1620
gtattagact atgaacaact acgaacagaa aagaagaaa tggaattgaa attaaaagaa     1680
aagaatgatt tggatgaatt tgaggctcta gaaagaaaaa ctaaaaaaga tcaagagatg     1740
caactaattc atgaaatttc gaacttaaag aatttagtta agcatgcaga agtatataat     1800
caagatcttg agaatgaact cagttcaaaa gtagagctgc ttagagaaaa ggaagaccag     1860
attaagaagc tacaggaata catagactct caaaagctag aaaatataaa aatggacttg     1920
tcatactcat tggaaagcat tgaagaccca aaacaaatga agcagactct gtttgatgct     1980
gaaactgtag cccttgatgc caagagagaa tcagcctttc ttagaagtga aaatctggag     2040
ctgaaggaga aaatgaaaga acttgcaact acatacaagc aaatggaaaa tgatattcag     2100
ttatatcaaa gccagttgga ggcaaaaaag aaaatgcaag ttgatctgga gaaagaatta     2160
caatctgctt ttaatgagat aacaaaactc acctccctta tagatggcaa agttccaaaa     2220
gatttgctct gtaatttgga attggaagga agattactg atcttcagaa agaactaaat     2280
aaagaagttg aagaaatga agctttgcgg gaagaagtca ttttgctttc agaattgaaa     2340
tctttacctt ctgaagtaga aaggctgagg aaagagatac aagacaaatc tgaagagctc     2400
catataataa catcagaaaa agataaattg ttttctgaag tagttcataa ggagagtaga     2460
gttcaaggtt tacttgaaga aattgggaaa acaaagatg acctagcaac tacacagtcg     2520
aattataaaa gcactgatca agaattccaa aatttcaaaa cccttcatat ggactttgag     2580
caaaagtata agatggtcct tgaggagaat gagagaatga atcaggaaat agttaatctc     2640
tctaaagaag cccaaaaatt tgattcgagt ttgggtgctt tgaagaccga gctttcttac     2700
aagacccaag aacttcagga gaaaacacgt gaggttcaag aaagactaaa tgagatggaa     2760
cagctgaagg aacaattaga aaatagagat tctacgctgc aaactgtaga aagggagaaa     2820
acactgatta ctgagaaact gcagcaaact ttagaagaag taaaaacttt aactcaagaa     2880
```

```
aaagatgatc taaaacaact ccaagaaagc ttgcaaattg agagggacca actcaaaagt    2940
gatattcacg atactgttaa catgaatata gatactcaag aacaattacg aaatgctctt    3000
gagtctctga acaacatca agaaacaatt aatacactaa atcgaaaat ttctgaggaa    3060 gtttccagga atttgcatat ggaggaaaat acaggagaaa ctaaagatga atttcagcaa    3120
aagatggttg gcatagataa aaaacaggat ttggaagcta aaaatacccca aacactaact    3180 gcagatgtta aggataatga gataattgag caacaaagga agatattttc tttaatacag    3240
gagaaaaatg aactccaaca aatgttagag agtgttatag cagaaaagga acaattgaag    3300
actgacctaa aggaaaatat tgaaatgacc attgaaaacc aggaagaatt aagacttctt    3360
ggggatgaac ttaaaaagca acaagagata gttgcacaag aaaagaacca tgccataaag    3420
aaagaaggag agctttctag gacctgtgac agactggcag aagttgaaga aaaactaaag    3480 gaaagagcc agcaactcca agaaaaacag caacaacttc ttaatgtaca agaagagatg    3540
agtgagatgc agaaaaagat taatgaaata gagaatttaa agaatgaatt aaagaacaaa    3600
gaattgacat tggaacatat ggaaacagag aggcttgagt tggctcagaa acttaatgaa    3660
aattatgagg aagtgaaatc tataaccaaa gaaagaaaag ttctaaagga attacagaag    3720
tcatttgaaa cagagagaga ccaccttaga ggatatataa gagaaattga agctacaggc    3780
ctacaaacca agaagaact aaaaattgct catattcacc taaaagaaca ccaagaaact    3840
attgatgaac taagaagaag cgtatctgag aagacagctc aaataataaa tactcaggac    3900
ttagaaaaat cccataccaa attacaagaa gagatcccag tgcttcatga ggaacaagag    3960
ttactgccta atgtgaaaga agtcagtgag actcaggaaa caatgaatga actggagtta    4020
ttaacagaac agtccacaac caaggactca acaacactgg caagaataga aatggaaagg    4080
ctcaggttga atgaaaaatt tcaagaaagt caggaagaga taaaatctct aaccaaggaa    4140
agagacaacc ttaaaacgat aaaagaagcc cttgaagtta acatgaccca gctgaaagaa    4200
catattagag aaactttggc taaaatccag gagtctcaaa gcaaacaaga acagtcctta    4260
aatatgaaag aaaaagacaa tgaaactacc aaaatcgtga gtgagatgga gcaattcaaa    4320
cccaaagatt cagcactact aaggatagaa atagaaatgc tcggattgtc caaaagactt    4380
caagaaagtc atgatgaaat gaaatctgta gctaaggaga aagatgacct acagaggctg    4440
caagaagttc ttcaatctga aagtgaccag ctcaaagaaa acataaaaga aattgtagct    4500
aaacacctgg aaactgaaga ggaacttaaa gttgctcatt gttgcctgaa gaacaagag    4560 gaaactatta atgagttaag agtgaatctt tcagagaagg aaactgaaat atcaaccatt    4620
caaaagcagt tagaagcaat caatgataaa ttacagaaca agatccaaga gatttatgag    4680
aaagaggaac aatttaatat aaaacaaatt agtgaggttc aggaaaagt gaatgaactg    4740 aaacaattca aggagcatcg caaagccaag gattcagcac tacaaagtat agaaagtaag    4800
atgctcgagt tgaccaacag acttcaagaa agtcaagaag aaatacaaat tatgattaag    4860 gaaaagagg aaatgaaaag agtacaggag gcccttcaga tagagagaga ccaactgaaa    4920
gaaaacacta agaaattgt agctaaaatg aaagaatctc aagaaaaaga atatcagttt    4980
cttaagatga cagctgtcaa tgagactcag gagaaaatgt gtgaaataga acacttgaag    5040
gagcaatttg agacccagaa gttaaacctg gaaaacatag aaacggagaa tataaggttg    5100
actcagatac tacatgaaaa ccttgaagaa atggagatctg taacaaaaga aagagatgac    5160
cttaggagtg tggaggagac tctcaaagta gagagagacc agctcaagga aaaccttaga    5220
```

```
gaaactataa ctagagacct agaaaaacaa gaggagctaa aaattgttca catgcatctg    5280
aaggagcacc aagaaactat tgataaacta agagggattg tttcagagaa acaaatgaa     5340 atatcaaata tgcaaaagga cttagaacac tcaaatgatg ccttaaaagc acaggatctg    5400
aaaatacaag aggaactaag aattgctcac atgcatctga aagagcagca ggaaactatt    5460
gacaaactca gaggaattgt ttctgagaag acagataaac tatcaaatat gcaaaaagat    5520
ttagaaaatt caaatgctaa attacaagaa aagattcaag aacttaaggc aaatgaacat    5580
caacttatta cgttaaaaaa agatgtcaat gagacacaga aaaagtgtc tgaaatggag     5640 caactaaaga aacaaataaa agaccaaagc ttaactctga gtaaattaga aatagagaat    5700
ttaaatttgg ctcagaaact tcatgaaaac cttgaagaaa tgaaatctgt aatgaaagaa    5760
agagataatc taagaagagt agaggagaca ctcaaactgg agagagacca actcaaggaa    5820
agcctgcaag aaaccaaagc tagagatctg gaaatacaac aggaactaaa aactgctcgt    5880
atgctatcaa agaacacaa agaaactgtt gataaactta gagaaaaaat ttcagaaaag     5940
acaattcaaa tttcagacat tcaaaaggat ttagataaat caaagatga attacagaaa     6000 aagatccaag aacttcagaa aaaagaactt caactgctta gagtgaaaga agatgtcaat    6060
atgagtcata aaaaaattaa tgaaatggaa cagttgaaga agcaatttga ggcccaaaac    6120
ttatctatgc aaagtgtgag aatggataac ttccagttga ctaagaaact tcatgaaagc    6180
cttgaagaaa taagaattgt agctaaagaa agagatgagc taaggaggat aaaagaatct    6240
ctcaaaatgg aaagggacca attcatagca accttaaggg aaatgatagc tagagaccga    6300
cagaaccacc aagtaaaacc tgaaaaaagg ttactaagtg atggacaaca gcaccttacg    6360
gaaagcctga gagaaaagtg ctctagaata aaagagcttt tgaagagata ctcagagatg    6420
gatgatcatt atgagtgctt gaatagattg tctcttgact tggagaagga aattgaattc    6480 caaaagagc tttcaatgag agttaaagca aacctctcac ttccctattt acaaaccaaa     6540
cacattgaaa aacttttttac tgcaaaccag agatgctcca tggaattcca cagaatcatg    6600
aagaaactga agtatgtgtt aagctatgtt acaaaaataa aagaagaaca acatgaatcc    6660
atcaataaat ttgaaatgga ttttattgat gaagtggaaa agcaaaagga attgctaatt    6720
aaaatacagc accttcaaca agattgtgat gtaccatcca gagaattaag ggatctcaaa    6780
ttgaaccaga atatggatct acatattgag gaaattctca aagatttctc agaaagtgag    6840
ttccctagca taaagactga atttcaacaa gtactaagta ataggaaaga aatgacacag    6900
tttttggaag agtggttaaa tactcgtttt gatatagaaa agcttaaaaa tggcatccag    6960
aaagaaaatg ataggatttg tcaagtgaat aacttcttta ataacagaat aattgccata    7020
atgaatgaat caacagagtt tgaggaaaga agtgctacca tatccaaaga gtgggaacag    7080
gacctgaaat cactgaaaga gaaaaatgaa aaactattta aaaactacca aacattgaag    7140
acttccttgg catctggtgc ccaggttaat cctaccacac aagacaataa gaatcctcat    7200
gttacatcaa gagctacaca gttaaccaca gagaaaattc gagagctgga aaattcactg    7260
catgaagcta agaaagtgc tatgcataag gaaagcaaga ttataaagat gcagaaagaa    7320
cttgaggtga ctaatgacat aatagcaaaa cttcaagcca agttcatga atcaaataaa     7380 tgccttgaaa aacaaaaga gacaattcaa gtacttcagg acaaagttgc tttaggagct    7440
aagccatata agaagaaat tgaagatctc aaaatgaagc ttgtgaaaat agacctagag     7500
aaaatgaaaa atgccaaaga atttgaaaag gaaatcagtg ctacaaaagc cactgtgaaa    7560
tatcaaaagg aagttataag gctattgaga gaaaatctca aagaagtca acaggcccaa     7620
```

| | |
|---|---|
| gatacctcag tgatatcaga acatactgat cctcagcctt caaataaacc cttaacttgt | 7680 |
| ggaggtggca gcggcattgt acaaaacaca aaagctctta ttttgaaaag tgaacatata | 7740 |
| aggctagaaa aagaaatttc taagttaaag cagcaaaatg aacagctaat aaaacaaaag | 7800 |
| aatgaattgt taagcaataa tcagcatctt tccaatgagg tcaaaacttg aaggaaaga | 7860 |
| acccttaaaa gagaggctca caaacaagta acttgtgaga attctccaaa gtctcctaaa | 7920 |
| gtgactggaa cagcttctaa aaagaaacaa attacaccct ctcaatgcaa ggaacggaat | 7980 |
| ttacaagatc ctgtgccaaa ggaatcacca aaatcttgtt tttttgatag ccgatcaaag | 8040 |
| tctttaccat cacctcatcc agttcgctat tttgataact caagtttagg cctttgtcca | 8100 |
| gaggtgcaaa atgcaggagc agagagtgtg gattctcagc caggtccttg gcacgcctcc | 8160 |
| tcaggcaagg atgtgcctga gtgcaaaact cagtagactc ctctttgtca cttctctgga | 8220 |
| gatccagcat tccttatttg gaaatgactt tgtttatgtg tctatccctg gtaatgatgt | 8280 |
| tgtagtgcag cttaatttca attcagtctt tactttgcca ctagagttga agataaggg | 8340 |
| aacaggaaat gaatgcattg tggtaattta gaatggtgat agcaatacct tcttcttgca | 8400 |
| tatggtaata cttttaaaag ttgaattgtt ttatttattt gtatatttg taaagaataa | 8460 |
| agttattgaa agaaatgtaa agttatctac atgacttagc atattccaaa gcataataca | 8520 |
| tacattaata taaacatca ttttattaac aaaattgtaa atgttttaa taccttacac | 8580 |
| attcaataaa tgtttagtag ttctgaatca ccaaaaaaaa aaaaaaaaa | 8630 |

<210> SEQ ID NO 9
<211> LENGTH: 11427
<212> TYPE: DNA
<213> ORGANISM: Homo sapiens

<400> SEQUENCE: 9

| | |
|---|---|
| taccgggcgg aggtgagcgc ggcgccggct cctcctgcgg cggactttgg gtgcgacttg | 60 |
| acgagcggtg gttcgacaag tggccttgcg ggccggatcg tcccagtgga agagttgtaa | 120 |
| atttgcttct ggccttcccc tacgattat acctggcctt cccctacgga ttatactcaa | 180 |
| cttactgttt agaaaatgtg gcccacgaga cgcctggtta ctatcaaaag gagcggggtc | 240 |
| gacggtcccc actttcccct gagcctcagc acctgcttgt ttggaagggg tattgaatgt | 300 |
| gacatccgta tccagcttcc tgttgtgtca aaacaacatt gcaaaattga aatccatgag | 360 |
| caggaggcaa tattacataa tttcagttcc acaaatccaa cacaagtaaa tgggtctgtt | 420 |
| attgatgagc ctgtacggct aaaacatgga gatgtaataa ctattattga tcgttccttc | 480 |
| aggtatgaaa atgaaagtct tcagaatgga aggaagtcaa ctgaatttcc aagaaaaata | 540 |
| cgtgaacaga agccagcacg tcgtgtctca agatctagct tctcttctga ccctgatgag | 600 |
| agtgagggaa taccttgaa aagaaggcgt gtgtccttg tgggcacct aagacctgaa | 660 |
| ctatttgatg aaaacttgcc tcctaatacg cctctcaaaa ggggagaagc cccaaccaaa | 720 |
| agaaagtctc tggtaatgca cactccacct gtcctgaaga aaatcatcaa ggaacagcct | 780 |
| caaccatcag gaaacaaga gtcaggttca gaaatccatg tggaagtgaa ggcacaaagc | 840 |
| ttggttataa gccctccagc tcctagtcct aggaaaactc cagttgccag tgatcaacgc | 900 |
| cgtaggtcct gcaaaacagc ccctgcttcc agcagcaaat ctcagacaga ggttcctaag | 960 |
| agaggaggga gaaagagtgg caacctgcct tcaaagagag tgtctatcag ccgaagtcaa | 1020 |
| catgatattt tacagatgat atgttccaaa agaagaagtg gtgcttcgga agcaaatctg | 1080 |

-continued

```
attgttgcaa aatcatgggc agatgtagta aaacttggtg caaaacaaac acaaactaaa    1140
gtcataaaac atggtcctca aaggtcaatg aacaaaaggc aaagaagacc tgctactcca    1200
aagaagcctg tgggcgaagt tcacagtcaa tttagtacag gccacgcaaa ctctccttgt    1260
accataataa tagggaaagc tcatactgaa aaagtacatg tgcctgctcg accctacaga    1320
gtgctcaaca acttcatttc caaccaaaaa atggacttta aggaagatct ttcaggaata    1380
gctgaaatgt tcaagacccc agtgaaggag caaccgcagt tgacaagcac atgtcacatc    1440
gctatttcaa attcagagaa tttgcttgga aaacagtttc aaggaactga ttcaggagaa    1500
gaacctctgc tccccacctc agagagtttt ggaggaaatg tgttcttcag tgcacagaat    1560
gcagcaaaac agccatctga taaatgctct gcaagccctc ccttaagacg gcagtgtatt    1620
agagaaaatg gaaacgtagc aaaaacgccc aggaacacct acaaaatgac ttctctggag    1680
acaaaaactt cagatactga gacagagcct tcaaaaacag tatccactgc aaacaggtca    1740
ggaaggtcta cagagttcag gaatatacag aagctacctg tggaaagtaa gagtgaagaa    1800
acaaatacag aaattgttga gtgcatccta aaaagaggtc agaaggcaac actactacaa    1860
caaaggagag aaggagagat gaaggaaata gaaagacctt ttgagacata taaggaaaat    1920
attgaattaa aagaaaacga tgaaaagatg aaagcaatga agagatcaag aacttggggg    1980
cagaaatgtg caccaatgtc tgacctgaca gacctcaaga gcttgcctga tacagaactc    2040
atgaaagaca cggcacgtgg ccagaatctc ctccaaaccc aagatcatgc caaggcacca    2100
aagagtgaga aaggcaaaat cactaaaatg ccctgccagt cattacaacc agaaccaata    2160
aacaccccaa cacacacaaa acaacagttg aaggcatccc tggggaaagt aggtgtgaaa    2220
gaagagctcc tagcagtcgg caagttcaca cggacgtcag gggagaccac gcacacgcac    2280
agagagccag caggagatgg caagagcatc agaacgttta aggagtctcc aaagcagatc    2340
ctggacccag cagcccgtgt aactggaatg aagaagtggc caagaacgcc taaggaagag    2400
gcccagtcac tagaagacct ggctggcttc aaagagctct tccagacacc aggtccctct    2460
gaggaatcaa tgactgatga gaaaactacc aaaatagcct gcaaatctcc accaccagaa    2520
tcagtggaca ctccaacaag cacaaagcaa tggcctaaga aagtctcag gaaagcagat    2580
gtagaggaag aattcttagc actcaggaaa ctaacaccat cagcagggaa agccatgctt    2640
acgcccaaac cagcaggagg tgatgagaaa gacattaaag catttatggg aactccagtg    2700
cagaaactgg acctggcagg aactttacct ggcagcaaaa gacagctaca gactcctaag    2760
gaaaaggccc aggctctaga agacctggct ggctttaaag agctcttcca gactcctggt    2820
cacaccgagg aattagtggc tgctggtaaa accactaaaa taccctgcga ctctccacag    2880
tcagacccag tggacacccc aacaagcaca aagcaacgac ccaagagaag tatcaggaaa    2940
gcagatgtag agggagaact cttagcgtgc aggaatctaa tgccatcagc aggcaaagcc    3000
atgcacacgc ctaaaccatc agtaggtgaa gagaaagaca tcatcatatt tgtgggaact    3060
ccagtgcaga aactggacct gacagagaac ttaaccggca gcaagagacg ccacaaaact    3120
cctaaggaag aggcccaggc tctggaagac ctgactggct ttaaagagct cttccagacc    3180
cctggtcata ctgaagaagc agtggctgct ggcaaaacta ctaaaatgcc tgcgaatct    3240
tctccaccag aatcagcaga cacccccaaca agcacaagaa ggcagcccaa gacaccttg    3300
gagaaaaggg acgtacagaa ggagctctca gccctgaaga agctcacaca gacatcaggg    3360
gaaaccacac acacagataa agtaccagga ggtgaggata aaagcatcaa cgcgtttagg    3420
gaaactgcaa aacagaaact ggacccagca gcaagtgtaa ctggtagcaa gaggcacccca    3480
```

```
aaaactaagg aaaaggccca accccctagaa gacctggctg gcttgaaaga gctcttccag   3540
acaccagtat gcactgacaa gcccacgact cacgagaaaa ctaccaaaat agcctgcaga   3600
tcacaaccag acccagtgga cacaccaaca agctccaagc cacagtccaa gagaagtctc   3660
aggaaagtgg acgtagaaga agaattcttc gcactcagga acgaacacc atcagcaggc    3720 aaagccatgc acacacccaa accagcagta agtggtgaga aaaacatcta cgcatttatg   3780
ggaactccag tgcagaaact ggacctgaca gagaacttaa ctggcagcaa gagacggcta   3840
caaactccta aggaaaaggc ccaggctcta aagacctggc tggctttaa agagctcttc    3900 cagacacgag gtcacactga ggaatcaatg actaacgata aaactgccaa agtagcctgc   3960
aaatcttcac aaccagaccc agacaaaaac ccagcaagct ccaagcgacg gctcaagaca   4020
tccctgggga aagtgggcgt gaagaagag ctcctagcag ttggcaagct cacacagaca    4080
tcaggagaga ctacacacac acacacagag ccaacaggag atggtaagag catgaaagca   4140
tttatggagt ctccaaagca gatcttagac tcagcagcaa gtctaactgg cagcaagagg   4200
cagctgagaa ctcctaaggg aaagtctgaa gtccctgaag acctggccgg cttcatcgag   4260
ctcttccaga caccaagtca cactaaggaa tcaatgacta acgaaaaaac taccaaagta   4320
tcctacagag cttcacagcc agacctagtg gacaccccaa caagctccaa gccacagccc   4380
aagagaagtc tcaggaaagc agacactgaa gaagaatttt tagcatttag gaaacaaacg   4440
ccatcagcag gcaaagccat gcacacaccc aaaccagcag taggtgaaga gaaagacatc   4500
aacacgtttt tgggaactcc agtgcagaaa ctggaccagc caggaaattt acctggcagc   4560
aatagacggc tacaaactcg taaggaaaag gcccaggctc tagaagaact gactggcttc   4620
agagagcttt tccagacacc atgcactgat aaccccacga ctgatgagaa aactaccaaa   4680
aaaatactct gcaaatctcc gcaatcagac ccagcggaca ccccaacaaa cacaaagcaa   4740
cggcccaaga gaagcctcaa gaaagcagac gtagaggaag aattttttagc attcaggaaa   4800 ctaacaccat cagcaggcaa agccatgcac acgcctaaag cagcagtagg tgaagagaaa   4860
gacatcaaca catttgtggg gactccagtg gagaaactgg acctgctagg aaatttacct   4920
ggcagcaaga acggccaca aactcctaaa gaaaaggcca aggctctaga agatctggct     4980
ggcttcaaag agctcttcca gacaccaggt cacactgagg aatcaatgac cgatgacaaa   5040
atcacagaag tatcctgcaa atctccacaa ccagacccag tcaaaacccc aacaagctcc   5100
aagcaacgac tcaagatatc cttggggaaa gtaggtgtga agaagaggt cctaccagtc    5160 ggcaagctca cacagacgtc agggaagacc acacagacac acagagagac agcaggagat   5220
ggaaagagca tcaaagcgtt taaggaatct gcaaagcaga tgctggaccc agcaaactat   5280
ggaactggga tggagaggtg gccaagaaca cctaaggaag aggcccaatc actagaagac   5340
ctggccggct tcaaagagct cttccagaca ccagaccaca ctgaggaatc aacaactgat   5400
gacaaaacta ccaaaatagc ctgcaaatct ccaccaccag aatcaatgga cactccaaca   5460
agcacaagga ggcggcccaa aacacctttg ggaaaaggg atatagtgga agagctctca    5520
gccctgaagc agctcacaca gaccacacac acagacaaag taccaggaga tgaggataaa   5580
ggcatcaacg tgttcaggga aactgcaaaa cagaaactgg acccagcagc aagtgtaact   5640
ggtagcaaga ggcagccaag aactcctaag ggaaaagccc aaccccctaga gacttggct    5700 ggcttgaaag agctcttcca gacaccaata tgcactgaca gcccacgac tcatgagaaa    5760 actaccaaaa tagcctgcag atctccacaa ccagacccag tgggtacccc aacaatcttc   5820
```

```
aagccacagt ccaagagaag tctcaggaaa gcagacgtag aggaagaatc cttagcactc    5880
aggaaacgaa caccatcagt agggaaagct atggacacac ccaaaccagc aggaggtgat    5940
gagaaagaca tgaaagcatt tatgggaact ccagtgcaga aattggacct gccaggaaat    6000
ttacctggca gcaaaagatg gccacaaact cctaaggaaa aggcccaggc tctagaagac    6060
ctggctggct tcaaagagct cttccagaca ccaggcactg acaagcccac gactgatgag    6120
aaaactacca aaatagcctg caaatctcca caaccagacc cagtggacac cccagcaagc    6180
acaaagcaac ggcccaagag aaacctcagg aaagcagacg tagaggaaga atttttagca    6240
ctcaggaaac gaacaccatc agcaggcaaa gccatggaca caccaaaacc agcagtaagt    6300
gatgagaaaa atatcaacac atttgtggaa actccagtgc agaaactgga cctgctagga    6360
aatttacctg gcagcaagag acagccacag actcctaagg aaaaggctga ggctctagag    6420
gacctggttg gcttcaaaga actcttccag acaccaggtc acactgagga atcaatgact    6480
gatgacaaaa tcacagaagt atcctgtaaa tctccacagc cagagtcatt caaaacctca    6540
agaagctcca agcaaaggct caagataccc ctggtgaaag tggacatgaa agaagagccc    6600
ctagcagtca gcaagctcac acggacatca ggggagacta cgcaaacaca cacagagcca    6660
acaggagata gtaagagcat caaagcgttt aaggagtctc caaagcagat cctggaccca    6720
gcagcaagtg taactggtag caggaggcag ctgagaactc gtaaggaaaa ggcccgtgct    6780
ctagaagacc tggttgactt caaagagctc ttctcagcac caggtcacac tgaagagtca    6840
atgactattg acaaaaacac aaaaattccc tgcaaatctc ccccaccaga actaacagac    6900
actgccacga gcacaaagag atgccccaag acacgtccca ggaaagaagt aaaagaggag    6960
ctctcagcag ttgagaggct cacgcaaaca tcagggcaaa gcacacacac acacaaagaa    7020
ccagcaagcg gtgatgaggg catcaaagta ttgaagcaac gtgcaaagaa gaaaccaaac    7080
ccagtagaag aggaacccag caggagaagg ccaagagcac taaggaaaa ggcccaaccc    7140
ctggaagacc tggccggctt cacagagctc tctgaaacat caggtcacac tcaggaatca    7200
ctgactgctg gcaaagccac taaaataccc tgcgaatctc ccccactaga agtggtagac    7260
accacagcaa gcacaaagag gcatctcagg acacgtgtgc agaaggtaca agtaaaagaa    7320
gagccttcag cagtcaagtt cacacaaaca tcaggggaaa ccacggatgc agacaaagaa    7380
ccagcaggtg aagataaagg catcaaagca ttgaaggaat ctgcaaaaca gacaccggct    7440
ccagcagcaa gtgtaactgg cagcaggaga cggccaagag cacccaggga agtgcccaa    7500
gccatagaag acctagctgg cttcaaagac ccagcagcga gtcacactga agaatcaatg    7560
actgatgaca aaaccactaa aatacccgtc aaatcatcac cagaactaga agacaccgca    7620
acaagctcaa agagacggcc caggacacgt gcccagaaag tagaagtgaa ggaggagctg    7680
ttagcagttg gcaagctcac acaaacctca ggggagacca cgcacaccga caaagagccg    7740
gtaggtgagg gcaaaggcac gaaagcattt aagcaacctg caaagcggaa gctgacgca    7800
gaagatgtaa ttggcagcag gagacagcca agagcaccta aggaaaaggc ccaaccctg    7860
gaagatctgg ccagcttcca agagctctct caaacaccag ccacactga ggaactggca    7920
aatggtgctg ctgatagctt tacaagcgct ccaaagcaaa cacctgacag tggaaaacct    7980
ctaaaaatat ccagaagagt tcttcgggcc cctaaagtag aacccgtggg agacgtggta    8040
agcaccagag accctgtaaa atcacaaagc aaaagcaaca cttccctgcc cccactgccc    8100
ttcaagaggg gaggtggcaa agatggaagc gtcacgggaa ccaagaggct gcgctgcatg    8160
ccagcaccag aggaaattgt ggaggagctg ccagccagca agaagcagag ggttgctccc    8220
```

```
agggcaagag gcaaatcatc cgaacccgtg gtcatcatga agagaagttt gaggacttct    8280
gcaaaaagaa ttgaacctgc ggaagagctg aacagcaacg acatgaaaac caacaaagag    8340
gaacacaaat tacaagactc ggtccctgaa aataagggaa tatccctgcg ctccagacgc    8400
caaaataaga ctgaggcaga acagcaaata actgaggtct ttgtattagc agaaagaata    8460
gaaataaaca gaaatgaaaa gaagcccatg aagacctccc cagagatgga cattcagaat    8520
ccagatgatg gagcccggaa acccatacct agagacaaag tcactgagaa caaaggtgc    8580 ttgaggtctg ctagacagaa tgagagctcc cagcctaagg tggcagagga gagcggaggg    8640
cagaagagtg cgaaggttct catgcagaat cagaaaggga aggagaagc aggaaattca     8700 gactccatgt gcctgagatc aagaaagaca aaagccagc ctgcagcaag cactttggag     8760
agcaaatctg tgcagagagt aacgcggagt gtcaagaggg tgcagaaaaa tccaaagaag    8820
gctgaggaca atgtgtgtgt caagaaaata agaaccagaa gtcataggga cagtgaagat    8880
atttgacaga aaaatcgaac tgggaaaaat ataataaagt tagttttgtg ataagttcta    8940
gtgcagtttt tgtcataaat tacaagtgaa ttctgtaagt aaggctgtca gtctgcttaa    9000
gggaagaaaa cttttggattt gctgggtctg aatcggcttc ataaactcca ctgggagcac    9060
tgctgggctc ctggactgag aatagttgaa caccgggggc tttgtgaagg agtctgggcc    9120
aaggtttgcc ctcagctttg cagaatgaag ccttgaggtc tgtcaccacc cacagccacc    9180
ctacagcagc cttaactgtg acacttgcca cactgtgtcg tcgtttgttt gcctatgtcc    9240
tccagggcac ggtggcagga acaactatcc tcgtctgtcc caacactgag caggcactcg    9300
gtaaacacga atgaatggat gagcgcacgg atgaatggag cttacaagat ctgtctttcc    9360
aatggccggg ggcatttggt ccccaaatta aggctattgg acatctgcac aggacagtcc    9420 tattttttgat gtcctttcct ttctgaaaat aaagttttgt gctttggaga atgactcgtg    9480
agcacatctt tagggaccaa gagtgacttt ctgtaaggag tgactcgtgg cttgccttgg    9540
tctcttggga atacttttct aactagggtt gctctcacct gagacattct ccacccgcgg    9600
aatctcaggg tcccaggctg tgggccatca cgacctcaaa ctggctccta atctccagct    9660
ttcctgtcat tgaaagcttc ggaagtttac tggctctgct cccgcctgtt ttctttctga    9720
ctctatctgg cagcccgatg ccacccagta caggaagtga caccagtact ctgtaaagca    9780
tcatcatcct tggagagact gagcactcag caccttcagc cacgatttca ggatcgcttc    9840
cttgtgagcc gctgcctccg aaatctcctt tgaagcccag acatctttct ccagcttcag    9900
acttgtagat ataactcgtt catcttcatt tactttccac tttgccccct gtcctctctg    9960
tgttccccaa atcagagaat agcccgccat ccccaggtc acctgtctgg attcctcccc    10020
attcacccac cttgccaggt gcaggtgagg atggtgcacc agacagggta gctgtccccc    10080
aaaatgtgcc ctgtgcgggc agtgccctgt ctccacgttt gtttccccag tgtctggcgg    10140
ggagccaggt gacatcataa atacttgctg aatgaatgca gaaatcagcg gtactgactt    10200
gtactatatt ggctgccatg atagggttct cacagcgtca tccatgatcg taagggagaa    10260
tgacattctg cttgagggag ggaatagaaa ggggcaggga ggggacatct gagggcttca    10320
cagggctgca aagggtacag ggattgcacc agggcagaac aggggagggt gttcaaggaa    10380
gagtggctct tagcagaggc actttggaag gtgtgaggca taaatgcttc cttctacgta    10440
ggccaacctc aaaactttca gtaggaatgt tgctatgatc aagttgttct aacactttag    10500
acttagtagt aattatgaac ctcacataga aaaatttcat ccagccatat gcctgtggag    10560
```

| | | | | |
|---|---|---|---|---|
| tggaatattc | tgtttagtag | aaaaatcctt | tagagttcag | ctctaaccag aaatcttgct | 10620 |
| gaagtatgtc | agcacctttt | ctcaccctgg | taagtacagt | atttcaagag cacgctaagg | 10680 |
| gtggttttca | ttttacaggg | ctgttgatga | tgggttaaaa | atgttcattt aagggctacc | 10740 |
| cccgtgttta | atagatgaac | accacttcta | cacaaccctc | cttggtactg ggggagggag | 10800 |
| agatctgaca | aatactgccc | attccctag | gctgactgga | tttgagaaca aatacccacc | 10860 |
| catttccacc | atggtatggt | aacttctctg | agcttcagtt | tccaagtgaa tttccatgta | 10920 |
| ataggacatt | cccattaaat | acaagctgtt | tttactttt | cgcctcccag ggcctgtggg | 10980 |
| atctggtccc | ccagcctctc | ttgggctttc | ttacactaac | tctgtaccta ccatctcctg | 11040 |
| cctcccttag | gcaggcacct | ccaaccacca | cacactccct | gctgttttcc ctgcctggaa | 11100 |
| ctttccctcc | tgccccacca | agatcattc | atccagtcct | gagctcagct taagggaggc | 11160 |
| ttcttgcctg | tgggttccct | cacccccatg | cctgtcctcc | aggctggggc aggttcttag | 11220 |
| tttgcctgga | attgttctgt | acctctttgt | agcacgtagt | gttgtggaaa ctaagccact | 11280 |
| aattgagttt | ctggctcccc | tcctgggggtt | gtaagttttg | ttcattcatg agggccgact | 11340 |
| gcatttcctg | gttactctat | cccagtgacc | agccacagga | gatgtccaat aaagtatgtg | 11400 |
| atgaaatggt | cttaaaaaaa | aaaaaaa | | | 11427 |

<210> SEQ ID NO 10
<211> LENGTH: 1752
<212> TYPE: DNA
<213> ORGANISM: Homo sapiens

<400> SEQUENCE: 10

| | | | | | |
|---|---|---|---|---|---|
| agcctgactt | cagcgctccc | actctcggcc | gacacccctc | atggccaacc gttacaccat | 60 |
| ggatctgact | gccatctacg | agagcctcct | gtcgctgagc | cctgacgtgc ccgtgccatc | 120 |
| cgaccatgga | gggactgagt | ccagcccagg | ctggggctcc | tcgggaccct ggagcctgag | 180 |
| cccctccgac | tccagcccgt | ctggggtcac | ctccgcctg | cctggccgct ccaccagcct | 240 |
| agtggagggc | cgcagctgtg | gctgggtgcc | ccaccccct | ggcttcgcac cgctggctcc | 300 |
| ccgcctgggc | cctgagctgt | caccctcacc | cacttcgccc | actgcaacct ccaccacccc | 360 |
| ctcgcgctac | aagactgagc | tatgtcggac | cttctcagag | agtgggcgct gccgctacgg | 420 |
| ggccaagtgc | cagtttgccc | atggcctggg | cgagctgcgc | caggccaatc gccaccccaa | 480 |
| atacaagacg | gaactctgtc | acaagttcta | cctccagggc | cgctgcccct acggctctcg | 540 |
| ctgccacttc | atccacaacc | ctagcgaaga | cctggcggcc | ccgggccacc ctcctgtgct | 600 |
| tcgccagagc | atcagcttct | ccggcctgcc | ctctggccgc | cggacctcac caccaccacc | 660 |
| aggcctggcc | ggcccttccc | tgtcctccag | ctccttctcg | cctccagct ccccaccacc | 720 |
| acctggggac | cttccactgt | caccctctgc | cttctctgct | gcccctggca cccccctggc | 780 |
| tcgaagagac | cccaccccag | tctgttgccc | ctcctgccga | agggccactc ctatcagcgt | 840 |
| ctgggggccc | ttgggtggcc | tggttcggac | ccctctgta | cagtccctgg gatccgaccc | 900 |
| tgatgaatat | gccagcagcg | gcagcagcct | ggggggctct | gactctcccg tcttcgaggc | 960 |
| gggagttttt | gcaccacccc | agccgtggc | agcccccgg | cgactcccca tcttcaatcg | 1020 |
| catctctgtt | tctgagtgac | aaagtgactg | cccggtcaga | tcagctggat ctcagcgggg | 1080 |
| agccacgtct | cttgcactgt | ggtctctgca | tggaccccag | ggctgtgggg acttggggga | 1140 |
| cagtaatcaa | gtaatcccct | tttccagaat | gcattaaccc | actcccctga cctcacgctg | 1200 |
| gggcaggtcc | ccaagtgtgc | aagctcagta | ttcatgatgg | tgggggatgg agtgtcttcc | 1260 |

```
gaggttcttg ggggaaaaaa aattgtagca tatttaaggg aggcaatgaa ccctctcccc    1320
cacctcttcc ctgcccaaat ctgtctccta gaatcttatg tgctgtgaat aataggcctt    1380
cactgcccct ccagttttta tagacctgag gttccagtgt ctcctggtaa ctggaacctc    1440
tcctgagggg gaatcctggt gctcaaatta ccctccaaaa gcaagtagcc aaagccgttg    1500
ccaaacccca cccataaatc aatgggccct ttatttatga cgactttatt tattctaata    1560
tgattttata gtatttatat atattgggtc gtctgcttcc cttgtatttt tcttcctttt    1620
tttgtaatat tgaaaacgac gatataatta ttataagtag actataatat atttagtaat    1680
atatattatt accttaaaag tctattttg tgttttgggc attttttaaat aaacaatctg    1740 agtgtaagct gg                                                        1752

<210> SEQ ID NO 11
<211> LENGTH: 6075
<212> TYPE: DNA
<213> ORGANISM: Homo sapiens

<400> SEQUENCE: 11
ggtcgtgcgc gctgaggagg agccgctgcc gccgtcgccg tcgccgccac cgccgccacc      60
gctaccgagg ccgagcggag ccgttagcgc cgcgccgccg ccgcctcccg cccgcccgg     120 agcagccccg ggcccgcccg cccgcatcca gattttgaa aaatacaatg tctaatggtt     180
atgaagacca catggccgaa gactgcaggg gtgacatcgg gagaacgaat ttgatcgtca     240
actacctccc tcagaacatg acccaggatg agttacgaag cctgttcagc agcattggtg     300
aagttgaatc tgcaaaactt attcgggata agtagcagg acacagcttg ggctatggct     360
ttgtgaacta cgtgaccgcg aaggatgcag agagagcgat caacacgctg aacggcttga     420
ggctccagtc aaaaaccatt aaggtgtcgt atgctcgccc gagctcagag gtgatcaaag     480
acgccaactt gtacatcagc gggctcccgc ggaccatgac ccagaaggac gtagaagaca     540
tgttctctcg gtttgggcgg atcatcaact cgcgggtcct cgtggatcag actacaggtt     600
tgtccagagg ggttgcgttt atccggtttg acaaacggtc ggaggcagaa gaggcaatta     660
ccagtttcaa tggtcataaa cccccaggtt cctctgagcc catcacagtg aagtttgcag     720
ccaaccccaa ccagaacaaa aacgtggcac tcctctcgca gctgtaccac tcgccagcgc     780
gacggttcgg aggccccgtt caccaccagg cgcagagatt caggttctcc cccatgggcg     840
tcgatcacat gagcgggctc tctggcgtca acgtgccagg aaacgcctcc tccggctggt     900
gcattttcat ctacaacctg ggcaggatg ccgacgaggg gatcctctgg cagatgtttg     960
ggccgtttgg tgccgtcacc aatgtgaaag tgatccgcga cttcaacacc aacaagtgca    1020 aagggttgg ctttgtgacc atgacaaact atgaagaagc cgcgatggcc atagccagcc    1080
tgaacggcta ccgcctgggg gacaaaatct acaggtttc cttcaaaacc aacaagtccc    1140
acaaataact cgctcatgct ttttttgta cggaatagat aattaagagt gaaggagttg    1200
aaacttttct tgttagtgta caactcattt tgcgccaatt ttcacaagtg tttgtctttg    1260
tctgaatgag aagtgagaag gttttttatac tctgggatgc aaccgacatg ttcaaatgtt    1320
tgaaatccca caatgttaga ccaatcttaa gtttcgtaag ttatttcctt taagatatat    1380
attaaacaga aatctaagta gaactgcatt gactaaccag tccctctgga tggtggtgaa    1440
cctgaagcat gctttaacct ctaagactgt ctaacacgcg tttcattcaa tgtctccaca    1500
gactgggtag caaaaaaatc acctttagt tttagttttt aatctaaaga tgttagacag    1560
```

```
atgctgagtg tgcgttttct caaccgcttc aacattgtaa gcgatgtatg ctttggttga    1620
caggaagttc cttttccagg caggtcccgt tgccacctcc tgctcactca gtcccgggct    1680
ctgccgagtg gtcctgggaa tggcggcggg cccgtccagc gtgggccacc actggggccg    1740
ggggccacgg gctgcatgct gggcgggccc tccagagaag gacacaaacg tgtttcgtaa    1800
gcccaggcac caatgggaat ggaccaaaga gtttcaggga aactccagta tattccagag    1860
tcagatctaa gctccaggca cgcctgaaga tgtgttgcta ctctgacatc ccgagtttct    1920
gtccacacat tgcatgcaca gcgccccaca cattggatac tgttgttcac gataatttct    1980
cccgttttcc agagcattta acatagcttg gaggcgtaaa atggctctgt attttaataa    2040
cacagaaaca tttgagcatt gtatttctcg catcccttct cgtgagcgct tagacctttt    2100
tctattttag tcggattttg ttttggaatt ttgcttttgt atgaacactc agcagaaaag    2160
tacttacttc ttgccagtta tctattaacc aaaacctttg atttgtagtt ttaaagatta    2220
accctcaaag ttctcttcat aactgccttg acattttggg ttgttctgtt ctgttaattt    2280
tcttttgctt ttttgtgttt tttgtttgtt tttacttttg catttaagac cattaaattt    2340
gattttgttt tgctcgaatt ttgttttgtt ttttatttta ccttttcttt cttttttggct   2400
agggaaggtg caggtggccc agcattcagg gaggagtcgt aagatcttaa gaaaccaatc    2460
cttgcctcaa gcaaaagcat ttctgaatct gtgacgcaag aatgtgcagt tacaggctgg    2520
tggcttttaa accaggagcc cggaggaagg gtgaaagaga aagcctgtga ataggcagg    2580
gccagatcac ccaaaactcc tcaggactgg gatctggcgt ttataaataa ctagtttaca    2640
gagagaatca caaacaggat aacttagtac cagcagtttt taaccttgac gtgagactaa    2700
aacgtgaccg taggctgttt tttagttatt gctctcatga gatgatggct gtatttatct    2760
gtttatttat acctatttat gtatttattt attgaagtgt gaaattgagc aataggcagg    2820
caccaccgtc cccagagcag gtcagcgtct cgagaggccc ctggacaatt gaggatgccc    2880
atcccctccc ctttccctga tcttttactg aggggctgtg tgcgcgatcc ttgcaaattg    2940
atgatgttgc catccgtacc caggctgtgt ctcataaaag tcggcctggt gccagagagg    3000
acctcctttc tcccacagaa tcccagatcc tcaggaaaag ccaaaaccga ggcccattgc    3060
ccggattcga cacaaaagag ggtccctgct ctgttgcccg agagcagtct gcatcctggg    3120
accagaatgc tttcctggaa aaagaagcct ttcaggtttc cctgggccag catcttctga    3180
tggaaggtgg gagccaacac ccttctgatg gaaggtggga gccaacaccc ttctgatgga    3240
aggtgggagc caacacccct tctgatggaag gtgggagcca acaccttct gatgaaggt    3300
gggagccaac acccttctga tggaaggcgg gattcccgct tctgaaactc cccctggagt    3360
ctcactccca cacatgccca tagctagcat tcaacagaga actctgtctt aagcttcaac    3420
tgtgaaaatg atgacgggct tgtagcacct cagcttcttt cctcgccccc ttttatctga    3480
atcctatcaa ttattctgat gctgggacag gtgagaagaa actgtgaagt atatgagcct    3540
ttgaaagttc cctgaagttt ctcagttcag gaacattctc attgtatgtg gtctccgctg    3600
tttgaacagc cttctagcta aaaaattcca aagcctttat tgggagtct tagcttgcaa     3660
gcttgtggaa ggatttagct taacaactgt cactcctgaa aagcaatctc tgttccatca    3720
aggttctagt tgctggccct gtgtcctcaa agttcattac atcttatcaa ggcctgtttg    3780
caaaggggag atccctttc ttaaaaaagg ctcaacccaa aagaaccat tcttaaaaa       3840
attttacata gatcagttgt atttctattt agcaaaatg agtgctctgc ttttatttgg     3900
gaatttcgat gaaaaagcgt tcagagtaga taatgttcat ttatcaaaaa tctggtttgg   3960
```

```
gaaataccaa agaggctttg attgaattcc cttttgaccc gtgtgtaact tcctctggta      4020
gttagacccc aggcagctcc gaatttgtga acctgcttcc tgatgaattc tcccttgttc      4080 cccccttggct ctgccattat ttcgttttca gtgtaatttg ccaagccgca gttttctgtg     4140
ctggctgtgc ctctagtcgc agctctgtga ctgattccct cccgggtgct gagtcccctc      4200
cccggccacc atcctgcgtg aatatcctga aattcatggg cttcctcggg ggcccgcccg      4260
caggtggtgc tgggtgggtt ccgccacctt ctcctggaag gtgagccttt tcctggccaa      4320
gggcagctgc cttaacctct gagagtctgc gcttggcctt agtcctggag acccagcctc      4380
cagggactga accgtgctgc tgttgggagc caagaccggc cctttggagc cggcagccca      4440
ggggtccctg ctggatcaga gaaatagaag cacccgaaga cggttagtgg caattccttg      4500
acccggtttg cttccaaatg aaggccattt gtccaccagg cattgaaaag acatgactta      4560
cccagtccgg catcggactt gaaaaatcga aattgacatc actcagctgt tacatttcac      4620
atccgattca gccccctttt atttccatgt gcttttcgca gccttcctgt gttggatgaa      4680
agagaataag aattcagctg acaggaggcc tctatcctgt ccctccaccc caccctccac      4740
ctcaatcccc tccatcttc cccagaccta cctcacctac taggacctga ggcagctcct      4800
tagcagagac ccctgggggtt tagctgactc tgggggtcag gggttcctgt ccccaaactt     4860
cgcaagacag ccctgaagtc acaagtgctt tctttttaagt ggcattggca attggcgtgt    4920
aatgatggca gtagaatctg aatctcggat cccaggcagg gttcacattt ccaaaccttt      4980
ttgatttccc ctgacctcta atggctggat cctattttttc tacaacctttc cagtgacatc    5040 gttcaggttt ctttcttggc catttaaaaa aacaaatttt tttttttctca cttgtaagtc     5100 accgccagta cctaagttag gctaacggag actttgacag gactggattt ttcttccacc     5160
agaagagaag cctttttccgt tggtttgggg ccacctcttt gaccatgacc atgtgatgtt    5220
ccgtttacag tgacttgctt tggggaggg gaggctctct taaccgattc ccatgttgta     5280
cagtagatgg ttagacccttt tgtatattag tgtgttttaa gttattgatt tgttttatat    5340
aaaataattt attttttcagg tgccattttt catttttaact ttgttttttac atgggtttgt  5400 tttcaataaa gtctgacact ggtgtccaaa agtcaacaat aaaatgaatc ccattgtgtt     5460
cttttgaaga tgcctatgta acttttaagc tttttaaatt attttcagaa aaaaaaaag      5520 aaaagccctt atcagttttc catcagccca ttgccttttt atttttttttt tttaatcctt    5580 gtgaataaat gttctttagt gttttaggag gaaaaagcaa acctagattt tgataaccca     5640
gaagacttca gattaataaa gaagctttga aagaagacca ttttttcaaaa ttttagtgaa    5700 gtgtgaatat ttttttgtcaa tggctttctc aaagagaatg aaactttgc accatttttca   5760 gagtttttat agagatgcca aattgatata tttacatgta atggaaacat gaaaagttt      5820 tattaaacaa ttgttcatag ctgtgtagac atttttaattc agtttccaaa gctctcaaaa    5880 aatcgtatttt ttgaagtacg gagtgatgcg gtttggggcg tggcttacag ttccaacgac   5940
tcaattgtcc cgatactcag ttctttctac aggtatcagg ttcgtgttaa acgctgtatg    6000
ttaactatga ctggaattct gtgatatttt ggtaataaat gaagtgggat cattgcgaaa    6060
aaaaaaaaaa aaaaa                                                      6075
```

<210> SEQ ID NO 12
<211> LENGTH: 1230
<212> TYPE: DNA
<213> ORGANISM: Homo sapiens

<400> SEQUENCE: 12

```
ccgccgccac cgctaccgag gccgagcgga gccgttagcg ccgcgccgcc gccgcctccc        60
gcccgccccg gagcagcccc gggcccgccc gcccgcatcc agattttga  aaaatacaat      120
gtctaatggt tatgaagacc acatggccga agactgcagg ggtgacatcg ggagaacgaa      180
tttgatcgtc aactacctcc ctcagaacat gacccaggat gagttacgaa gcctgttcag      240
cagcattggt gaagttgaat ctgcaaaact tattcgggga aaagtagcag acacagctt       300
gggctacggc tttgtgaact acgtgaccgc gaaggatgca gagagagcga tcaacacgct      360
gaacggcttg aggctccagt caaaaaccat taaggtgtcg tatgctcgcc cgagctcaga      420
ggtgatcaaa acgccaact  tgtacatcag cgggctcccg cggaccatga cccagaagga     480
cgtagaagac atgttctctc ggtttgggcg gatcatcaac tcgcgggtcc tcgtggatca      540
gactacaggt ttgtccagag gggttgcgtt tatccggttt gacaaacggt cggaggcaga     600
agaggcaatt accagtttca atggtcataa accccaggt  tcctctgagc ccatcgcagt     660
gaagtttgca gccaaccca  accagaacaa aaacgtggca ctcctctcgc agctgtacca     720
ctcgccagcg cgacggttcg gaggccccgt tcaccaccag gcgcagagat tcaggttctc      780
ccccatgggc gtcgatcaca tgagcggget ctctggcgtc aacgtgccag aaacgcctc       840
ctccggctgg tgcatttttca tctacaacct gggcaggat  gccgacgagg ggatcctctg    900
gcagatgttt gggccgtttg gtgccgtcac caatgtgaaa gtgatccgcg acttcaacac      960
caacaagtgc aaagggtttg ctttgtgac  catgacaaac tatgaagaag ccgcgatggc    1020
catagccagc ctgaacggct accgcctggg ggacaaaatc ttacaggttt ccttcaaaac    1080
caacaagtcc cacaaataac tcgctcatgc tttttttgta cggaatagat aattaagagt    1140
gaaggagttg aaacttttct tgttagtgta caactcattt tgcgccaatt ttcacaagtg    1200
tttgtctttg tctgaatgag aagtgagaag                                     1230
```

<210> SEQ ID NO 13
<211> LENGTH: 2359
<212> TYPE: DNA
<213> ORGANISM: Homo sapiens

<400> SEQUENCE: 13

```
ggtcgtgcgc gctgaggagg agccgctgcc gccgtcgccg tcgccgccac cgccgccacc        60
gctaccgagg ccgagcggag ccgttagcgc cgcgccgccg ccgcctcccg cccgccccgg      120
agcagcccg  ggcccgcccg cccgcatcca gattttttgaa aaatacaatg tctaatggtt     180
atgaagacca catggccgaa gactgcaggg gtgacatcgg gagaacgaat ttgatcgtca      240
actacctccc tcagaacatg acccaggatg agttacgaag cctgttcagc agcattggtg      300
aagttgaatc tgcaaaactt attcgggata agtagcagg  acacagcttg gctatggct      360
ttgtgaacta cgtgaccgcg aaggatgcag agagagcgat caacacgctg aacggcttga      420
ggctccagtc aaaaaccatt aaggtgtcgt atgctcgccc gagctcagag gtgatcaaag      480
acgccaactt gtacatcagc gggctcccgc ggaccatgac ccagaaggac gtagaagaca      540
tgttctctcg gtttgggcgg atcatcaact cgcgggtcct cgtggatcag actacaggtt      600
tgtccagagg ggttgcgttt atccggtttg acaaacggtc ggaggcagaa gaggcaatta      660
ccagtttcaa tggtcataaa ccccaggtt  cctctgagcc catcacagtg aagtttgcag     720
ccaaccccaa ccagaacaaa aacgtggcac tcctctcgca gctgtaccac tcgccagcgc      780
gacggttcgg aggccccgtt caccaccagg cgcagagatt caggttctcc cccatgggcg      840
```

```
tcgatcacat gagcgggctc tctggcgtca acgtgccagg aaacgcctcc tccggctggt    900
gcattttcat ctacaacctg ggcaggatg ccgacgaggg gatcctctgg cagatgtttg     960
ggccgtttgg tgccgtcacc aatgtgaaag tgatccgcga cttcaacacc aacaagtgca   1020
aagggtttgg ctttgtgacc atgacaaact atgaagaagc cgcgatggcc atagccagcc   1080
tgaacggcta ccgcctgggg gacaaaatct acaggtttc cttcaaaacc aacaagtccc    1140
acaaataact cgctcatgct ttttttgta cggaatagat aattaagagt gaaggagttg    1200 aaactttct tgttagtgta caactcattt tgcgccaatt tcacaagtg tttgtctttg     1260 tctgaatgag aagtgagaag ttttttatac tctgggatgc aaccgacatg ttcaaatgtt   1320
tgaaatccca caatgttaga ccaatcttaa gtttcgtaag ttatttcctt taagatatat   1380
attaaacaga aatctaagta gaactgcatt gactaaccag tccctctgga tggtggtgaa   1440
cctgaagcat gctttaacct ctaagactgt ctaacacgcg tttcattcaa tgtctccaca   1500
gactgggtag caaaaaaatc acctttagt tttagttttt aatctaaaga tgttagacag    1560
atgctgagtg tgcgttttct caaccgcttc aacattgtaa gcgatgtatg ctttggttga   1620
caggaagttc cttttccagg caggtccgt tgccacctcc tgctcactca gtcccgggct    1680
ctgccgagtg gtcctgggaa tggcggcggg cccgtccagc gtgggccacc actggggccg   1740
ggggccacgg gctgcatgct gggcgggccc tccagagaag gacacaaacg tgtttcgtaa   1800
gcccaggcac caatgggaat ggaccaaaga gtttcaggga aactccagta tattccagag   1860
tcagatctaa gctccaggca cgcctgaaga tgtgttgcta ctctgacatc ccgagttttct  1920 gtccacacat tgcatgcaca gcgccccaca cattggatac tgttgttcac gataatttct   1980
cccgttttcc agagcattta acatagcttg gaggcgtaaa atggctctgt attttaataa   2040
cacagaaaca tttgagcatt gtatttctcg catcccttct cgtgagcgct tagaccttt    2100 tctattttag tcggattttg ttttggaatt ttgcttttgt atgaacactc agcagaaaag   2160
tacttacttc ttgccagtta tctattaacc aaaacctttg atttgtagtt ttaaagatta   2220
accctcaaag ttctcttcat aactgccttg acattttggg ttgttctgtt ctgttaattt   2280
tcttttgctt ttttgtgttt tttgtttgtt tttacttttg catttaagac cattaaattt   2340
gattttgttt tgctcgaat                                                2359
```

<210> SEQ ID NO 14
<211> LENGTH: 4940
<212> TYPE: DNA
<213> ORGANISM: Homo sapiens

<400> SEQUENCE: 14

```
aagttcctgt gttctttatt ctactctccg ctgaagtcca cacagtttaa attaaagttc     60
ccggattttt gtgggcgcct gccccgcccc tcgtcccct gctgtgtcca tatatcgagg     120
cgatagggtt aagggaaggc ggacgcctga tgggttaatg agcaaactga agtgttttcc    180
atgatctttt ttgagtcgca attgaagtac cacctcccga gggtgattgc ttccccatgc    240
ggggtagaac ctttgctgtc ctgttcacca ctctacctcc agcacagaat ttggcttatg    300
cctactcaat gtgaagatga tgaggatgaa aacctttgtg atgatccact tccacttaat    360
gaatggtggc aaagcaaagc tatattcaag accacatgca agctactccc ctgagcaaag    420
agtcacagat aaaacggggg caccagtaga atggccagga caaacgcagt gcagcacaga    480
gactcagacc ctggcagcca tgcctgcgca ggcagtgatg agagtgacat gtactgttgt    540
```

```
ggacatgcac aaaagtgaga tacttcaaag attccagaag atatgccccg ggggtcctgg    600
aagccacaag tgtgcaccgg cacagacatg aagctgcggc tccctgccag tcccgagacc    660
cacctggaca tgctccgcca cctctaccag ggctgccagg tggtgcaggg aaacctggaa    720
ctcacctacc tgcccaccaa tgccagcctg tccttcctgc aggatatcca ggaggtgcag    780
ggctacgtgc tcatcgctca caaccaagtg aggcaggtcc cactgcagag gctgcggatt    840
gtgcgaggca cccagctctt tgaggacaac tatgccctgg ccgtgctaga caatggagac    900
ccgctgaaca ataccacccc tgtcacaggg gcctcccag gaggcctgcg ggagctgcag     960
cttcgaagcc tcacagagat cttgaaagga ggggtcttga tccagcggaa cccccagctc    1020
tgctaccagg acacgatttt gtggaaggac atcttccaca gaacaaccca gctggctctc    1080
acactgatag acaccaaccg ctctcgggcc tgccacccct gttctccgat gtgtaagggc    1140
tcccgctgct ggggagagag ttctgaggat tgtcagagcc tgacgcgcac tgtctgtgcc    1200
ggtggctgtg cccgctgcaa ggggccactg cccactgact gctgccatga gcagtgtgct    1260
gccggctgca cgggccccaa gcactctgac tgcctggcct gcctccactt caaccacagt    1320
ggcatctgtg agctgcactg cccagccctg gtcacctaca acacagacac gtttgagtcc    1380
atgcccaatc ccgagggccg gtatacattc ggcgccagct gtgtgactgc ctgtccctac    1440
aactaccttt ctacggacgt gggatcctgc accctcgtct gccccctgca caaccaagag    1500
gtgacagcag aggatggaac acagcggtgt gagaagtgca gcaagccctg tgcccgagtg    1560
tgctatggtc tgggcatgga gcacttgcga gaggtgaggg cagttaccag tgccaatatc    1620
caggagtttg ctggctgcaa gaagatcttt gggagcctgg catttctgcc ggagagcttt    1680
gatggggacc cagcctccaa cactgccccg ctccagccag agcagctcca agtgtttgag    1740
actctggaag agatcacagg ttacctatac atctcagcat ggccggacag cctgcctgac    1800
ctcagcgtct ccagaacct gcaagtaatc cggggacgaa ttctgcacaa tggcgcctac    1860
tcgctgaccc tgcaagggct gggcatcagc tggctgggc tgcgctcact gagggaactg    1920
ggcagtggac tggccctcat ccaccataac acccacctct gcttcgtgca cacggtgccc    1980
tgggaccagc tctttcggaa cccgcaccaa gctctgctcc acactgccaa ccggccagag    2040
gacgagtgtg tgggcgaggg cctggcctgc caccagctgt gcgcccgagg cactgctgg    2100
ggtccagggc ccacccagtg tgtcaactgc agccagttcc ttcggggcca ggagtgcgtg    2160
gaggaatgcc gagtactgca ggggctcccc agggagtatg tgaatgccag gcactgtttg    2220
ccgtgccacc ctgagtgtca gcccccagaat ggctcagtga cctgttttgg accggaggct    2280
gaccagtgtg tggcctgtgc ccactataag gaccctccct tctgcgtggc ccgctgcccc    2340
agcggtgtga aacctgacct ctcctacatg cccatctgga gtttccaga tgaggagggc    2400
gcatgccagc cttgccccat caactgcacc cactcctgtg tggacctgga tgacaagggc    2460
tgccccgccg agcagagagc cagccctctg acgtccatca tctctgcggt ggttggcatt    2520
ctgctggtcg tggtcttggg ggtggtcttt gggatcctca tcaagcgacg gcagcagaag    2580
atccggaagt acacgatgcg gagactgctg caggaaacgg agctggtgga gccgctgaca    2640
cctagcggag cgatgcccaa ccaggcgcag atgcggatcc tgaaagagac ggagctgagg    2700
aaggtgaagg tgcttggatc tggcgctttt ggcacagtct acaagggcat ctggatccct    2760
gatggggaga atgtgaaaat tccagtggcc atcaaagtgt tgaggaaaaa cacatccccc    2820
aaagccaaca agaaatcttt agacgaagca tacgtgatgg ctggtgtggg ctccccatat    2880
gtctcccgcc ttctgggcat ctgcctgaca tccacggtgc agctggtgac acagcttatg    2940
```

```
cccctatggct gcctcttaga ccatgtccgg gaaaaccgcg gacgcctggg ctcccaggac    3000
ctgctgaact ggtgtatgca gattgccaag gggatgagct acctggagga tgtgcggctc    3060
gtacacaggg acttggccgc tcggaacgtg ctggtcaaga gtcccaacca tgtcaaaatt    3120
acagacttcg ggctggctcg gctgctggac attgacgaga cagagtacca tgcagatggg    3180
ggcaaggtgc ccatcaagtg gatggcgctg gagtccattc tccgccggcg gttcacccac    3240
cagagtgatg tgtggagtta tggtgtgact gtgtgggagc tgatgacttt tggggccaaa    3300
ccttacgatg ggatcccagc ccgggagatc cctgacctgc tggaaaaggg ggagcggctg    3360
ccccagcccc ccatctgcac cattgatgtc tacatgatca tggtcaaatg ttggatgatt    3420
gactctgaat gtcggccaag attccgggag ttggtgtctg aattctcccg catggccagg    3480
gacccccagc gctttgtggt catccagaat gaggacttgg gcccagccag tcccttggac    3540
agcaccttct accgctcact gctggaggac gatgacatgg gggacctggt ggatgctgag    3600
gagtatctgg tacccagca gggcttcttc tgtccagacc ctgccccggg cgctggggc    3660 atggtccacc acaggcaccg cagctcatct accaggagtg gcggtgggga cctgacacta    3720
gggctggagc cctctgaaga ggaggccccc aggtctccac tggcaccctc cgaaggggct    3780
ggctccgatg tatttgatgg tgacctggga atgggggcag ccaaggggct gcaaagcctc    3840
cccacacatg accccagccc tctacagcgg tacagtgagg accccacagt accctgccc    3900 tctgagactg atggctacgt tgcccccctg acctgcagcc cccagcctga atatgtgaac    3960
cagccagatg ttcggcccca gccccccttcg ccccgagagg gccctctgcc tgctgcccga    4020
cctgctggtg ccactctgga aaggcccaag actctctccc cagggaagaa tggggtcgtc    4080
aaagacgttt ttgcctttgg gggtgccgtg gagaaacccg agtacttgac accccaggga    4140
ggagctgccc ctcagcccca ccctcctcct gccttcagcc cagccttcga caacctctat    4200
tactgggacc aggacccacc agagcggggg gctccaccca gcaccttcaa agggacacct    4260
acggcagaga acccagagta cctgggtctg gacgtgccag tgtgaaccag aaggccaagt    4320
ccgcagaagc cctgatgtgt cctcaggag caggaaggc ctgacttctg ctggcatcaa    4380
gaggtgggag ggccctccga ccacttccag gggaacctgc catgccagga acctgtccta    4440
aggaaccttc cttcctgctt gagttcccag atggctggaa ggggtccagc ctcgttggaa    4500
gaggaacagc actgggagt ctttgtggat tctgaggccc tgcccaatga gactctaggg    4560
tccagtggat gccacagccc agcttggccc tttccttcca gatcctgggt actgaaagcc    4620
ttagggaagc tggcctgaga ggggaagcgg ccctaaggga gtgtctaaga acaaaagcga    4680
cccattcaga gactgtccct gaaacctagt actgcccccc atgaggaagg aacagcaatg    4740
gtgtcagtat ccaggctttg tacagagtgc ttttctgttt agttttact ttttttgttt    4800 tgttttttta aagatgaaat aaagacccag ggggagaatg ggtgttgtat ggggaggcaa    4860
gtgtgggggg tccttctcca cacccacttt gtccatttgc aaatatattt tggaaaacag    4920
ctaaaaaaaa aaaaaaaaaa                                               4940
```

<210> SEQ ID NO 15
<211> LENGTH: 6330
<212> TYPE: DNA
<213> ORGANISM: Homo sapiens

<400> SEQUENCE: 15

```
aggagctggc ggagggcgtt cgtcctggga ctgcacttgc tcccgtcggg tcgcccggct      60
```

-continued

```
tcaccggacc cgcaggctcc cggggcaggg ccggggccag agctcgcgtg tcggcgggac    120
atgcgctgcg tcgcctctaa cctcgggctg tgctcttttt ccaggtggcc cgccggtttc    180
tgagccttct gccctgcggg gacacggtct gcaccctgcc cgcggccacg gaccatgacc    240
atgaccctcc acaccaaagc atctgggatg gccctactgc atcagatcca agggaacgag    300
ctggagcccc tgaaccgtcc gcagctcaag atcccctgg agcggcccct gggcgaggtg    360
tacctggaca gcagcaagcc cgccgtgtac aactacccg agggcgccgc ctacgagttc    420
aacgccgcgg ccgccgccaa cgcgcaggtc tacggtcaga ccggcctccc ctacggcccc    480
gggtctgagg ctgcggcgtt cggctccaac ggcctggggg gtttcccccc actcaacagc    540
gtgtctccga gcccgctgat gctactgcac ccgccgccgc agctgtcgcc tttcctgcag    600
ccccacggcc agcaggtgcc ctactacctg gagaacgagc ccagcggcta cacggtgcgc    660
gaggccggcc cgccggcatt ctacaggcca aattcagata tcgacgcca gggtggcaga    720 gaaagattgg ccagtaccaa tgacaaggga agtatggcta tggaatctgc caaggagact    780
cgctactgtg cagtgtgcaa tgactatgct tcaggctacc attatggagt ctggtcctgt    840
gagggctgca aggccttctt caagagaagt attcaaggac ataacgacta tatgtgtcca    900
gccaccaacc agtgcaccat tgataaaaac aggaggaaga gctgccaggc ctgccggctc    960
cgcaaatgct acgaagtggg aatgatgaaa ggtgggatac gaaagaccg aagaggaggg    1020 agaatgttga aacacaagcg ccagagagat gatggggagg cagggggtga agtggggtct    1080
gctggagaca tgagagctgc caacctttgg ccaagcccgc tcatgatcaa acgctctaag    1140
aagaacagct tggccttgtc cctgacggcc gaccagatgg tcagtgcctt gttggatgct    1200 gagccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgacccc catgatcagg tccaccttct agaatgtgcc    1380
tggctagaga tcctgatgat tggtctcgtc tggcgctcca tggagcaccc agggaagcta    1440
ctgtttgctc ctaacttgct cttggacagg aaccagggaa atgtgtaga gggcatggtg    1500 gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
acagacactt tgatccacct gatggccaag gcaggcctga ccctgcagca gcagcaccag    1740
cggctggccc agctcctcct catcctctcc cacatcaggc acatgagtaa caaaggcatg    1800
gagcatctgt acagcatgaa gtgcaagaac gtggtgcccc tctatgacct gctgctggag    1860
atgctggacg cccaccgcct acatgcgccc actagccgtg gagggcatc cgtggaggag    1920 acggaccaaa gccacttggc cactgcgggc tctacttcat cgcattcctt gcaaaagtat    1980
tacatcacgg gggaggcaga gggtttccct gccacggtct gagagctccc tggctcccac    2040
acggttcaga taatccctgc tgcatttac cctcatcatg caccacttta gccaaattct    2100
gtctcctgca tacactccgg catgcatcca acaccaatgg ctttctagat gagtggccat    2160
tcatttgctt gctcagttct tagtggcaca tcttctgtct tctgttggga acagccaaag    2220
ggattccaag gctaaatctt tgtaacagct ctctttcccc cttgctatgt tactaagcgt    2280
gaggattccc gtagctcttc acagctgaac tcagtctatg ggttggggct cagataactc    2340
tgtgcattta agctacttgt agagacccag gcctggagag tagacatttt gcctctgata    2400 agcactttt aaatggctct aagaataagc cacagcaaag aatttaaagt ggctcctttta    2460
```

```
attggtgact tggagaaagc taggtcaagg gtttattata gcaccctctt gtattcctat    2520
ggcaatgcat ccttttatga aagtggtaca ccttaaagct tttatatgac tgtagcagag    2580
tatctggtga ttgtcaattc attccccta taggaataca aggggcacac agggaaggca    2640
gatcccctag ttggcaagac tattttaact tgatacactg cagattcaga tgtgctgaaa    2700
gctctgcctc tggctttccg gtcatgggtt ccagttaatt catgcctccc atggacctat    2760
ggagagcagc aagttgatct tagttaagtc tccctatatg agggataagt tcctgatttt    2820
tgtttttatt tttgtgttac aaaagaaagc cctccctccc tgaacttgca gtaaggtcag    2880
cttcaggacc tgttccagtg ggcactgtac ttggatcttc ccggcgtgtg tgtgccttac    2940 acagggtga actgttcact gtggtgatgc atgatgaggg taaatggtag ttgaaaggag     3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggtg ccctgggatc cctggggtag tccagctctt    3240
cttcatttcc cagcgtggcc ctggttggaa gaagcagctg tcacagctgc tgtagacagc    3300
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgcccgt    3480 tccctaccgc ctccactcct gccagctcat tccttcaat ttcctttgac ctataggcta    3540 aaaagaaag gctcattcca gccacagggc agccttccct gggcctttgc ttctctagca    3600
caattatggg ttacttcctt tttcttaaca aaaagaatg tttgatttcc tctgggtgac    3660
cttattgtct gtaattgaaa ccctattgag aggtgatgtc tgtgttagcc aatgacccag    3720
gtgagctgct cgggcttctc ttggtatgtc ttgtttggaa aagtggattt cattcatttc    3780
tgattgtcca gttaagtgat caccaaagga ctgagaatct gggagggcaa aaaaaaaaa    3840 aaagttttta tgtgcactta aatttgggga caatttatg tatctgtgtt aaggatatgt    3900
ttaagaacat aattcttttg ttgctgtttg tttaagaagc accttagttt gtttaagaag    3960
caccttatat agtataatat atattttttt gaaattacat tgcttgttta tcagacaatt    4020
gaatgtagta attctgttct ggatttaatt tgactgggtt aacatgcaaa aaccaaggaa    4080
aaatatttag tttttttttt tttttttgta tacttttcaa gctaccttgt catgtataca    4140
gtcatttatg cctaaagcct ggtgattatt catttaaatg aagatcacat ttcatatcaa    4200
cttttgtatc cacagtagac aaaatagcac taatccagat gcctattgtt ggatactgaa    4260
tgacagacaa tcttatgtag caaagattat gcctgaaaag gaaattatt cagggcagct    4320 aattttgctt ttaccaaat atcagtagta atatttttgg acagtagcta atgggtcagt    4380
gggttctttt taatgtttat acttagattt tcttttaaaa aaattaaaat aaaacaaaaa    4440
aaaatttcta ggactagacg atgtaatacc agctaaagcc aaacaattat acagtggaag    4500
gttttacatt attcatccaa tgtgtttcta ttcatgttaa gatactacta catttgaagt    4560
gggcagagaa catcagatga ttgaaatgtt cgcccagggg tctccagcaa ctttggaaat    4620
ctctttgtat ttttacttga agtgccacta atggacagca gatatttct ggctgatgtt    4680 ggtattgggt gtaggaacat gatttaaaaa aaaactcttg cctctgcttt cccccactct    4740
gaggcaagtt aaaatgtaaa agatgtgatt tatctggggg gctcaggtat ggtggggaag    4800
```

```
tggattcagg aatctgggga atggcaaata tattaagaag agtattgaaa gtatttggag    4860
gaaaatggtt aattctgggt gtgcaccagg gttcagtaga gtccacttct gccctggaga    4920
ccacaaatca actagctcca tttacagcca tttctaaaat ggcagcttca gttctagaga    4980
agaaagaaca acatcagcag taaagtccat ggaatagcta gtggtctgtg tttcttttcg    5040
ccattgccta gcttgccgta atgattctat aatgccatca tgcagcaatt atgagaggct    5100
aggtcatcca aagagaagac cctatcaatg taggttgcaa aatctaaccc ctaaggaagt    5160
gcagtctttg atttgatttc cctagtaacc ttgcagatat gtttaaccaa gccatagccc    5220 atgcctttg agggctgaac aaataaggga cttactgata atttacttttt gatcacatta    5280 aggtgttctc accttgaaat cttatacact gaaatggcca ttgatttagg ccactggctt    5340
agagtactcc ttccctgca tgacactgat tacaaatact ttcctattca tactttccaa    5400
ttatgagatg gactgtgggt actgggagtg atcactaaca ccatagtaat gtctaatatt    5460
cacaggcaga tctgcttggg gaagctagtt atgtgaaagg caaatagagt catacagtag    5520
ctcaaaaggc aaccataatt ctctttggtg caggtcttgg gagcgtgatc tagattacac    5580
tgcaccattc ccaagttaat cccctgaaaa cttactctca actggagcaa atgaactttg    5640
gtcccaaata tccatctttt cagtagcgtt aattatgctc tgtttccaac tgcatttcct    5700
ttccaattga attaaagtgt ggcctcgttt ttagtcattt aaaattgttt tctaagtaat    5760
tgctgcctct attatggcac ttcaattttg cactgtcttt tgagattcaa gaaaaatttc    5820 tattctttt tttgcatcca attgtgcctg aacttttaaa atatgtaaat gctgccatgt    5880
tccaaaccca tcgtcagtgt gtgtgtttag agctgtgcac cctagaaaca acatattgtc    5940
ccatgagcag gtgcctgaga cacagacccc tttgcattca cagagaggtc attggttata    6000
gagacttgaa ttaataagtg acattatgcc agtttctgtt ctctcacagg tgataaacaa    6060
tgctttttgt gcactacata ctcttcagtg tagagctctt gttttatggg aaaaggctca    6120
aatgccaaat tgtgtttgat ggattaatat gccctttgc cgatgcatac tattactgat    6180
gtgactcggt tttgtcgcag ctttgctttg tttaatgaaa cacacttgta aacctctttt    6240
gcactttgaa aaagaatcca gcgggatgct cgagcacctg taaacaattt tctcaaccta    6300
tttgatgttc aaataaagaa ttaaactaaa                                    6330
```

<210> SEQ ID NO 16
<211> LENGTH: 11981
<212> TYPE: DNA
<213> ORGANISM: Homo sapiens

<400> SEQUENCE: 16

```
agctgaaggc aaagggtccc cgggctcccc acgtggcggg cggccgcc tcccccgagg      60 tcggatcccc actgctgtgt cgcccagccg caggtccgtt cccggggagc cagacctcgg    120
acaccttgcc tgaagtttcg gccataccta tctccctgga cgggctactc ttccctcggc    180
cctgccaggg acaggacccc tccgacgaaa agacgcagga ccagcagtcg ctgtcggacg    240
tggagggcgc atattccaga gctgaagcta caaggggtgc tggaggcagc agttctagtc    300
ccccagaaaa ggacagcgga ctgctggaca gtgtcttgga cactctgttg gcgccctcag    360
gtcccgggca gagccaaccc agccctcccg cctgcgaggt caccagctct tggtgcctgt    420
ttggccccga acttcccgaa gatccaccgg ctgcccccgc cacccagcgg gtgttgtccc    480
cgctcatgag ccggtccggg tgcaaggttg agacagctc cggacgggca gctgccata    540 aagtgctgcc ccggggcctg tcaccagccc ggcagctgct gctcccggcc tctgagagcc    600
```

```
ctcactggtc cggggcccca gtgaagccgt ctccgcaggc cgctgcggtg gaggttgagg      660
aggaggatgg ctctgagtcc gaggagtctg cgggtccgct tctgaagggc aaacctcggg      720
ctctgggtgg cgcggcggct ggaggaggag ccgcggctgt cccgccgggg gcggcagcag      780
gaggcgtcgc cctggtcccc aaggaagatt cccgcttctc agcgcccagg gtcgccctgg      840
tggagcagga cgcgccgatg gcgcccgggc gctccccgct ggccaccacg gtgatggatt      900
tcatccacgt gcctatcctg cctctcaatc acgccttatt ggcagcccgc actcggcagc      960
tgctggaaga cgaaagttac gacggcgggg ccggggctgc cagcgccttt gccccgccgc     1020
ggagttcacc ctgtgcctcg tccaccccgg tcgctgtagg cgacttcccc gactgcgcgt     1080
acccgcccga cgccgagccc aaggacgacg cgtaccctct ctatagcgac ttccagccgc     1140
ccgctctaaa gataaggag gaggaggaag gcgcggaggc ctccgcgcgc tccccgcgtt      1200
cctaccttgt ggccggtgcc aaccccgcag ccttcccgga tttccgttg gggccaccgc      1260
ccccgctgcc gccgcgagcg accccatcca gacccgggga gcggcggtg acggccgcac      1320
ccgccagtgc ctcagtctcg tctgcgtcct cctcggggtc gaccctggag tgcatcctgt     1380
acaaagcgga gggcgcgccg ccccagcagg gcccgttcgc gccgccgccc tgcaaggcgc     1440
cgggcgcgag cggctgcctg ctcccgcggg acggcctgcc ctccacctcc gcctctgccg     1500
ccgccgccgg ggcggccccc gcgctctacc ctgcactcgg cctcaacggg ctcccgcagc     1560
tcggctacca ggccgccgtg ctcaaggagg gcctgccgca ggtctacccg ccctatctca     1620
actacctgag gccggattca gaagccagcc agagcccaca atacagcttc gagtcattac     1680
ctcagaagat ttgtttaatc tgtggggatg aagcatcagg ctgtcattat ggtgtcctta     1740
cctgtgggag ctgtaaggtc ttctttaaga gggcaatgga agggcagcac aactacttat     1800
gtgctggaag aaatgactgc atcgttgata aaatccgcag aaaaaactgc ccagcatgtc     1860
gccttagaaa gtgctgtcag gctggcatgg tccttggagg ttttcgaaac ttacatattg     1920
atgaccagat aactctcatt cagtattctt ggatgagctt aatggtgttt ggtctaggat     1980
ggagatccta caaacacgtc agtgggcaga tgctgtattt tgcacctgat ctaatactaa     2040
atgaacagcg gatgaaagaa tcatcattct attcattatg ccttaccatg tggcagatcc     2100
cacaggagtt tgtcaagctt caagttagcc aagaagagtt cctctgtatg aaagtattgt     2160
tacttcttaa tacaattcct ttggaagggc tacgaagtca aacccagttt gaggagatga     2220
ggtcaagcta cattagagag ctcatcaagg caattggttt gaggcaaaaa ggagttgtgt     2280
cgagctcaca gcgtttctat caacttacaa aacttcttga taacttgcat gatcttgtca     2340
aacaacttca tctgtactgc ttgaatacat ttatccagtc ccgggcactg agtgttgaat     2400
ttccagaaat gatgtctgaa gttattgctg cacaattacc caagatattg gcagggatgg     2460
tgaaacccct tctctttcat aaaaagtgaa tgtcatcttt ttcttttaaa gaattaaatt     2520
ttgtggtatg tcttttgtt ttggtcagga ttatgaggtc ttgagtttt ataatgttct      2580
tctgaaagcc ttacatttat aacatcatag tgtgtaaatt taaagaaaa attgtgaggt     2640
tctaattatt ttcttttata agtataatt agaatgttta actgttttgt ttacccatat      2700
tttcttgaag aatttacaag attgaaaaag tactaaaatt gttaaagtaa actatcttat     2760
ccatattatt tcataccatg taggtgagga ttttaactt tgcatctaa caaatcatcg       2820
acttaagaga aaaatcttta catgtaataa cacaaagcta ttatatgtta tttctaggta     2880
actccctttg tgtcaattat atttccaaaa atgaaccttt aaaatggtat gcaaaatttt     2940
```

```
gtctatatat atttgtgtga ggaggaaatt cataactttc ctcagatttt caaaagtatt    3000
tttaatgcaa aaaatgtaga aagagtttaa aaccactaaa atagattgat gttcttcaaa    3060
ctaggcaaaa caactcatat gttaagacca ttttccagat tggaaacaca aatctcttag    3120
gaagttaata agtagattca tatcattatg caaatagtat tgtgggtttt gtaggttttt    3180
aaaataacct tttttgggga gagaattgtc ctctaatgag gtattgcgag tggacataag    3240
aaatcagaag attatggcct aactgtactc cttaccaact gtggcatgct gaaagttagt    3300
cactcttact gattctcaat tctctcacct ttgaaagtag taaaatatct ttcctgccaa    3360
ttgctccttt gggtcagagc ttattaacat cttttcaaat caaggaaag aagaaaggga    3420 gaggaggagg agggaggtat caattcacat acctttctcc tctttatcct ccactatcat    3480
gaattcatat tatgtttcag ccatgcaaat cttttttacca tgaaatttct tccagaattt    3540
tccccctttg acacaaattc catgcatgtt tcaaccttcg agactcagcc aaatgtcatt    3600
tctgtaaaat cttccctgag tcttccaagc agtaatttgc cttctcctag agtttacctg    3660
ccattttgtg cacatttgag ttacagtagc atgttatttt acaattgtga ctctcctggg    3720
agtctgggag ccatataaag tggtcaatag tgtttgctga ctgagagttg aatgacattt    3780
tctctctgtc ttggtattac tgtagatttc gatcattctt tggttacatt tctgcatatt    3840
tctgtaccca tgactttatc actttcttct cccatgcttt atctccatca attatcttca    3900
ttacttttaa attttccacc tttgcttcct actttgtgag atctctccct ttactgacta    3960
taacatagaa gaatagaagt gtattttatg tgtcttaagg acaatacttt agattccttg    4020
ttctaagttt taaactgaa tgaatggaat attatttctc tccctaagca aaattccaca    4080
aaacaattat ttcttatgtt tatgtagcct taaattgttt tgtactgtaa acctcagcat    4140
aaaaactttc ttcatttcta atttcattca acaaatattg attgaatacc tggtattagc    4200
acaagaaaaa tgtgctaata agccttatga gaatttggag ctgaagaaag acatataact    4260
caggaaagtt acagtccagt agtaggtata aattacagtg cctgataaat aggcatttta    4320
atatttgtac actcaacgta tactaggtag gtgcaaaaca tttacatata atttttactga    4380 tacccatgca gcacaaaggt actaacttta aatattaaat aacacccttta tgtgtcagta    4440 attcatttgc attaaatctt attgaaaagg ctttcaatat attttcccca caaatgtcat    4500
cccaagaaaa aagtattttt aacatctccc aaatataata gttacaggaa atctacctct    4560
gtgagagtga cacctctcag aatgaactgt gtgacacaag aaaatgaatg taggtctatc    4620
caaaaaaaac cccaagaaac aaaaacaata ttattagccc tttatgctta agtgatggac    4680
tcagggaaca gttgatgttg tgatcatttt attatctgat tcttgttact ttgaattaaa    4740
ccaatatttt gatgatataa atcatttcca ccagcatata tttaatttcc ataataactt    4800
taaaattttc taatttcact caactatgag ggaatagaat gtggtggcca caggtttggc    4860
ttttgttaaa atgtttgata tcttcgatgt tgatctctgt ctgcaatgta gatgtctaaa    4920
cactaggatt taatatttaa ggctaagctt taaaaataaa gtaccttttt aaaaagaata    4980
tggcttcacc aaatggaaaa tacctaattt ctaaatcttt ttctctacaa agtcctatct    5040
actaatgtct ccattactat ttagtcatca taaccattat cttcatttta catgtcgtgt    5100
tctttctggt agctctaaaa tgacactaaa tcataagaag acaggttaca tatcaggaaa    5160
tacttgaagg ttactgaaat agattcttga gttaatgaaa atattttctg taaaaaggtt    5220
tgaaaagcca tttgagtcta aagcattata cctccattat cagtagttat gtgacaattg    5280
tgtgtgtgtt taatgtttaa agatgtggca cttttttaata aggcaatgct atgctatttt    5340
```

```
ttcccattta acattaagat aatttattgc tatacagatg atatggaaat atgatgaaca    5400 atatttttt tgccaaaact atgccttgta agtagccatg gaatgtcaac ctgtaactta    5460
aattatccac agatagtcat gtgtttgatg atgggcactg tggagataac tgacatagga    5520
ctgtgccccc cttctctgcc acttactagc tggatgagat taagcaagtc atttaactgc    5580
tctgattaaa cctgcctttc ccaagtgctt tgtaatgaat agaaatggaa accaaaaaaa    5640
acgtatacag gccttcagaa atagtaattg ctactatttt gttttcatta agccatagtt    5700
ctggctataa ttttatcaaa ctcaccagct atattctaca gtgaaagcag gattctagaa    5760
agtctcactg ttttatttat gtcaccatgt gctatgatat atttggttga attcatttga    5820
aattagggct ggaagtattc aagtaatttc ttctgctgaa aaaatacagt gttttgagtt    5880
tagggcctgt tttatcaaag ttctaaagag cctatcactc ttccattgta gacattttaa    5940
aataatgaca ctgattttaa cattttttaag tgtcttttta gaacagagag cctgactaga    6000
acacagcccc tccaaaaacc catgctcaaa ttattttttac tatggcagca attccacaaa    6060
agggaacaat gggtttagaa attacaatga agtcatcaac ccaaaaaaca tccctatccc    6120
taagaaggtt atgatataaa atgcccacaa gaaatctatg tctgctttaa tctgtctttt    6180
attgctttgg aaggatggct attacatttt tagttttgc tgtgaatacc tgagcagttt    6240
ctctcatcca tacttatcct tcacacatca gaagtcagga tagaatatga atcattttaa    6300
aaacttttac aactccagag ccatgtgcat aagaagcatt caaaacttgc caaaacatac    6360
attttttttc aaatttaaag atactctatt tttgtattca atagctcaac aactgtggtc    6420
cccactgata aagtgaagtg gacaaggaga caagtaatgg cataagtttg ttttttcccaa    6480 agtatgcctg ttcaatagcc attggatgtg ggaaatttct acatctctta aaattttaca    6540
gaaaatacat agccagatag tctagcaaaa gttcaccaag tcctaaattg cttatcctta    6600
cttcactaag tcatgaaatc attttaatga aaagaacatc acctaggttt tgtggttttct   6660 ttttttctta ttcatggctg agtgaaaaca acaatctctg tttctcccta gcatctgtgg    6720
actatttaat gtaccattat tccacactct atggtcctta ctaaatacaa aattgaacaa    6780
aaagcagtaa aacaactgac tcttcaccca tattataaaa tataatccaa gccagattag    6840
tcaacatcca taagatgaat ccaagctgaa ctgggcctag attattgagt tcaggttgga    6900
tcacatccct atttattaat aaacttagga agaaggcct tacagaccat cagttagctg     6960
gagctaatag aacctacact tctaaagttc ggcctagaat caatgtggcc ttaaaagctg    7020
aaaagaagca ggaaagaaca gttttcttca ataatttgtc caccctgtca ctggagaaaa    7080
tttaagaatt tgggggtgtt ggtagtaagt taaacacagc agctgttcat ggcagaaatt    7140
attcaataca taccttctct gaatatccta taaccaaagc aaagaaaaac accaggggt    7200 ttgttctcct ccttggagtt gacctcattc caaggcagag ctcaggtcac aggcacaggg    7260
gctgcgccca agcttgtccg cagccttatg cagctgtgga gtctggaaga ctgttgcagg    7320
actgctggcc tagtcccaga atgtcagcct cattttcgat ttactggctc ttgttgctgt    7380
atgtcatgct gaccttattg ttaaacacag gtttgtttgc tttttttcca ctcatggaga    7440
catgggagag gcattatttt taagctggtt gaaagcttta accgataaag cattttaga    7500 gaaatgtgaa tcaggcagct aagaaagcat actctgtcca ttacggtaaa gaaaatgcac    7560
agattattaa ctctgcagtg tggcattagt gtccctggtca atattcggat agatatgaat    7620
aaaatattta aatggtattg taaatagttt tcaggacata tgctatagct tatttttatt    7680
```

```
atcttttgaa attgctctta atacatcaaa tcctgatgta ttcaatttat cagatataaa    7740
ttattctaaa tgaagcccag ttaaatgttt ttgtcttgtc agttatatgt taagtttctg    7800
atctctttgt ctatgacgtt tactaatctg cattttact gttatgaatt attttagaca    7860
gcagtggttt caagctttt gccactaaaa atacctttta ttttctcctc ccccagaaaa    7920
gtctatacct tgaagtatct atccaccaaa ctgtacttct attaagaaat agttattgtg    7980
ttttcttaat gttttgttat tcaaagacat atcaatgaaa gctgctgagc agcatgaata    8040
acaattatat ccacacagat ttgatatatt ttgtgcagcc ttaacttgat agtataaaat    8100
gtcattgctt tttaaataat agttagtcaa tggacttcta tcatagcttt cctaaactag    8160
gttaagatcc agagctttgg ggtcataata tattacatac aattaagtta tctttttcta    8220
agggctttaa aattcatgag aataaccaaa aaggtatgt ggagagttaa tacaaacata    8280
ccatattctt gttgaaacag agatgtggct ctgcttgttc tccataaggt agaaatactt    8340
tccagaattt gcctaaacta gtaagccctg aatttgctat gattagggat aggaagagat    8400
tttcacatgg cagactttag aattcttcac tttagccagt aaagtatctc cttttgatct    8460
tagtattctg tgtatttaa cttttctgag ttgtgcatgt ttataagaaa aatcagcaca    8520
aagggtttaa gttaaagcct ttttactgaa atttgaaaga aacagaagaa aatatcaaag    8580
ttctttgtat tttgagagga ttaaatatga tttacaaaag ttacatggag ggctctctaa    8640
aacattaaat taattatttt ttgttgaaaa gtcttacttt aggcatcatt ttattcctca    8700
gcaactagct gtgaagcctt tactgtgctg tatgccagtc actctgctag attgtggaga    8760
ttaccagtgt tcccgtcttc tccgagctta gagttggatg gggaataaag acaggtaaac    8820
agatagctac aatattgtac tgtgaatgct tatgctggag gaagtacagg gaactattgg    8880
agcacctaag aggagcacct accttgaatt taggggttag cagaggcatc ctgaaaaaag    8940
tcaaagctaa gccacaatct ataagcagtt taggaattag cagaacgtgc gtggtgagga    9000
gatgccaaag gcaagaagag aagagtattc caaacaggag ggattccaaa gagagaagag    9060
tatcccaaac aacatttgca caaacctgat ggggagagag aatgtggggt ggggatggat    9120
gatgagactg aagaagaaag ccaggtctag ataatcagtg gccttgtaca ccatgttaaa    9180
gagtgtagac ttgattctgt tgtaaacagg aaagcagcac aattcatatg aatattttag    9240
aagactccca ctggaatatg gagaataaag ttggagatga ctaatcctgg aagcagggag    9300 aacattttg aggaagttgc actattttgg tgaaaatgat gatcataaac atgaagaatt    9360
gtaggtgatc atgacctcct ctctaatttt ccagaagggt tttggaagat ataacatagg    9420
aacattgaca ggactgacga aaggagatga aatacaccat ataaattgtc aaacacaagg    9480
ccagatgtct aattattttg cttatgtgtt gaaattacaa attttttcatc aggaaaccaa    9540 aaactacaaa acttagtttt cccaagtccc agaattctat ctgtccaaac aatctgtacc    9600
actccaccta tatccctacc tttgcatgtc tgtccaacct caaagtccag gtctatacac    9660
acgggtaaga ctagagcagt tcaagtttca gaaaatgaga aagaggaact gagttgtgct    9720
gaacccatac aaaataaaca cattctttgt atagattctt ggaacctcga gaggaattca    9780
cctaactcat aggtatttga tggtatgaat ccatggctgg gctcggcttt taaaaagcct    9840
tatctgggat tccttctatg gaaccaagtt ccatcaaagc ccatttaaaa gcctacatta    9900
aaaacaaaat tcttgctgca ttgtatacaa ataatgatgt catgatcaaa taatcagatg    9960
ccattatcaa gtggaattac aaaatggtat acccactcca aaaaaaaaa aaaagctaaa   10020 ttctcagtag aacattgtga cttcatgagc cctccacagc cttggagctg aggagggagc   10080
```

| | |
|---|---|
| actggtgagc agtaggttga agagaaaact tggcgcttaa taatctatcc atgtttttc | 10140 |
| atctaaaaga gccttctttt tggattacct tattcaattt ccatcaagga aattgttagt | 10200 |
| tccactaacc agacagcagc tgggaaggca gaagcttact gtatgtacat ggtagctgtg | 10260 |
| ggaaggaggt ttctttctcc aggtcctcac tggccataca ccagtccctt gttagttatg | 10320 |
| cctggtcata gaccccgtt gctatcatct catatttaag tctttggctt gtgaatttat | 10380 |
| ctattctttc agcttcagca ctgcagagtg ctgggacttt gctaacttcc atttcttgct | 10440 |
| ggcttagcac attcctcata ggcccagctc ttttctcatc tggccctgct gtggagtcac | 10500 |
| cttgcccctt caggagagcc atggcttacc actgcctgct aagcctccac tcagctgcca | 10560 |
| ccacactaaa tccaagcttc tctaagatgt tgcagacttt acaggcaagc ataaaaggct | 10620 |
| tgatcttcct ggacttccct ttacttgtct gaatctcacc tccttcaact ttcagtctca | 10680 |
| gaatgtaggc atttgtcctc tttgccctac atcttcctc ttctgaatca tgaaagcctc | 10740 |
| tcacttcctc ttgctatgtg ctggaggctt ctgtcaggtt ttagaatgag ttctcatcta | 10800 |
| gtcctagtag cttttgatgc ttaagtccac cttttaagga tacctttgag atttagacca | 10860 |
| tgttttcgc ttgagaaagc cctaatctcc agacttgcct ttctgtggat ttcaaagacc | 10920 |
| aactgaggaa gtcaaaagct gaatgttgac tttctttgaa catttccgct ataacaattc | 10980 |
| caattctcct cagagcaata tgcctgcctc caactgacca ggagaaaggt ccagtgccaa | 11040 |
| agagaaaaac acaaagatta attatttcag ttgagcacat actttcaaag tggtttgggt | 11100 |
| attcatatga ggttttctgt caagagggtg agactcttca tctatccatg tgtgcctgac | 11160 |
| agttctcctg gcactggctg gtaacagatg caaaactgta aaaattaagt gatcatgtat | 11220 |
| tttaacgata tcatcacata cttatttct atgtaatgtt ttaaatttcc cctaacatac | 11280 |
| tttgactgtt ttgcacatgg tagatattca catttttttg tgttgaagtt gatgcaatct | 11340 |
| tcaaagttat ctaccccgtt gcttattagt aaaactagtg ttaatacttg caagagatg | 11400 |
| cagggaatct ttctcatgac tcacgcccta tttagttatt aatgctacta ccctattttg | 11460 |
| agtaagtagt aggtccctaa gtacattgtc cagagttata cttttaaaga tatttagccc | 11520 |
| catatacttc ttgaatctaa agtcatacac cttgctcctc atttctgagt gggaaagaca | 11580 |
| tttgagagta tgttgacaat tgttctgaag gttttttgcca agaaggtgaa actgtccttt | 11640 |
| catctgtgta tgcctggggc tgggtccctg gcagtgatgg ggtgacaatg caaagctgta | 11700 |
| aaaactaggt gctagtgggc acctaatatc atcatcatat acttattttc aagctaatat | 11760 |
| gcaaaatccc atctctgttt ttaaactaag tgtagatttc agagaaaata ttttgtggtt | 11820 |
| cacataagaa aacagtctac tcagcttgac aagtgtttta tgttaaattg gctggtggtt | 11880 |
| tgaaatgaat catcttcaca taatgttttc tttaaaaata ttgtgaattt aactctaatt | 11940 |
| cttgttattc tgtgtgataa taaagaataa actaatttct a | 11981 |

<210> SEQ ID NO 17
<211> LENGTH: 1455
<212> TYPE: DNA
<213> ORGANISM: Homo sapiens

<400> SEQUENCE: 17

| | |
|---|---|
| ggcaccgcag gccccgggat gctagtgcgc agcgggtgca tccctgtccg gatgctgcgc | 60 |
| ctgcggtaga gcgccgcca tgttgcaacc gggaaggaaa tgaatgggca gccgttagga | 120 |
| aagcctgccg gtgactaacc ctgcgctcct gcctcgatgg gtggagtcgc gtgtggcggg | 180 |

```
gaagtcaggt ggagcgaggc tagctggccc gatttctcct ccgggtgatg cttttcctag    240
attattctct gatttggtcg tattgggcgc ctggtcacca gggctgcttt taactctggt    300
aaagtggata ttgttgccat caatgacccc ttcattgacc tcaactacat ggtttacatg    360
ttccaatatg attccaccca tggcaaattc catggcaccg tcaaggctga aacgggaag     420 cttgtcatca atggaaatcc catcaccatc ttccaggagc gagatccctc caaaatcaag    480
tggggcgatg ctggcgctga gtacgtcgtg gagtccactg gcgtcttcac caccatggag    540
aaggctgggg ctcatttgca gggggagcc aaaagggtca tcatctctgc ccctctgct     600 gatgccccca tgttcgtcat gggtgtgaac catgagaagt atgacaacag cctcaagatc    660
atcagcaatg cctcctgcac caccaactgc ttagcacccc tggccaaggt catccatgac    720
aactttggta tcgtggaagg actcatgacc acagtccatg ccatcactgc cacccagaag    780
actgtggatg gcccctccgg gaaactgtgg cgtgatggcc gcgggctct ccagaacatc     840 atccctgcct ctactggcgc tgccaaggct gtgggcaagg tcatccctga gctgaacggg    900
aagctcactg gcatggcctt ccgtgtcccc actgccaacg tgtcagtggt ggacctgacc    960
tgccgtctag aaaaacctgc caaatatgat gacatcaaga aggtggtgaa gcaggcgtcg   1020
gagggccccc tcaagggcat cctgggctac actgagcacc aggtggtctc ctctgacttc   1080
aacagcgaca cccactcctc cacctttgac gctggggctg gcattgccct caacgaccac   1140
tttgtcaagc tcatttcctg gtatgacaac gaatttggct acagcaacag ggtggtggac   1200
ctcatggccc acatggcctc caaggagtaa gaccctgga ccaccagccc cagcaagagc    1260
acaagaggaa gagagagacc ctcactgctg gggagtccct gccacactca gtcccccacc   1320
acactgaatc tcccctcctc acagttgcca tgtagacccc ttgaagaggg gagggggccta  1380 gggagccgca ccttgtcatg taccatcaat aaagtaccct gtgctcaacc agttaaaaaa   1440
aaaaaaaaaa aaaaa                                                    1455

<210> SEQ ID NO 18
<211> LENGTH: 2321
<212> TYPE: DNA
<213> ORGANISM: Homo sapiens

<400> SEQUENCE: 18
gtcctcaacc aagatggcgc ggatggcttc aggcgcatca cgacaccggc gcgtcacgcg     60
acccgcccta cgggcacctc ccgcgctttt cttagcgccg cagacggtgg ccgagcgggg    120
gaccgggaag catggcccgg gggtcggcgg ttgcctgggc ggcgctcggg ccgttgttgt    180
ggggctgcgc gctggggctg cagggcggga tgctgtaccc ccaggagagc ccgtcgcggg    240
agtgcaagga gctggacggc ctctggagct tccgcgccga cttctctgac aaccgacgcc    300
ggggcttcga ggagcagtgg taccggcggc cgctgtggga gtcaggcccc accgtggaca    360
tgccagttcc ctccagcttc aatgacatca gccaggactg gcgtctgcgg catttttgtcg   420 gctgggtgtg gtacgaacgg gaggtgatcc tgccggagca atggacccag gacctgcgca    480
caagagtggt gctgaggatt ggcagtgccc attcctatgc catcgtgtgg gtgaatgggg   540
tcgacacgct agagcatgag gggggctacc tccccttcga ggccgacatc agcaacctgg    600
tccaggtggg gcccctgccc tccggctcc gaatcactat cgccatcaac aacacactca    660
cccccaccac cctgccacca gggaccatcc aatacctgac tgacacctcc aagtatccca    720
agggttactt tgtccagaac acatattttg actttttcaa ctacgctgga ctgcagcggt    780
ctgtacttct gtacacgaca cccaccacct acatcgatga catcaccgtc accaccagcg    840
```

```
tggagcaaga cagtgggctg gtgaattacc agatctctgt caagggcagt aacctgttca    900
agttggaagt gcgtctttg gatgcagaaa acaaagtcgt ggcgaatggg actgggaccc    960
agggccaact taaggtgcca ggtgtcagcc tctggtggcc gtacctgatg cacgaacgcc   1020
ctgcctatct gtattcattg gaggtgcagc tgactgcaca gacgtcactg gggcctgtgt   1080
ctgacttcta cacactccct gtggggatcc gcactgtggc tgtcaccaag agccagttcc   1140
tcatcaatgg gaaacctttc tatttccacg gtgtcaacaa gcatgaggat gcggacatcc   1200
gagggaaggg cttcgactgg ccgctgctgg tgaaggactt caacctgctt cgctggcttg   1260
gtgccaacgc tttccgtacc agccactacc cctatgcaga ggaagtgatg cagatgtgtg   1320
accgctatgg gattgtggtc atcgatgagt gtcccggcgt gggcctggcg ctgccgcagt   1380
tcttcaacaa cgtttctctg catcaccaca tgcaggtgat ggaagaagtg gtgcgtaggg   1440
acaagaacca ccccgcggtc gtgatgtggt ctgtggccaa cgagcctgcg tcccacctag   1500
aatctgctgg ctactacttg aagatggtga tcgctcacac caaatccttg gaccccctccc  1560
ggcctgtgac ctttgtgagc aactctaact atgcagcaga caaggggggct ccgtatgtgg  1620
atgtgatctg tttgaacagc tactactctt ggtatcacga ctacgggcac ctggagttga  1680
ttcagctgca gctggccacc cagtttgaga actggtataa aagtatcag aagcccatta   1740
ttcagagcga gtatggagca gaaacgattg cagggtttca ccaggatcca cctctgatgt  1800
tcactgaaga gtaccagaaa agtctgctag agcagtacca tctgggtctg gatcaaaaac   1860
gcagaaaata cgtggttgga gagctcattt ggaattttgc cgatttcatg actgaacagt  1920
caccgacgag agtgctgggg aataaaaagg ggatcttcac tcggcagaga caaccaaaaa  1980
gtgcagcgtt cctttttgcga gagagatact ggaagattgc caatgaaacc aggtatcccc   2040
actcagtagc caagtcacaa tgtttggaaa acagcctgtt tacttgagca agactgatac   2100
cacctgcgtg tcccttcctc cccgagtcag ggcgacttcc acagcagcag aacaagtgcc   2160
tcctggactg ttcacggcag accagaacgt ttctggcctg ggttttgtgg tcatctattc   2220
tagcagggaa cactaaaggt ggaaataaaa gattttctat tatgaaata aagagttggc   2280
atgaaagtgg ctactgaaaa aaaaaaaaaa aaaaaaaaa a                         2321
```

<210> SEQ ID NO 19
<211> LENGTH: 1229
<212> TYPE: DNA
<213> ORGANISM: Homo sapiens

<400> SEQUENCE: 19

```
gtctgacggg cgatggcgca gccaatagac aggagcgcta tccgcggttt ctgattggct     60
actttgttcg cattataaaa ggcacgcgcg ggcgcgaggc ccttctctcg ccaggcgtcc    120
tcgtggaagt gacatcgtct ttaaaccctg cgtggcaatc cctgacgcac cgccgtgatg   180
cccagggaag acaggggcgac ctggaagtcc aactacttcc ttaagatcat ccaactattg   240
gatgattatc cgaaatgttt cattgtggga gcagacaatg tgggctccaa gcagatgcag  300
cagatccgca tgtcccttcg cgggaaggct gtggtgctga tgggcaagaa ccaccatgatg  360
cgcaaggcca tccgagggca cctggaaaac aacccagctc tggagaaact gctgcctcat   420
atccggggga atgtgggctt tgtgttcacc aaggaggacc tcactgagat cagggacatg   480
ttgctggcca ataaggtgcc agctgctgcc cgtgctggtg ccattgcccc atgtgaagtc   540
actgtgccag cccagaacac tggtctcggg cccgagaaga cctcctttt ccaggcttta    600
```

| | |
|---|---:|
| ggtatcacca ctaaaatctc caggggcacc attgaaatcc tgagtgatgt gcagctgatc | 660 |
| aagactggag acaaagtggg agccagcgaa gccacgctgc tgaacatgct caacatctcc | 720 |
| cccttctcct ttgggctggt catccagcag gtgttcgaca atggcagcat ctacaaccct | 780 |
| gaagtgcttg atatcacaga ggaaactctg cattctcgct tcctggaggg tgtccgcaat | 840 |
| gttgccagtg tctgtctgca gattggctac ccaactgttg catcagtacc ccattctatc | 900 |
| atcaacgggt acaaacgagt cctggccttg tctgtggaga cggattacac cttcccactt | 960 |
| gctgaaaagg tcaaggcctt cttggctgat ccatctgcct tgtggctgc tgcccctgtg | 1020 |
| gctgctgcca ccacagctgc tcctgctgct gctgcagccc cagctaaggt tgaagccaag | 1080 |
| gaagagtcgg aggagtcgga cgaggatatg ggatttggtc tctttgacta atcaccaaaa | 1140 |
| agcaaccaac ttagccagtt ttatttgcaa aacaaggaaa taaaggctta cttctttaaa | 1200 |
| aagtaaaaaa aaaaaaaaaa aaaaaaaaa | 1229 |

<210> SEQ ID NO 20
<211> LENGTH: 2772
<212> TYPE: DNA
<213> ORGANISM: Homo sapiens

<400> SEQUENCE: 20

| | |
|---|---:|
| agtcttttgt cggcggctcg acctgcgcgt gcgccgcagt cacgtggagg gcggggggg | 60 |
| tggtcgactg cggcggcagc tctttcctca gaccccagc cttttgtgcg ccgcgcggtg | 120 |
| gggcggtgcc cagcttgggg gaaggagagc ggcgcttatc gaagtgtggt cgacctccat | 180 |
| ccgcccaccg agcacttggg acccgctgca catatccaga gcagggaaag ctgtggcttt | 240 |
| ctcgggggag cgagtgtcta ggggaagggt gtggcaggcc cacgggatgc catgccctag | 300 |
| aacaacggcc tgacgcgcttg tggaattaaa atggagatg tggggccgag gtgggcgaat | 360 |
| tgggatccct ccaggtcagg ggttcgagac catcctgggc aacaaagcga gaccctcccc | 420 |
| catgccacgt ttctacaaaa aataaaattc tgggaggtga tcagtgatga acatggcatc | 480 |
| gaccccaccg gcacctacca cggggacagc gacctgcagc tggaccgcat ctctgtgtac | 540 |
| tacaatgaag ccacaggtgg caaatatgtt cctcgtgcca tcctggtgga tctagaacct | 600 |
| gggaccatgg actctgttcg ctcaggtcct tttggccaga tctttagacc agacaacttt | 660 |
| gtatttggtc agtctggggc aggtaacaac tgggccaaag ccactacac agagggcgcc | 720 |
| gagctggttg attctgtcct ggatgtggta cggaaggagg cagagagctg tgactgcctg | 780 |
| cagggcttcc agctgaccca ctcactgggc ggggcacag gctctggaat gggcactctc | 840 |
| cttatcagca agatccgaga agaataccct gatcgcatca tgaataccctt cagtgtggtg | 900 |
| ccttcaccca agtgtctga caccgtggtc gagccctaca tgccacccct ctccgtccat | 960 |
| cagttggtag agaatactga tgagacctat tgcattgaca acgaggccct ctatgatatc | 1020 |
| tgcttccgca ctctgaagct gaccacacca acctacgggg atctgaacca ccttgtctca | 1080 |
| gccaccatga gtggtgtcac cacctgcctc cgtttccctg ccagctcaa tgctgacctc | 1140 |
| cgcaagttgg cagtcaacat ggtccccttc ccacgtctcc atttctttat gcctggcttt | 1200 |
| gcccctctca ccagccgtgg aagccagcag tatcgagctc tcacagtgcc ggaactcacc | 1260 |
| cagcaggtct tcgatgccaa gaacatgatg gctgcctgtg accccgcca cggccgatac | 1320 |
| ctcaccgtgg ctgctgtctt ccgtggtcgg atgtccatga aggaggtcga tgagcagatg | 1380 |
| cttaacgtgc agaacaagaa cagcagctac tttgtggaat ggatcccaa caatgtcaag | 1440 |
| acagccgtct gtgacatccc acctcgtggc ctcaagatgg cagtcacctt cattggcaat | 1500 |

```
agcacagcca tccaggagct cttcaagcgc atctcggagc agttcactgc catgttccgc    1560
cggaaggcct tcctccactg gtacacaggc gagggcatgg acgagatgga gttcaccgag    1620
gctgagagca acatgaacga cctcgtctct gagtatcagc agtaccagga tgccaccgca    1680
gaagaggagg aggatttcgg tgaggaggcc gaagaggagg cctaaggcag agccccatc     1740 acctcaggct tctcagttcc cttagccgtc ttactcaact gccccttttcc tctccctcag   1800 aatttgtgtt tgctgcctct atcttgtttt ttgttttttc ttctgggggg ggtctagaac    1860
agtgcctggc acatagtagg cgctcaataa atacttgttt gttgaatgtc tcctctctct    1920
ttccactctg ggaaacctag gtttctgcca ttctgggtga ccctgtattt ctttctggtg    1980
cccattccat ttgtccagtt aatacttcct cttaaaaatc tccaagaagc tgggtctcca    2040
gatcccattt agaaccaacc aggtgctgaa aacacatgta gataatgcc atcatcctaa     2100 gcccaaagta gaaaatggta gaaggtagtg ggtagaagtc actatataag gaaggggatg    2160
ggattttcca ttctaaaagt tttggagagg gaaatccagg ctattaaagt cactaaattt    2220
ctaagtatgt ccatttccca tctcagcttc aagggaggtg tcagcagtat tatctccact    2280
ttcaatctcc ctccaagctc tactctggag gagtctgtcc cactctgtca agtggaatcc    2340 ttcccttttcc aactctacct ccctcactca gctccttttcc cctgatcaga gaaagggatc   2400
aagggggttg ggaggggggga aagagaccag ccttggtccc taagcctcca gaaacgtctt   2460
cttaatcccc accttttctt actcccaaaa agaatgaaac cccctgact ctggagtggt     2520 gtatactgcc acatcagtgt ttgagtcagt ccccagagga gagggaacc ctcctccatc     2580 ttttttgcaa catctcattt cttccttttg ctgttgcttc cccctcaca cacttggttt    2640 tgttctatcc tacatttgag atttctattt tatgttgaac ttgctgcttt ttttcatatt   2700 gaaagatga catcgcccca agagccaaaa ataaatggga attgaaaaaa gctgaaaaaa    2760
aaaaaaaaaa aa                                                       2772

<210> SEQ ID NO 21
<211> LENGTH: 1852
<212> TYPE: DNA
<213> ORGANISM: Homo sapiens

<400> SEQUENCE: 21
accgccgaga ccgcgtccgc cccgcgagca cagagcctcg cctttgccga tccgccgccc      60
gtccacaccc gccgccagct caccatggat gatgatatcg ccgcgctcgt cgtcgacaac    120
ggctccggca tgtgcaaggc cggcttcgcg ggcgacgatg ccccccgggc cgtcttcccc    180
tccatcgtgg ggcgccccag gcaccagggc gtgatggtgg gcatgggtca gaaggattcc    240
tatgtgggcg acgaggccca gagcaagaga ggcatcctca ccctgaagta ccccatcgag    300
cacggcatcg tcaccaactg ggacgacatg gagaaaatct ggcaccacac cttctacaat    360
gagctgcgtg tggctcccga ggagcacccc gtgctgctga ccgaggcccc cctgaacccc    420
aaggccaacc gcgagaagat gacccagatc atgtttgaga ccttcaacac cccagccatg    480
tacgttgcta tccaggctgt gctatcccct gtacgcctctg gccgtaccac tggcatcgtg    540
atggactccg gtgacgggt cacccacact gtgcccatct acgagggta tgccctcccc    600 catgccatcc tgcgtctgga cctggctggc cgggacctga ctgactacct catgaagatc    660
ctcaccgagc gcggctacag cttcaccacc acggccgagc gggaaatcgt gcgtgacatt    720
aaggagaagc tgtgctacgt cgccctggac ttcgagcaag agatggccac ggctgcttcc    780
```

| | |
|---|---|
| agctcctccc tggagaagag ctacgagctg cctgacggcc aggtcatcac cattggcaat | 840 |
| gagcggttcc gctgccctga ggcactcttc cagccttcct tcctgggcat ggagtcctgt | 900 |
| ggcatccacg aaactacctt caactccatc atgaagtgtg acgtggacat ccgcaaagac | 960 |
| ctgtacgcca acacagtgct gtctggcggc accaccatgt accctggcat tgccgacagg | 1020 |
| atgcagaagg agatcactgc cctggcaccc agcacaatga agatcaagat cattgctcct | 1080 |
| cctgagcgca gtactccgt gtggatcggc ggctccatcc tggcctcgct gtccaccttc | 1140 |
| cagcagatgt ggatcagcaa gcaggagtat gacgagtccg gcccctccat cgtccaccgc | 1200 |
| aaatgcttct aggcggacta tgacttagtt gcgttacacc ctttcttgac aaaacctaac | 1260 |
| ttgcgcagaa acaagatga gattggcatg gctttatttg ttttttttgt tttgtttttgg | 1320 |
| tttttttttt tttttttggct tgactcagga tttaaaaact ggaacggtga aggtgacagc | 1380 |
| agtcggttgg agcgagcatc ccccaaagtt cacaatgtgg ccgaggactt tgattgcaca | 1440 |
| ttgttgtttt tttaatagtc attccaaata tgagatgcgt tgttacagga agtcccttgc | 1500 |
| catcctaaaa gccaccccac ttctctctaa ggagaatggc ccagtcctct cccaagtcca | 1560 |
| cacaggggag gtgatagcat tgctttcgtg taaattatgt aatgcaaaat ttttttaatc | 1620 |
| ttcgccttaa tacttttta ttttgtttta ttttgaatga tgagccttcg tgcccccct | 1680 |
| tccccctttt ttgtccccca acttgagatg tatgaaggct tttggtctcc ctgggagtgg | 1740 |
| gtggaggcag ccagggctta cctgtacact gacttgagac cagttgaata aaagtgcaca | 1800 |
| ccttaaaaat gaaaaaaaaa aaaaaaaaaa aaaaaaaaaa aaaaaaaaaa aa | 1852 |

<210> SEQ ID NO 22
<211> LENGTH: 1869
<212> TYPE: DNA
<213> ORGANISM: Homo sapiens

<400> SEQUENCE: 22

| | |
|---|---|
| tacctggttg atcctgccag tagcatatgc ttgtctcaaa gattaagcca tgcatgtcta | 60 |
| agtacgcacg gccggtacag tgaaactgcg aatggctcat taaatcagtt atggttcctt | 120 |
| tggtcgctcg ctcctctccc acttggataa ctgtggtaat tctagagcta atacatgccg | 180 |
| acgggcgctg accccctttcg cgggggggat gcgtgcattt atcagatcaa aaccaacccg | 240 |
| gtcagcccct ctccggcccc ggccgggggg cgggcgccgg cggctttggt gactctagat | 300 |
| aacctcgggc cgatcgcacg cccccgtgg cggcgacgac ccattcgaac gtctgcccta | 360 |
| tcaactttcg atggtagtcg ccgtgcctac catggtgacc acgggtgacg gggaatcagg | 420 |
| gttcgattcc ggagagggag cctgagaaac ggctaccaca tccaaggaag gcagcaggcg | 480 |
| cgcaaattac ccactcccga cccgggggagg tagtgacgaa aaataacaat acaggactct | 540 |
| ttcgaggccc tgtaattgga atgagtccac tttaaatcct ttaacgagga tccattggag | 600 |
| ggcaagtctg gtgccagcag ccgcggtaat tccagctcca atagcgtata ttaaagttgc | 660 |
| tgcagttaaa aagctcgtag ttggatcttg ggagcgggcg gcggtccgc cgcgaggcga | 720 |
| gccaccgccc gtccccgccc cttgcctctc ggcgccccct cgatgctctt agctgagtgt | 780 |
| cccgcggggc ccgaagcgtt tactttgaaa aaattagagt gttcaaagca ggcccgagcc | 840 |
| gcctggatac cgcagctagg aataatggaa taggaccgcg gttctatttt gttggttttc | 900 |
| ggaactgagg ccatgattaa gagggacggc cggggcatt cgtattgcgc cgctagaggt | 960 |
| gaaattcttg gaccggcgca agacggacca gagcgaaagc atttgccaag aatgtttca | 1020 |
| ttaatcaaga acgaaagtcg gaggttcgaa gacgatcaga taccgtcgta gttccgacca | 1080 |

```
-continued taaacgatgc cgaccggcga tgcggcggcg ttattcccat gacccgccgg gcagcttccg    1140
ggaaaccaaa gtctttgggt tccgggggga gtatggttgc aaagctgaaa cttaaaggaa    1200
ttgacggaag ggcaccacca ggagtggagc ctgcggctta atttgactca acacgggaaa    1260
cctcacccgg cccggacacg gacaggattg acagattgat agctctttct cgattccgtg    1320
ggtggtggtg catggccgtt cttagttggt ggagcgattt gtctggttaa ttccgataac    1380
gaacgagact ctggcatgct aactagttac gcgaccccg agcggtcggc gtccccaac     1440 ttcttagagg gacaagtggc gttcagccac ccgagattga gcaataacag gtctgtgatg    1500
cccttagatg tccggggctg cacgcgcgct acactgactg gctcagcgtg tgcctaccct    1560
acgccggcag gcgcgggtaa cccgttgaac cccattcgtg atggggatcg gggattgcaa    1620
ttattcccca tgaacgagga attcccagta agtgcgggtc ataagcttgc gttgattaag    1680
tccctgccct ttgtacacac cgcccgtcgc tactaccgat tggatggttt agtgaggccc    1740
tcggatcggc cccgccgggg tcggcccacg gccctggcgg agcgctgaga agacggtcga    1800
acttgactat ctagaggaag taaaagtcgt aacaaggttt ccgtaggtga acctgcggaa    1860
ggatcatta                                                            1869
```